United States Patent
Tang et al.

(10) Patent No.: US 8,207,161 B2
(45) Date of Patent: Jun. 26, 2012

(54) TETRAHYDRO-IMIDAZO[1,5-α]PYRAZINE DERIVATIVES, PREPARATION PROCESS AND MEDICINAL USE THEREOF

(75) Inventors: Peng Cho Tang, Shanghai (CN); Fanglong Yang, Shanghai (CN); Jiang Fan, Shanghai (CN); Hu Feng, Shanghai (CN); Yang Wang, Shanghai (CN); Tao Yang, Shanghai (CN)

(73) Assignees: Jiangsu Hengrui Medicine Co. Ltd., Jiangsu (CN); Shanghai Hengrui Pharmaceutical Co. Ltd., Shanghai (CN)

( * ) Notice: Subject to any disclaimer, the term of this patent is extended or adjusted under 35 U.S.C. 154(b) by 95 days.

(21) Appl. No.: 12/743,795

(22) PCT Filed: Nov. 27, 2008

(86) PCT No.: PCT/CN2008/001936
§ 371 (c)(1),
(2), (4) Date: May 19, 2010

(87) PCT Pub. No.: WO2009/082881
PCT Pub. Date: Jul. 9, 2009

(65) Prior Publication Data
US 2010/0273786 A1    Oct. 28, 2010

(30) Foreign Application Priority Data
Dec. 26, 2007    (CN) .......................... 2007 1 0302335

(51) Int. Cl.
| | |
|---|---|
| A61K 31/541 | (2006.01) |
| A61K 31/5377 | (2006.01) |
| A61K 31/519 | (2006.01) |
| C07D 487/04 | (2006.01) |
| C07D 413/14 | (2006.01) |
| C07D 279/12 | (2006.01) |
| C12N 9/99 | (2006.01) |
| A61P 3/10 | (2006.01) |
| A61P 3/04 | (2006.01) |

(52) U.S. Cl. ..................... 514/228.5; 544/350; 544/117; 544/58.2; 514/233.2; 514/249; 435/184

(58) Field of Classification Search ........................ None
See application file for complete search history.

(56) References Cited

U.S. PATENT DOCUMENTS
| | | |
|---|---|---|
| 5,462,928 A | 10/1995 | Bachovchin et al. |
| 5,543,396 A | 8/1996 | Powers et al. |
| 6,110,949 A | 8/2000 | Villhauer |

FOREIGN PATENT DOCUMENTS
| | | | |
|---|---|---|---|
| WO | WO 95/15309 | | 6/1995 |
| WO | WO 98/19998 | | 5/1998 |
| WO | WO 03/004498 | * | 1/2003 |
| WO | WO 03/004498 A1 | | 1/2003 |
| WO | WO 03/082817 A2 | | 10/2003 |
| WO | WO 2004/032836 A2 | | 4/2004 |
| WO | WO 2004/058266 | * | 7/2004 |
| WO | WO 2004/085661 A2 | | 10/2004 |

OTHER PUBLICATIONS

White et al. In Clinical Diabetes 26(2), 2008, 53-57.*
Amori et al. In JAMA 2007; 298(2):194-206.*
Hansen et al., "Glucagon-Like Peptide-1-(7-36)Amide is Transformed to Glucagon-Like Peptide-1-(9-36)Amide by Dipeptidyl Peptidase IV in the Capillaries Supplying the L Cells of the Porcine Intestine", Endocrinology, 1999 by The Endocrine society, vol. 40, No. 11, 8 pgs.
Kubryk et al., "Application of the asymmetric hydrogenation of enamines to the preparation of a beta-amino acid pharmacophore", Science Direct, Tetrahedron: Asymmetry 17 (2006) pp. 205-209.
Fao, et al., "Cobalt-Catalysed Carbonylation of Aryl Halides", Journal of Organometallic Chemistry, 285 (1985) pp. 293-303.
Fukuda et al., "Catalytic Asymmetric total Synthesis of (+)-Lactacystin", J. Org. Chem. 2006, 71, pp. 1220-1225.

* cited by examiner

Primary Examiner — Timothy Thomas
Assistant Examiner — Dennis Heyer
(74) Attorney, Agent, or Firm — Ryan L. Marshall; Brinks Hofer Gilson & Lione

(57) ABSTRACT

Tetrahydro-imidazo[1,5-a]pyrazine derivatives of formula (I), their preparation methods, pharmaceutical compositions containing the derivatives and uses thereof as medicaments, especially as dipeptidyl peptidase IV inhibitors, wherein the substituents of formula (I) are defined as same as the description.

(I)

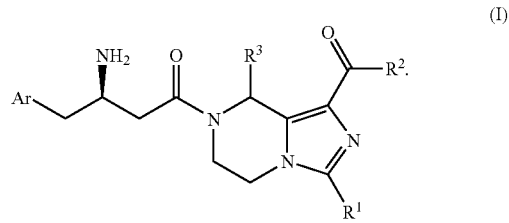

23 Claims, No Drawings

TETRAHYDRO-IMIDAZO[1,5-α]PYRAZINE DERIVATIVES, PREPARATION PROCESS AND MEDICINAL USE THEREOF

The present application is the national phase application of PCT Application No. PCT/CN2008/001936, filed Nov. 27, 2008, which claims priority to Chinese Patent Application No. 200710302335.9, filed Dec. 26, 2007, the entireties of both of which are hereby incorporated by references.

FIELD

The present invention relates to novel tetrahydro-imidazo [1,5-a]pyrazine derivatives having formula (I), methods for their preparation, pharmaceutical compositions containing them and therapeutic uses thereof, particularly their pharmaceutical use as a dipeptidyl peptidase IV inhibitor.

BACKGROUND

Diabetes is a disease caused by multiple factors and characterized by elevated levels of plasma glucose, or hyperglycemia, along with sugar, lipid and protein metabolic disorder caused by defects in insulin secretion and/or its function. Diabetes is an ancient disease. Absolute or relative lack of insulin in the human body results in increased concentrations of glucose in the blood and dramatic glucose discharges in urine, along with increased drinking, increased urining, increased eating, weight loss, dizziness, weakness and other symptoms.

Persistent or uncontrolled hyperglycemia is associated with increased and premature morbidity and mortality. Often abnormal glucose homeostasis is associated directly or indirectly with alterations of the lipid, lipoprotein and apolipoprotein metabolism and other metabolic and hemodynamic diseases. Patients with type 2 diabetes mellitus are at especially increased risk of macrovascular and microvascular complications, such as coronary heart disease, stroke, peripheral vascular disease, hypertension, nephropathy, neuropathy, and retinopathy. Therefore, therapeutical control of glucose homeostasis, lipid metabolism and hypertension is critically important in the clinical treatment of diabetes mellitus.

There are two generally recognized forms of diabetes. In type 1 diabetes, i.e., insulin-dependent diabetes mellitus (IDDM), patients produce little or no insulin, which is the hormone that regulates glucose utilization. In type 2 diabetes, i.e., noninsulin-dependent diabetes mellitus (NIDDM), patients often have plasma insulin levels that are the same or even elevated compared to nondiabetic subjects. However, these patients have developed a resistance to the insulin stimulating effect on glucose and lipid metabolism in the main insulin-sensitive tissues such as muscle, liver and adipose tissues, and the plasma insulin levels, even if elevated, are insufficient to overcome the pronounced insulin resistance.

Insulin resistance is not primarily due to a diminished number of insulin receptors but to a post-insulin receptor binding defect that is not yet understood so far. This resistance to insulin responsiveness results in insufficient insulin-dependent activation of glucose uptake, oxidation and storage in muscle, and inadequate repression of lipolysis in adipose tissue and of glucose production and secretion in the liver.

Dipeptidyl peptidase-IV (DPP-IV) is a serine protease which cleaves N-terminal dipeptides from a polypeptide containing a proline residue at the penultimate position. Although the biological role of DPP-IV in mammalian systems has not been completely established, it is believed to play an important role in neuropeptide metabolism, T-cell activation, adhesion and invasion of cancer cells to the endothelium and the entry of HIV into lymphoid cells (WO98/19998).

Recently, it was discovered that DPP-IV is responsible for preventing glucagon-like peptide-1 (GLP-1) secretion. More particularly, DPP-IV cleaves the amino-terminal His-Ala dipeptide of GLP-1, thus degrading the active GLP-1(7-36) $NH_2$ to the inactive GLP-1(9-36)$NH_2$ (Endocrinology, 1999, 140: 5356-5363). Under physiological conditions, the half-life of the whole GLP-1 in blood circulation is short. The inactive metabolite of GLP-1 after degradation by DPP-IV can bind with GLP-1 receptors, thus antagonize active GLP-1, and shorten the physiological responses to GLP-1. However, DPP-IV inhibitors can protect endogenous or even exogenous GLP-1 from being inactivated, and thus significantly increase GLP-1 bioactivity (5- to 10-fold). Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM) (U.S. Pat. No. 6,110,949).

Up to now, a few DPP-IV inhibitors have been disclosed (U.S. Pat. No. 5,462,928, U.S. Pat. No. 5,543,396, WO9515309, WO2003004498, WO2003082817, WO2004032836, WO2004085661), wherein Sitagliptin (MK-0431, Merk) shows good activity in inhibiting DPP-IV and selectivity. Among them, Sitagliptin went on sale in 2006.

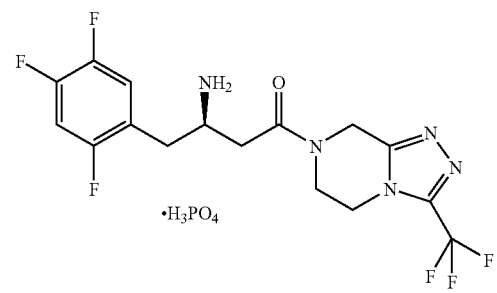

MK-0431

Although some DPP-IV inhibitors have been disclosed, there is no long effective drug at present. Improved DPP-IV inhibitors are needed.

The purpose of the present invention is to provide a series of compounds which can inhibit DPP-IV activity and be used for the treatment of diabetes or similar disease, or used as palliative drugs.

SUMMARY

In order to overcome the insufficiency of prior art, the present invention is directed to provide tetrahydro-imidazo [1,5-a]pyrazine derivatives having formula (I) and tautomers, enantiomers, diastereomers, racemics, pharmaceutically acceptable salts thereof, and metabolites, metabolic precursors or prodrugs thereof.

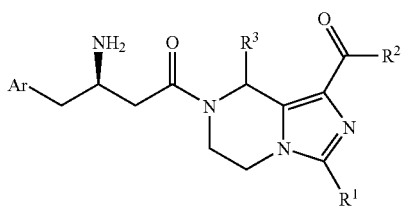

Wherein:

Ar is phenyl, wherein the phenyl is either unsubstituted or substituted with 1 to 5 $R^6$;

$R^1$ is selected from the group consisting of hydrogen, alkyl, trifluoromethyl, cycloalkyl, aryl and heteroaryl, wherein the alkyl, cycloalkyl, aryl or heteroaryl is each optionally substituted with one or more groups selected from the group consisting of halogen, cyano, aryl, hydroxyl and amino, preferably trifluoromethyl;

$R^2$ is selected from the group consisting of hydroxyl, amino, alkyl, alkoxyl, cycloalkyl, heterocyclic alkyl, aryl, heteroaryl and —$NR^4R^5$, wherein the alkyl, alkoxyl, cycloalkyl, heterocyclic alkyl, aryl or heteroaryl is each optionally substituted with one or more groups selected from the group consisting of halogen, amino, cyano, hydroxyl, alkyl, cycloalkyl, alkoxyl, aryl, heteroaryl, —$NR^4R^5$, —OC(O)$OR^8$, carboxylic acid and carboxylic ester;

$R^3$ is selected from the group consisting of hydrogen and alkyl;

$R^4$ and $R^5$ are each independently selected from the group consisting of hydrogen, alkyl, cycloalkyl, heterocyclic alkyl, aryl and heteroaryl, wherein the alkyl, cycloalkyl, heterocyclic alkyl, aryl or heteroaryl is each optionally substituted with one or more groups selected from the group consisting of halogen, hydroxyl, amino, alkoxyl, alkyl, cyano, aryl, cycloalkyl, heterocyclic alkyl, heterocyclic aryl, hydroxyalkyl, —$SO_2R^7$, —$NR^4R^5$, carboxylic acid and carboxylic ester;

or, $R^4$ and $R^5$ are taken together with the attached atom to form a 4 to 8 membered heterocycle, wherein the 4 to 8 membered heterocycle contains one or more N, O, S atoms, and the 4 to 8 membered heterocycle is optionally substituted with one or more groups selected from the group consisting of halogen, hydroxyl, amino, alkoxyl, alkyl, cyano, aryl, heterocyclic alkyl, heteroaryl, carbonyl, hydroxyalkyl, —$SO_2R^7$, —$NR^4R^5$, —C(O)$NR^4R^5$, —C(O)$R^7$, oxo, carboxylic acid and carboxylic ester;

$R^6$ is selected from the group consisting of halogen, cyano, hydroxyl, alkyl or alkoxyl, wherein the alkyl or alkoxyl is unsubstituted or each further substituted with one or more halogens;

$R^7$ is alkyl; and $R^8$ is selected from the group consisting of alkyl and cycloalkyl.

The pharmaceutically acceptable salts according to the present invention are those formed between the present compounds and acids preferably selected from the group consisting of malic acid, lactic acid, maleic acid, hydrochloric acid, methanesulfonic acid, sulfuric acid, phosphoric acid, citric acid, tartaric acid, acetic acid and trifluoroacetic acid.

Representative compounds of the present invention include, but are not limited to:

| Example No. | Structure | Name |
|---|---|---|
| 1 | 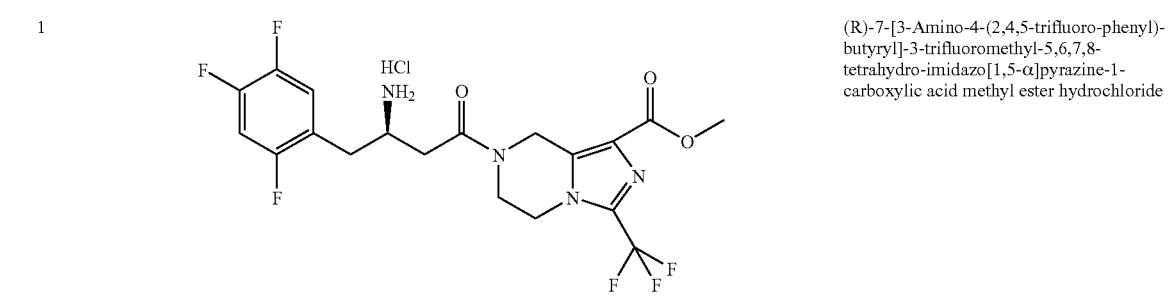 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid methyl ester hydrochloride |
| 2 | 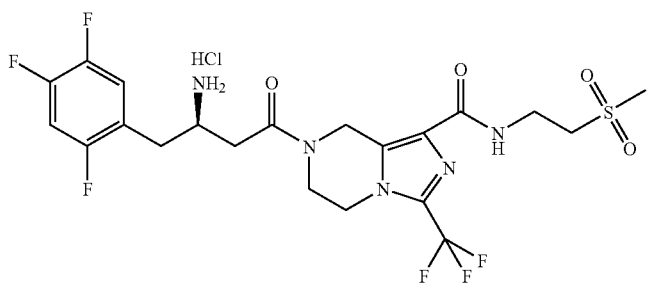 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (2-methanesulfonyl-ethyl)-amide hydrochloride |

| Example No. | Structure | Name |
|---|---|---|
| 3 | 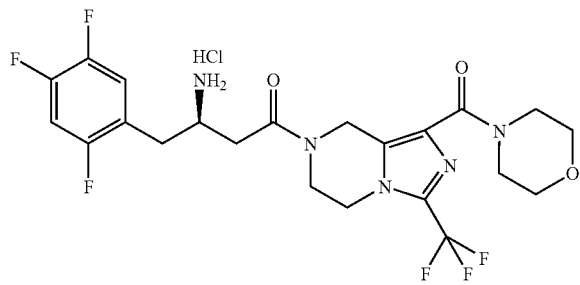 | (R)-3-Amino-1-[1-(morpholine-4-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 4 | 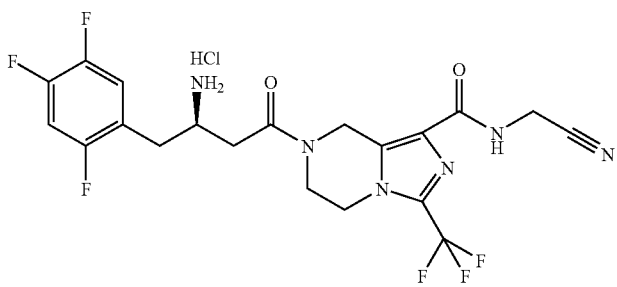 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid cyanomethyl-amide hydrochloride |
| 5 | 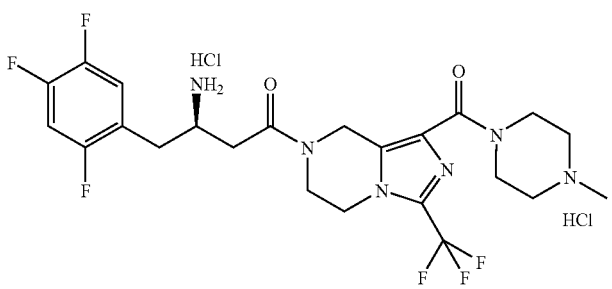 | (R)-3-Amino-1-[1-(4-methyl-piperazine-1-carbonyl)-3-trifluoromethyl-5,6-dihydro-8H-imidazo[1,5-α]pyrazin-7-yl]-4-(2,4,5-trifluoro-phenyl)-butan-1-one dihydrochloride |
| 6 | 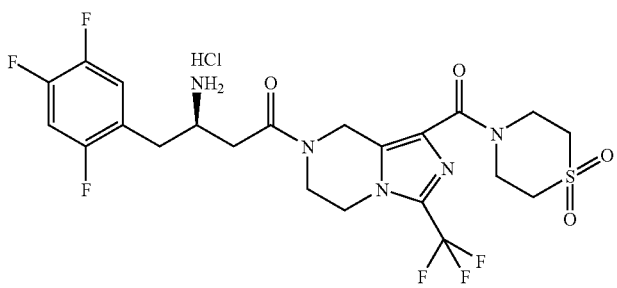 | (R)-3-Amino-1-[1-(1,1-dioxo-thiomorpholine-4-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 7 | 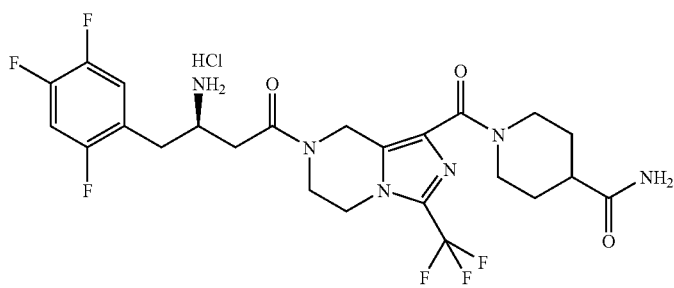 | (R)-1-{7-[3-Amino-4-(2,4,5-trifluoro-phenyl)-butyryl]-3-trifluoromethyl-5,6,7,8-tetrahydro-imidazo[1,5-α]pyrazine-1-carbonyl}-piperidine-4-carboxylic acid amide hydrochloride |

-continued

| Example No. | Structure | Name |
|---|---|---|
| 8 | 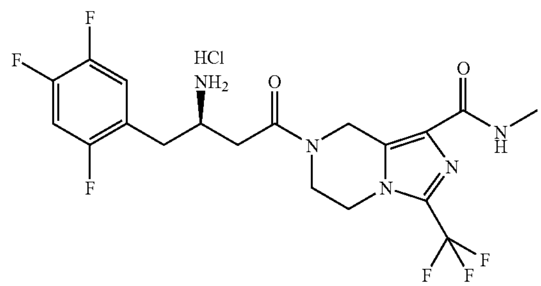 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid methylamide hydrochloride |
| 9 | 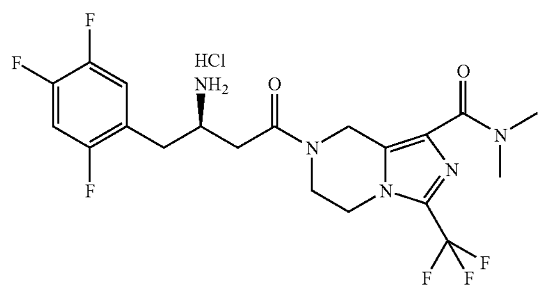 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid dimethylamide hydrochloride |
| 10 | 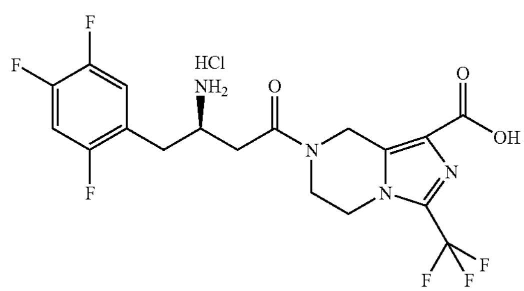 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid hydrochloride |
| 11 | 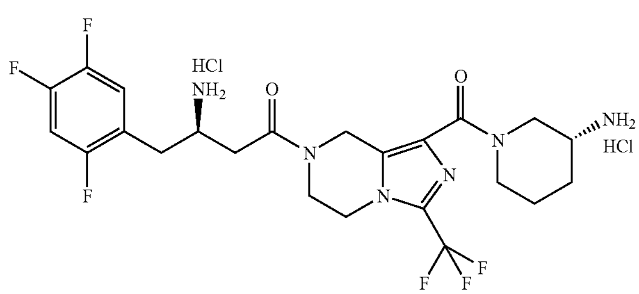 | (R)-3-Amino-1-[1-(3-amino-piperidine-1-carbonyl)-3-trifluoromethyl-5,6-dihydro-8H-imidazo[1,5-α]pyrazin-7-yl]-4-(2,4,5-trifluoro-phenyl)-butan-1-one dihydrochloride |
| 12 | 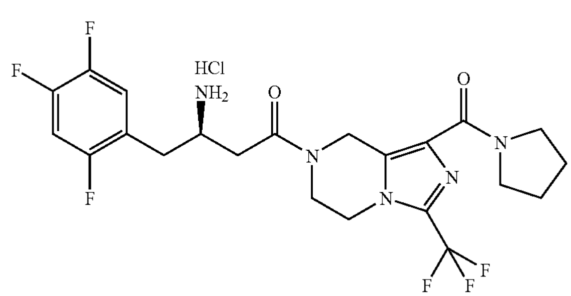 | (R)-3-Amino-1-[1-(pyrrolidine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |

-continued

| Example No. | Structure | Name |
|---|---|---|
| 13 | 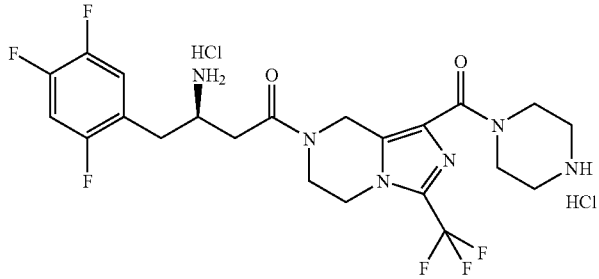 | (R)-3-Amino-1-[1-(piperazine-1-carbonyl)-3-trifluoromethyl-5,6-dihydro-8H-imidazo[1,5-α]pyrazin-7-yl]-4-(2,4,5-trifluoro-phenyl)-butan-1-one dihydrochloride |
| 14 | 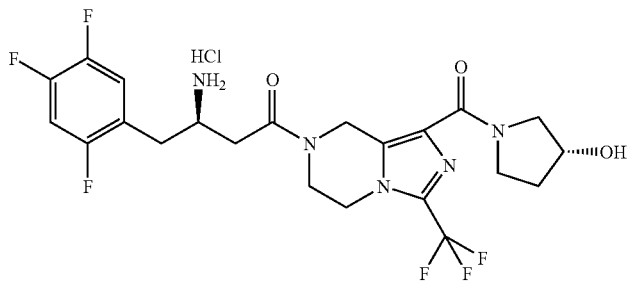 | (R)-3-Amino-1-[1-((R)-3-hydroxy-pyrrolidine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 15 | 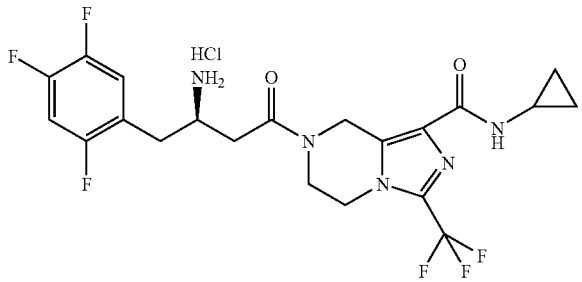 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid cyclopropylamide hydrochloride |
| 16 | 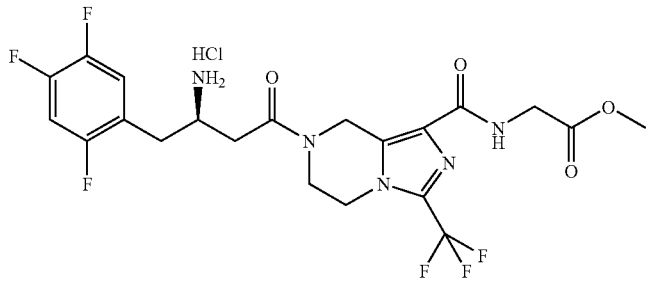 | (R)-({7-[3-Amino-4-(2,4,5-trifluoro-phenyl)-butyryl]-3-trifluoromethyl-5,6,7,8-tetrahydro-imidazo[1,5-α]pyrazine-1-carbonyl}-amino)-acetic acid methyl ester hydrochloride |
| 17 | 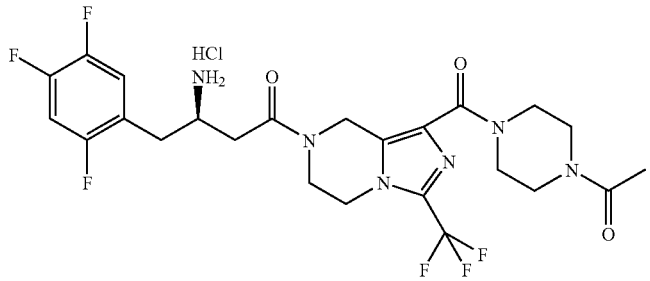 | (R)-1-[1-(4-Acetyl-piperazine-1-carbonyl)-3-trifluoromethyl-5,6-dihydro-8H-imidazo[1,5-α]pyrazin-7-yl]-3-amino-4-(2,4,5-trifluoro-phenyl)-butan-1-one hydrochloride |

-continued

| Example No. | Structure | Name |
|---|---|---|
| 18 | 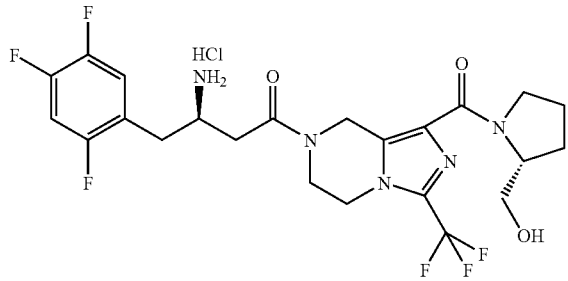 | (R)-3-Amino-1-[1-(2-hydroxymethyl-pyrrolidine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 19 | 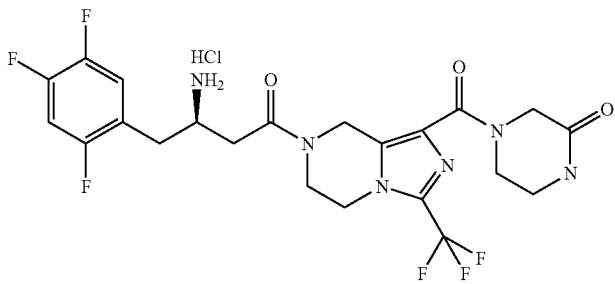 | (R)-4-{7-[3-Amino-4-(2,4,5-trifluoro-phenyl)-butyryl]-3-trifluoromethyl-5,6,7,8-tetrahydro-imidazo[1,5-α]pyrazine-1-carbonyl}-piperazin-2-one hydrochloride |
| 20 | 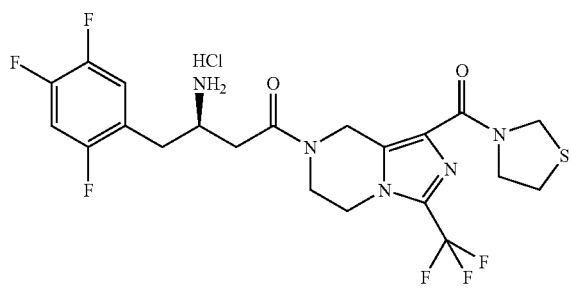 | (R)-3-Amino-1-[1-(thiazolidine-3-carbonyl)-3-trifluoromethy1-5,6-dihydro-8H-imidazo[1,5-α]pyrazin-7-yl]-4-(2,4,5-trifluoro-phenyl)-butan-1-one hydrochloride |
| 21 | 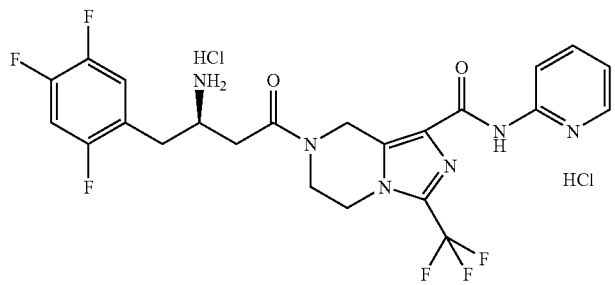 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (pyridin-2-yl) amide dihydrochloride |
| 22 | 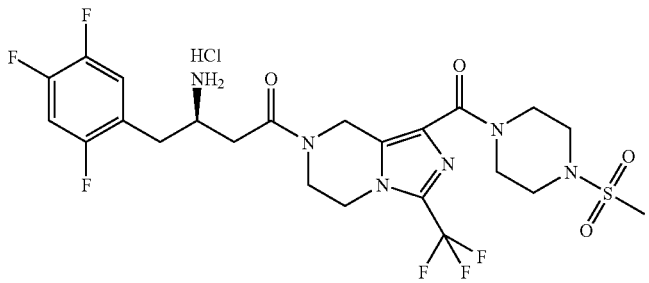 | (R)-3-Amino-1-[1-(4-methanesulfonyl-piperazine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |

-continued

| Example No. | Structure | Name |
|---|---|---|
| 23 | 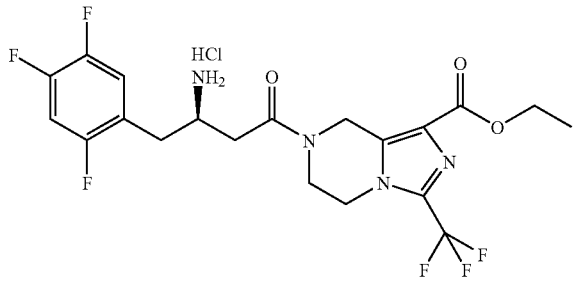 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid ethyl ester hydrochloride |
| 24 | 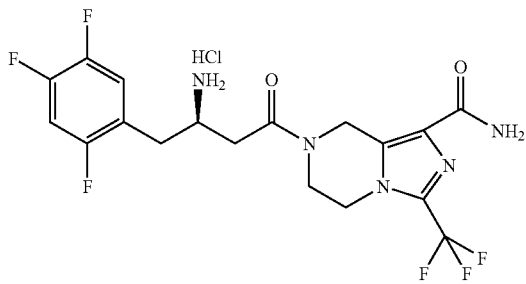 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid amide hydrochloride |
| 25 | 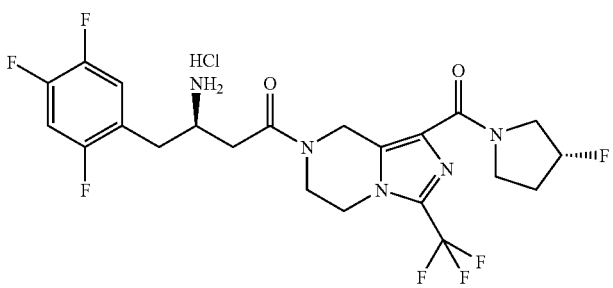 | (R)-3-Amino-1-[1-((R)-3-fluoro-pyrrolidine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 26 | 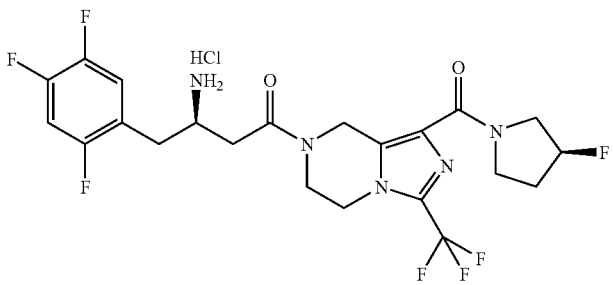 | (R)-3-Amino-1-[1-((S)-3-fluoro-pyrrolidine-1-carbonyl)-3-trifluoromethyl-5,6-dihydro-8H-imidazo[1,5-α]pyrazin-7-yl]-4-(2,4,5-trifluoro-phenyl)-butan-1-one hydrochloride |
| 27 | 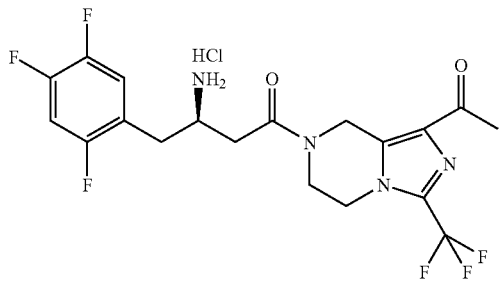 | (R)-1-(1-Acetyl-3-trifluoromethyl-5,6-dihydro-8H-imidazo[1,5-α]pyrazin-7-yl)-3-amino-4-(2,4,5-trifluoro-phenyl)butan-1-one hydrochloride |

-continued

| Example No. | Structure | Name |
|---|---|---|
| 28 | 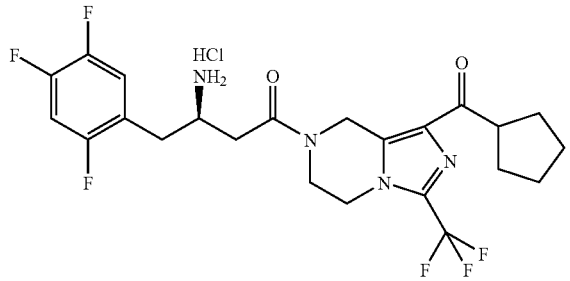 | (R)-3-Amino-1-(1-cyclopentanecarbonyl-3-trifluoromethyl-5,6-dihydro-8H-imidazol[1,5-α]pyrazin-7-yl)-4-(2,4,5-trifluoro-phenyl)-butan-1-one hydrochloride |
| 29 | 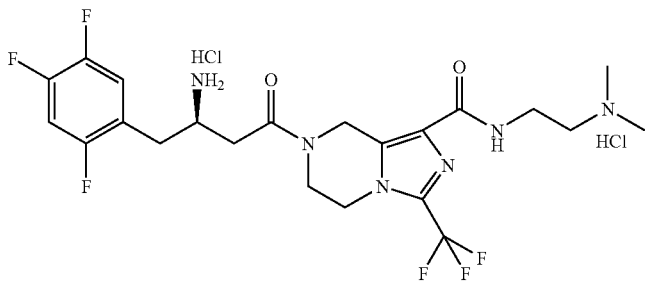 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (2-dimethylamino-ethyl)-amide dihydrochloride |
| 30 | 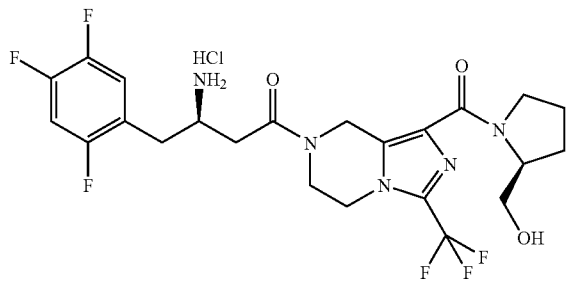 | (R)-3-Amino-1-[1-((S)-2-hydroxymethyl-pyrrolidine-1-carbonyl)-3-trifluoromethyl-5,6-dihydro-8H-imidazo[1,5-α]pyrazin-7-yl]-4-(2,4,5-trifluoro-phenyl)butan-1-one hydrochloride |
| 31 | 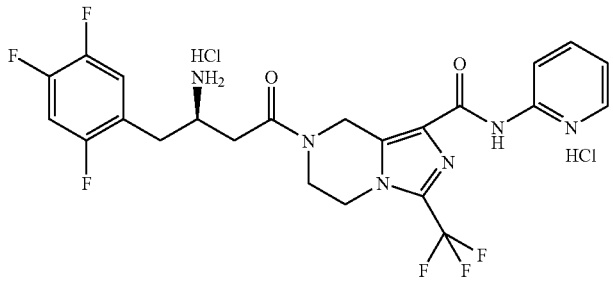 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (pyridin-2-yl) amide dihydrochloride |
| 32 | 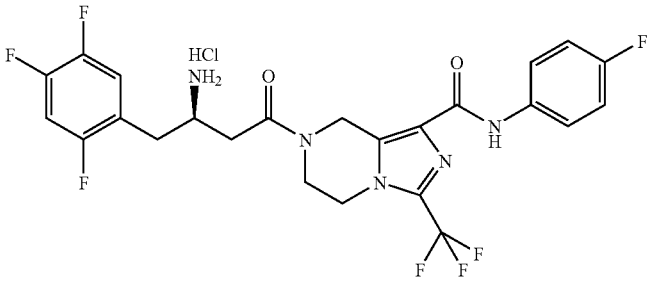 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (4-fluoro-phenyl)-amide hydrochloride |

-continued

| Example No. | Structure | Name |
|---|---|---|
| 33 | 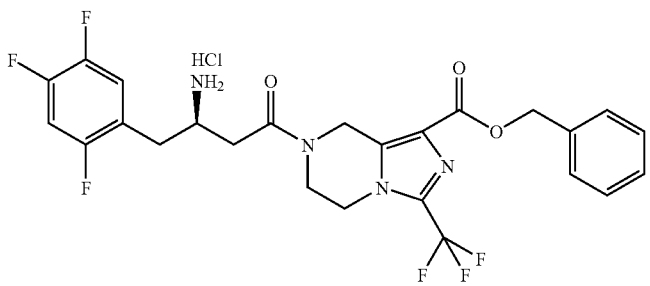 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid benzyl ester hydrochloride |
| 34 | 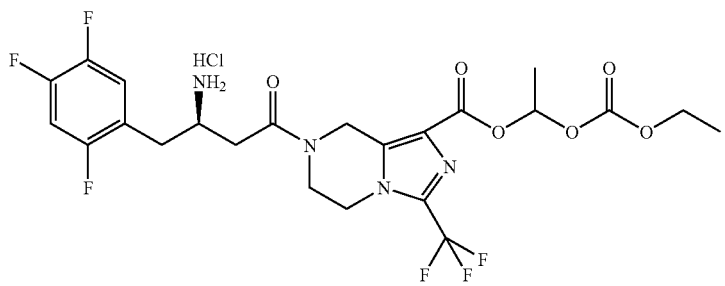 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (1-ethoxycarbonyloxy)-ethyl ester hydrochloride |
| 35 | 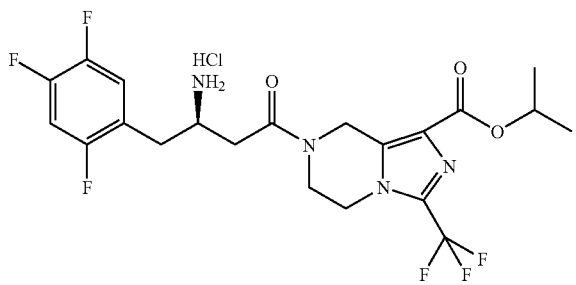 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid isopropyl ester hydrochloride |
| 36 | 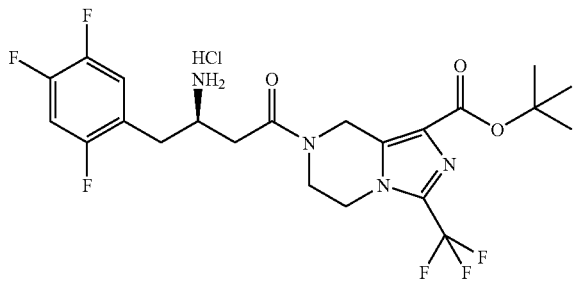 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid tert-butyl ester hydrochloride |
| 37 | 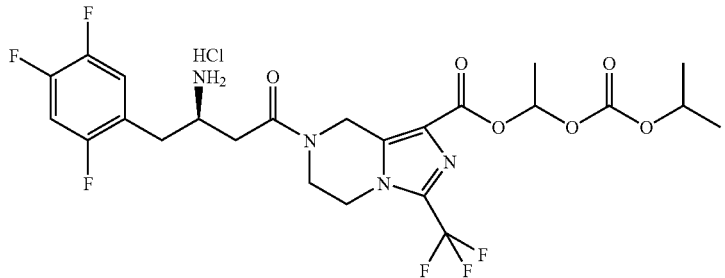 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid 1-isopropoxycarbonyloxy-ethyl ester hydrochloride |

-continued

| Example No. | Structure | Name |
|---|---|---|
| 38 | 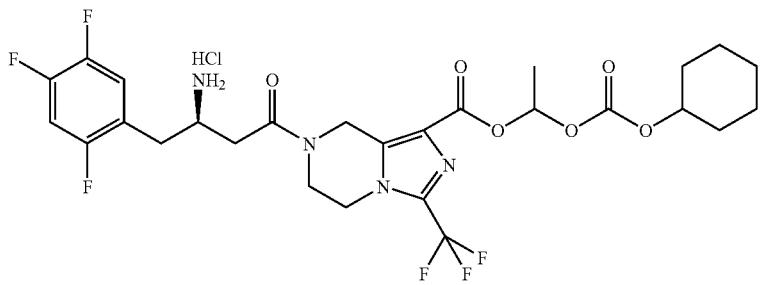 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid (1-cyclohexyloxycarbonyloxy)-ethyl ester hydrochloride |
| 39 | 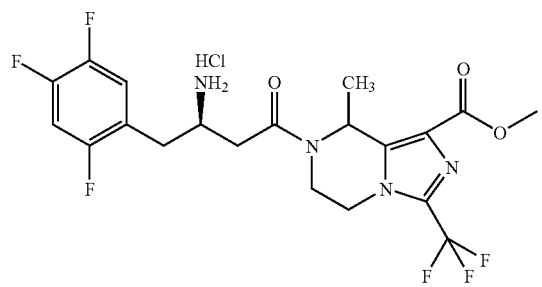 | (R)-7-[3-Amino-4-(2,4,5-trifluoro-phenyl)-butyryl]-8-methyl-3-trifluoromethyl-5,6,7,8-tetrahydro-imidazo[1,5-α]pyrazine-1-carboxylic acid methyl ester hydrochloride |
| 40 | 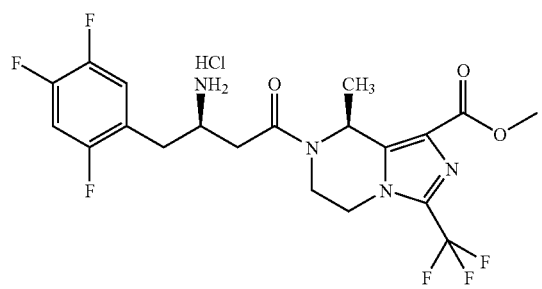 | (R)-7-[3-Amino-4-(2,4,5-trifluoro-phenyl)-butyryl]-(S)-8-methyl-3-trifluoromethyl-5,6,7,8-tetrahydro-imidazo[1,5-α]pyrazine-1-carboxylic acid methyl ester hydrochloride |
| 41 | 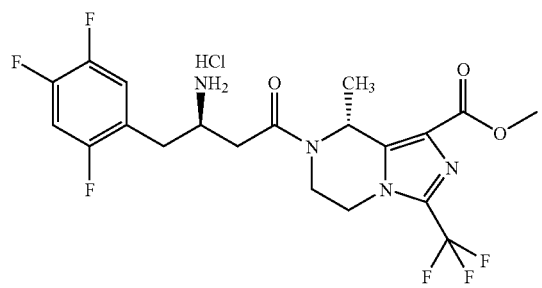 | (R)-7-[3-Amino-4-(2,4,5-trifluoro-phenyl)-butyryl]-(R)-8-methyl-3-trifluoromethyl-5,6,7,8-tetrahydro-imidazo[1,5-α]pyrazine-1-carboxylic acid methyl ester hydrochloride |
| 42 | 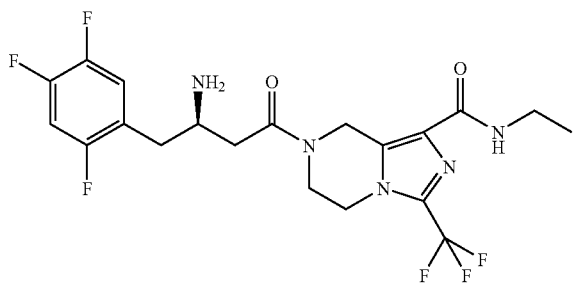 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid ethylamide |

-continued

| Example No. | Structure | Name |
|---|---|---|
| 43 | 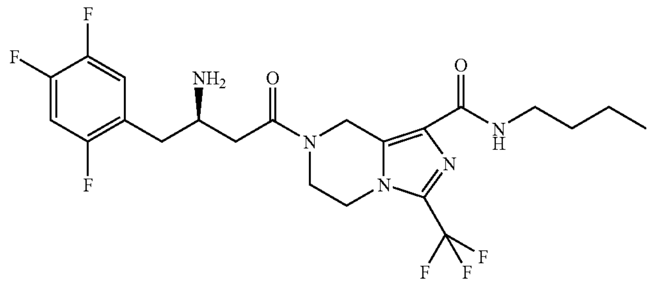 | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid butylamide |
| 44 | | (R)-7-[3-Amino-4-(2,4,5-trifluoro-phenyl)-butyryl]-3-trifluoromethyl-5,6,7,8-tetrahydro-imidazo[1,5-α]pyrazine-1-carboxylic acid propylamide | or pharmaceutically acceptable salts thereof.

Further, the present invention relates to the following compounds having formula (IA) as intermediates in the synthesis of compounds having formula (I):

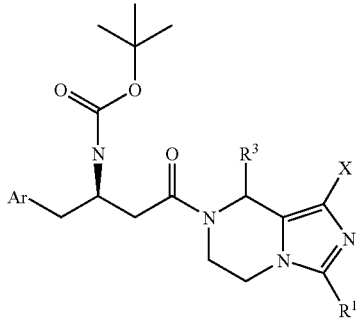

(IA)

Wherein:

Ar is phenyl, wherein the phenyl is either unsubstituted or substituted with 1 to 5 $R^6$;

$R^1$ is selected from the group consisting of hydrogen, alkyl, trifluoromethyl, cycloalkyl, aryl and heteroaryl, wherein the alkyl, cycloalkyl, aryl or heteroaryl is each optionally substituted with one or more groups selected from the group consisting of halogen, cyano, aryl, hydroxyl and amino, preferably trifluoromethyl;

$R^3$ is selected from the group consisting of hydrogen and alkyl;

$R^6$ is selected from the group consisting of halogen, cyano, hydroxyl, alkyl or alkoxyl, wherein the alkyl or alkoxyl is unsubstituted or each further substituted with one or more halogens; and X is halogen.

Further, the present invention relates to the compounds having the following formula (IB) as intermediates in the synthesis of compounds having formula (I)

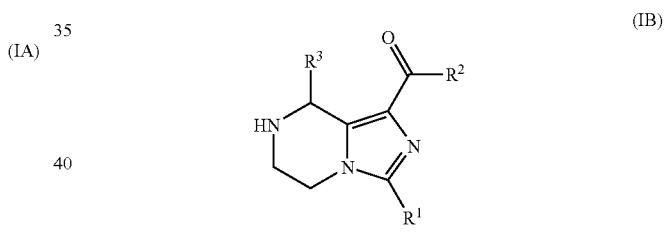

(IB)

Wherein:

$R^1$ is selected from the group consisting of hydrogen, alkyl, trifluoromethyl, cycloalkyl, aryl and heteroaryl, wherein the alkyl, cycloalkyl, aryl or heteroaryl is each optionally substituted with one or more groups selected from the group consisting of halogen, cyano, aryl, hydroxyl and amino, preferably trifluoromethyl;

$R^2$ is selected from the group consisting of hydroxyl, amino, alkyl, alkoxyl, cycloalkyl, heterocyclic alkyl, aryl, heteroaryl and —$NR^4R^5$, wherein the alkyl, alkoxyl, cycloalkyl, heterocyclic alkyl, aryl or heteroaryl is each optionally substituted with one or more groups selected from the group consisting of halogen, amino, cyano, hydroxyl, alkyl, cycloalkyl, alkoxyl, aryl, heteroaryl, —$NR^4R^5$, —OC(O)O$R^8$, carboxylic acid and carboxylic ester;

$R^3$ is selected from the group consisting of hydrogen and alkyl;

$R^4$ and $R^5$ are each independently selected from the group consisting of hydrogen, alkyl, cycloalkyl, heterocyclic alkyl, aryl and heteroaryl, wherein the alkyl, cycloalkyl, heterocyclic alkyl, aryl or heteroaryl is each optionally substituted with one or more groups selected from the group consisting of halogen, hydroxyl, amino, alkoxyl, alkyl, cyano, aryl, cycloalkyl, heterocyclic alkyl, heteroaryl, hydroxyalkyl, —SO$_2$R$^7$, —NR$^4$R$^5$, carboxylic acid and carboxylic ester;

Or, R$^4$ and R$^5$ are taken together with the attached atom to form a 4 to 8 membered heterocycle, wherein the 4 to 8 membered heterocycle contains one or more N, O, S atoms, and the 4 to 8 membered heterocycle so formed is optionally substituted with one or more groups selected from the group consisting of halogen, hydroxyl, amino, alkoxyl, alkyl, cyano, aryl, heterocyclic alkyl, heteroaryl, carbonyl, hydroxyalkyl, —SO$_2$R$^7$, —NR$^4$R$^5$, —C(O)NR$^4$R$^5$, —C(O)R$^7$, carboxylic acid and carboxylic ester;

R$^7$ is alkyl; and

R$^8$ is selected from the group consisting of alkyl and cycloalkyl.

Another aspect of the present invention is directed to the preparation process of intermediates having formula (IA), wherein the preparation process comprises the following steps of:

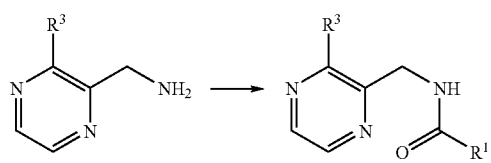

adding dropwise an acid anhydride into the starting material pyrazine 2-methylamine in an ice-water bath and then stirring the reaction mixture at room temperature to obtain an amide product;

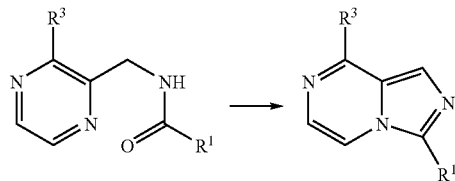

mixing the amide product and phosphorus oxychloride at room temperature and then adding phosphorous pentoxide to the resulting mixture; allowing the condensation reaction to occur by heating to reflux to obtain the condensation product imidazole[1,5-a]pyrazine derivative;

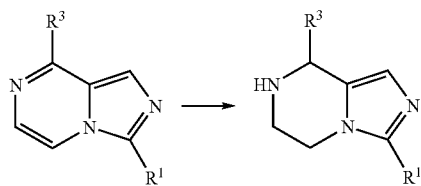

reducing the imidazole[1,5-a]pyrazine derivative in the solvent of ethanol, in the presence of a Pd/C catalyst, with hydrogen to obtain the R$^1$ and R$^3$ substituted tetrahydro-imidazo[1,5-a]pyrazine derivative;

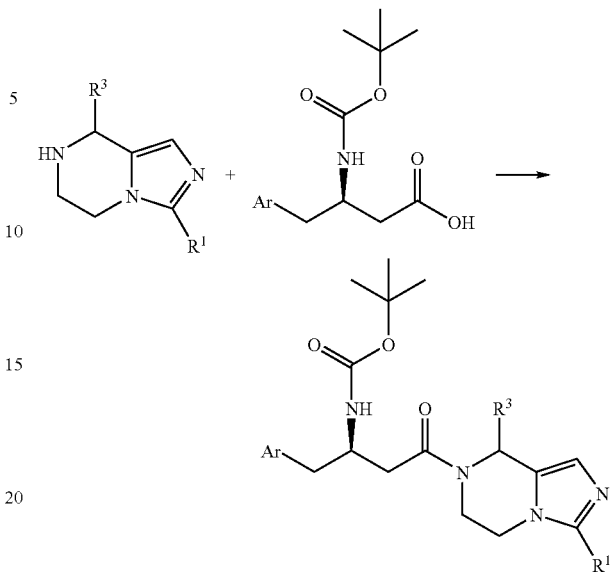

reacting the R$^1$ and R$^3$ substituted tetrahydro-imidazo[1,5-a]pyrazine derivative in the solvent of dichloromethane with a carboxylic acid in a condensation reaction, in the presence of a condensation reagent bis(2-oxo-3oxazolidinyl) phosphonic chloride and triethylamine;

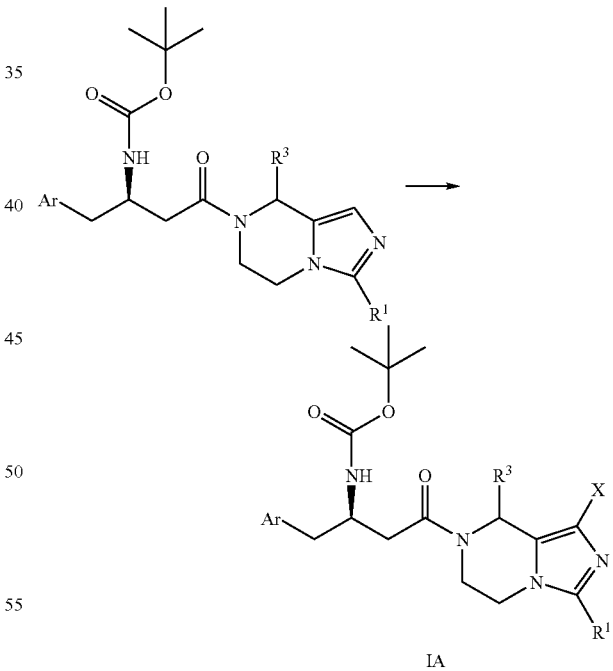

reacting the resulting condensation product with halogenated succinimide in the solvent of anhydrous ethanol at room temperature to obtain the intermediates having formula (IA).

Another aspect of the present invention is directed to the preparation process of intermediates having formula (IB), wherein the preparation process comprises the following steps of:

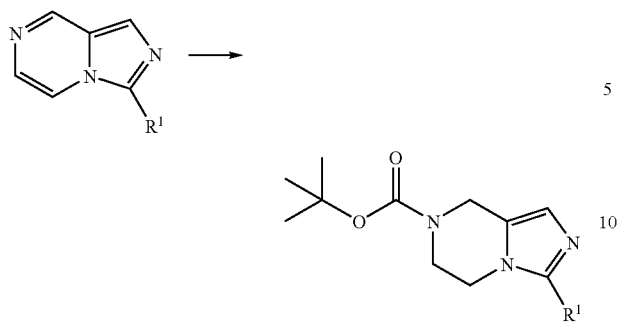

reducing the R[1] substituted imidazole[1,5-a]pyrazine derivative in the solvent of ethanol at room temperature by hydrogenation and then reacting the resulting reduced product with di-tert-butyl dicarbonate in the solvent of ethanol in order to protect the amino group to obtain the amino protected R[1] substituted imidazole[1,5-a]pyrazine derivative;

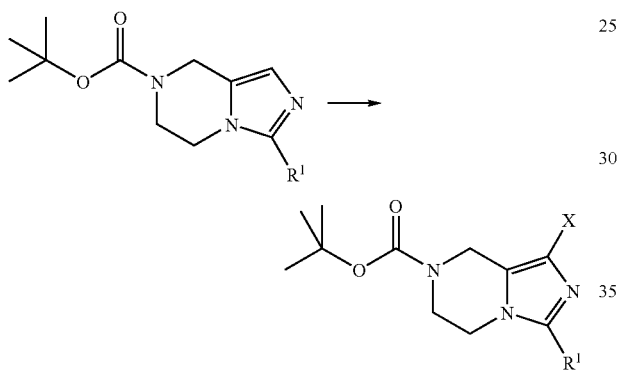

reacting the resulting amino protected R[1] substituted imidazole[1,5-a]pyrazine derivative with halogenated succinimide in the solvent of ethanol at room temperature to obtain the halogenated compound;

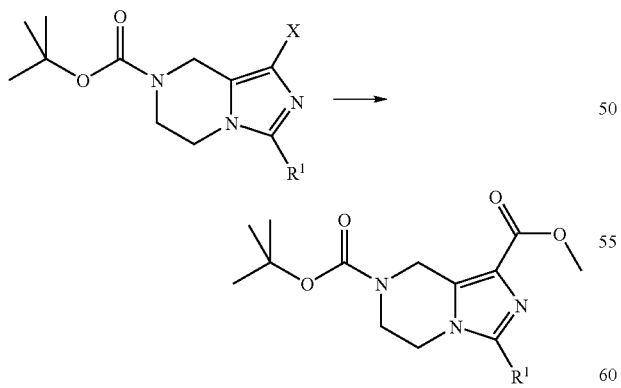

under a carbon monoxide atmosphere, reacting the resulting halogenated compound with cobalt octacarbonyl and chloracetate in the solvent of methanol in an oil bath to obtain the ester substituted tetrahydro-imidazo[1,5-a]pyrazine derivative;

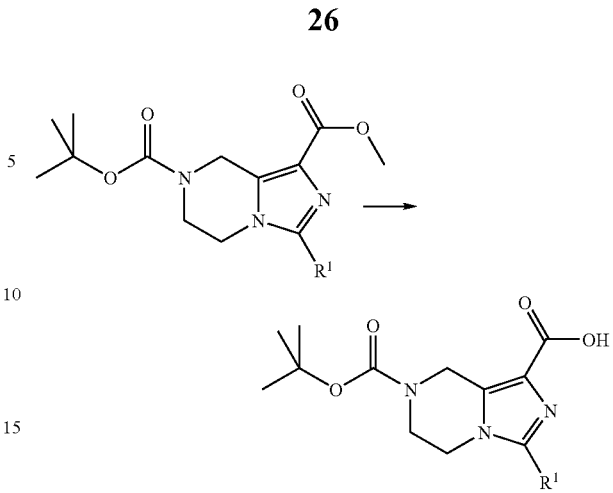

hydrolyzing the resulting ester substituted tetrahydro-imidazo[1,5-a]pyrazine derivative in the presence of a base to obtain the carboxylic acid compound;

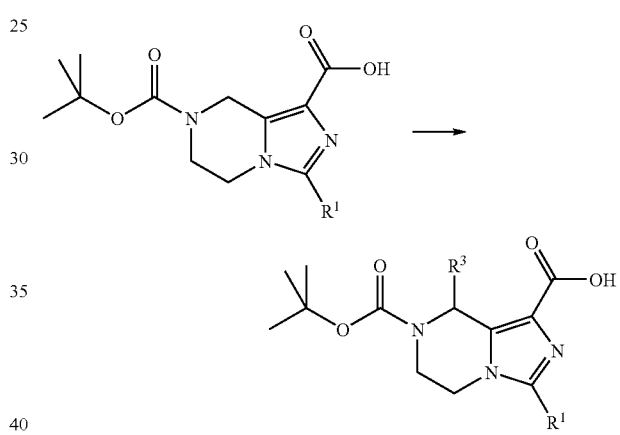

reacting the resulting carboxylic acid compound with an alkyl halide in a dry ice-acetone bath to obtain the alkyl substituted carboxylic acid;

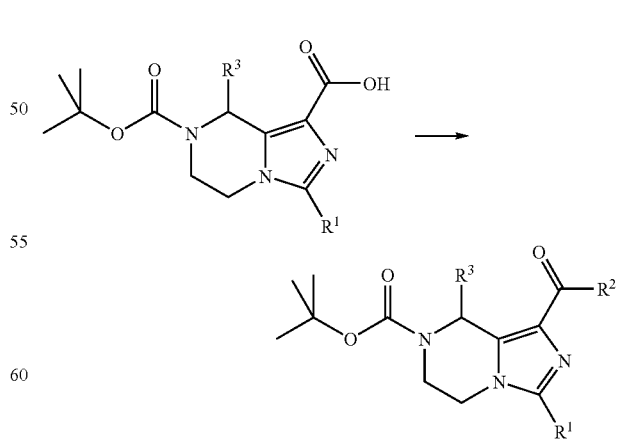

next, esterifying the alkyl substituted carboxylic acid to obtain the ketone substituted tetrahydro-imidazo[1,5-a]pyrazine derivative;

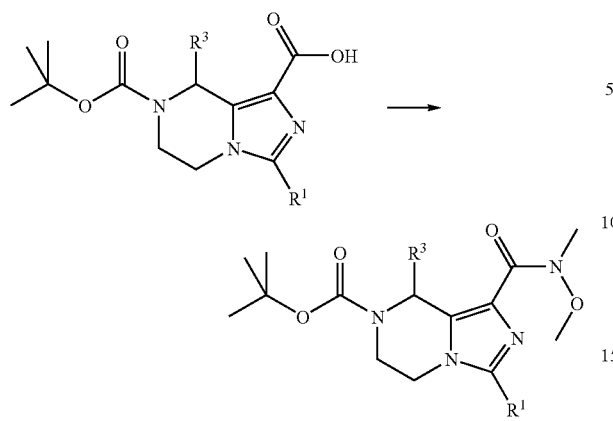

or, reacting the alkyl substituted carboxylic acid with N-methoxyl methylamine in the presence of a condensation reagent bis(2-oxo-3-oxazolidinyl) phosphonic chloride in the solvent of dichloromethane;

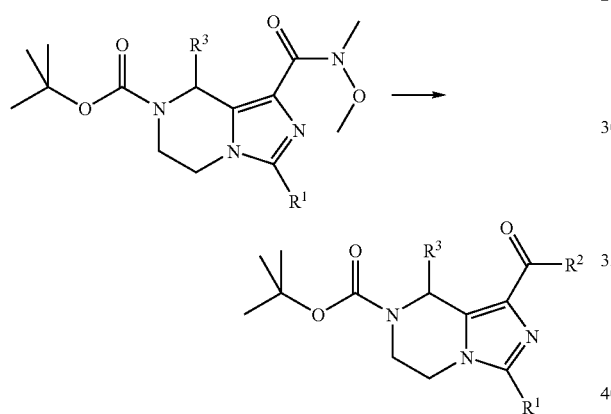

reacting the resulting condensation compounds with a Grignard reagent in the solvent of tetrahydrofuran to obtain the ketone substituted tetrahydro-imidazo[1,5-a]pyrazine derivative;

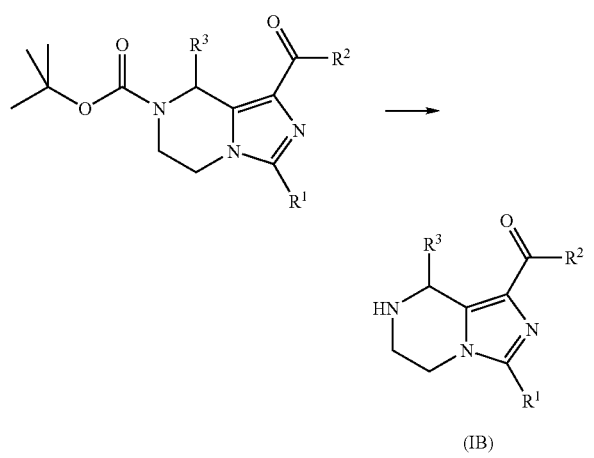

(IB)

deprotecting the amino protecting group from the ketone substituted tetrahydro-imidazo[1,5-a]pyrazine derivative in the presence of an acid to obtain the intermediate having formula (IB).

Furthermore, another aspect of the present invention is directed to the preparation process of compounds having formula (I), wherein the preparation process comprises the following steps of:

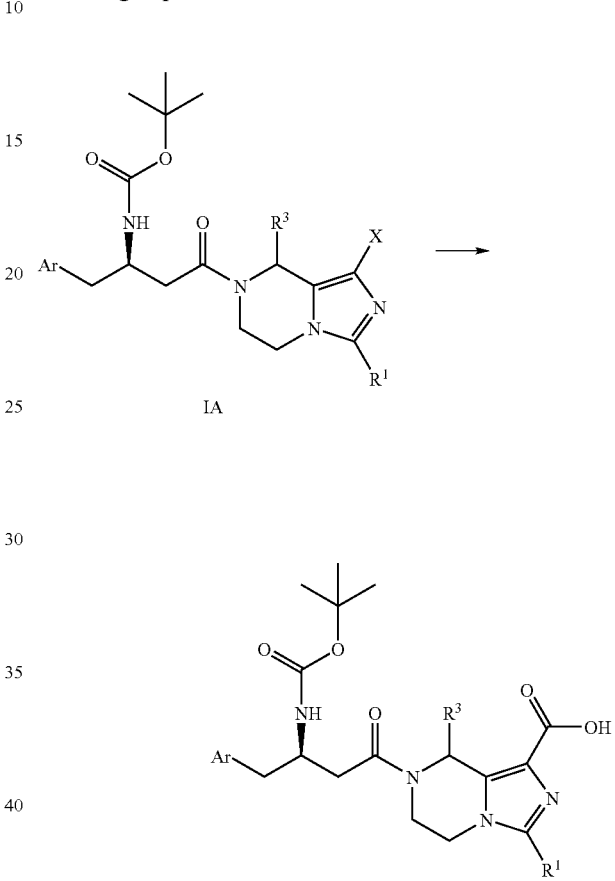

IA reacting the intermediate having formula (IA) with cobalt octacarbonyl and chloracetate in the solvent of methanol in an oil bath under a carbon monoxide atmosphere and then hydrolyzing the resulting product in the presence of a base at room temperature and acidifying it to obtain the carboxylic acid;

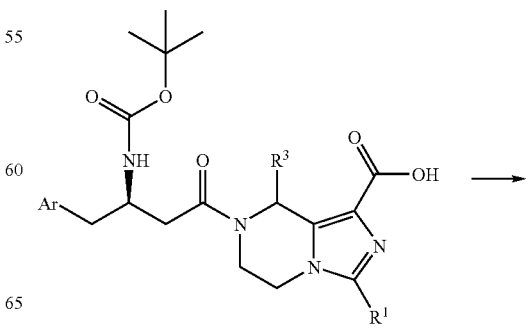

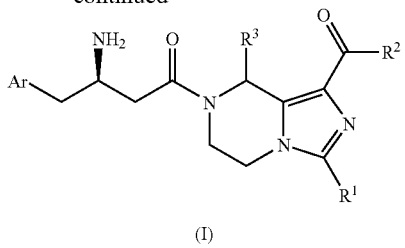

(I)

reacting the resulting carboxylic acid with an amine or an alcohol in the presence of a condensation reagent at room temperature or with 1-halogenated carbonate and then deprotecting the amino protecting group in the presence of an acid to obtain the compound having formula (I).

Another aspect of the present invention is directed to the preparation process of compounds having formula (I), wherein the preparation process comprises the following steps of:

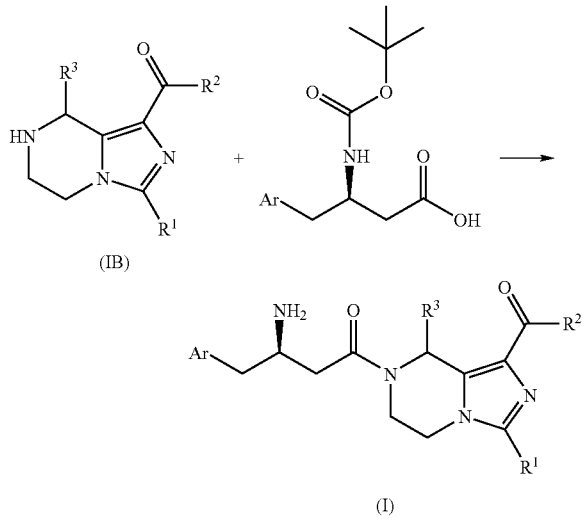

reacting the intermediate having formula (IB) with a carboxylic acid in the presence of a condensation reagent bis(2-oxo-3-oxazolidinyl)phosphonic chloride to obtain the condensation product and further deprotecting the amino protecting group in the presence of an acid to obtain the compound having formula (I).

Furthermore, the process of preparing the compounds having formula (I) also comprises the step of reacting the resulting compounds having formula (I) with acids to obtain the acid addition salts of the compounds having formula (I), the acids selected from the group consisting of phosphonic acid, malic acid, lactic acid, maleic acid, hydrochloric acid, methane sulfonic acid, sulfuric acid, phosphonic acid, citric acid, tartaric acid, acetic acid and trifluoroacetic acid, preferably hydrochloric acid.

The present invention relates to a pharmaceutical composition comprising a compound or pharmaceutically acceptable salt thereof according to the present invention in a therapeutically effective amount, as well as a pharmaceutically acceptable carrier or excipient.

In another aspect, the present invention relates to use of the compounds or pharmaceutically acceptable salts in the preparation of a medicament for the treatment of type 2 diabetes, hyperglycemia, obesity or insulin resistance.

In another aspect, the present invention relates to the method of inhibiting the catalytic activity of dipeptidyl peptidase IV, characterized in that the dipeptidyl peptidase-IV is contacted with any compound having formula (I) or pharmaceutically acceptable salt thereof.

In another aspect, the present invention relates to use of any compound having formula (I), salt thereof or the pharmaceutical composition for the treatment of type 2 diabetes, hyperglycemia, obesity or insulin resistance.

DETAILED DESCRIPTION OF THE PREFERRED EMBODIMENTS

Unless otherwise stated, the following terms used in the specification and claims have the meanings described below.

The term "alkyl" refers to a saturated aliphatic hydrocarbon group including $C_1$-$C_{20}$ straight chain and branched chain groups. Preferably an alkyl group is an alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl or tert-butyl, and the like.

The alkyl group may be substituted or unsubstituted. When substituted, the substituent group(s) is preferably one or more independently selected from the group consisting of halogen, hydroxyl, amino, alkoxyl, alkyl, cyano, aryl, heterocyclic alkyl, heteroaryl, carbonyl, hydroxyalkyl, —$SO_2R^7$, —$NR^4R^5$, —$C(O)NR^4R^5$, —$C(O)R^7$, —$OC(O)OR^8$, carboxylic acid and carboxylic ester.

The term "cycloalkyl" refers to a 3 to 8 membered all-carbon monocyclic ring, an all-carbon 5-membered/6-membered or 6-membered/6-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated π-electron system. Examples of cycloalkyl groups are cyclopropane, cyclobutane, cyclopentane, cyclopentene, cyclohexane, cyclohexadiene, adamantane, cycloheptane, cycloheptatriene, and the like. The cycloalkyl group may be substituted or unsubstituted. When substituted, the substituent group(s) is preferably one or more independently selected from the group consisting of halogen, hydroxyl, amino, alkoxyl, alkyl, cyano, aryl, heterocyclic alkyl, heteroaryl, carbonyl, hydroxyalkyl, —$SO_2R^7$, —$NR^4R^5$, —$C(O)NR^4R^5$, —$C(O)R^7$, carboxylic acid and carboxylic ester.

The term "aryl" refers to groups having at least one aromatic ring, i.e., having a conjugated π-electron system, and it includes all-carbon cyclic aryl, heteroaryl and biaryl group. The aryl group may be substituted or unsubstituted. When substituted, the substituent group(s) is preferably one or more independently selected from the group consisting of halogen, hydroxyl, amino, alkoxyl, alkyl, cyano, aryl, heterocyclic alkyl, heteroaryl, carbonyl, hydroxyalkyl, —$SO_2R^7$, —$NR^4R^5$, —$C(O)NR^4R^5$, —$C(O)R^7$, carboxylic acid and carboxylic ester.

The term "heteroaryl" refers to an aryl having 1 to 3 heteroatoms selected from the group consisting of N, O, and S as ring atoms, the remaining ring atoms being C. Said ring is 5- or 6-membered ring. The examples of heteroaryl groups include furyl, thienyl, pyridyl, pyrrolyl, N-alkyl pyrrolyl, pyrimidinyl, pyrazinyl, imidazolyl, and the like. The heteroaryl group may be substituted or unsubstituted. When substituted, the substituent group(s) is preferably one or more independently selected from the group consisting of halogen, hydroxyl, amino, alkoxyl, alkyl, cyano, aryl, heterocyclic alkyl, heteroaryl, carbonyl, hydroxyalkyl, —SO$_2$R$^7$, —NR$^4$R$^5$, —C(O)NR$^4$R$^5$, —C(O)R$^7$, carboxylic acid and carboxylic ester.

The term "heterocyclic alkyl" refers to a monocyclic or fused ring group having 5 to 9 ring atoms, wherein one or two ring heteroatoms are selected from the group consisting of N, O, and S(O)$_n$ (n is a integer from 0 to 2), the remaining ring atoms are C. In addition, the ring may also have one or more double bonds, but not have a completely conjugated r-electron system. The unsubstituted heterocyclic alkyl includes, but is not limited to pyrrolidyl, piperidyl, piperazinyl, morpholinyl, thiomorpholinyl, homopiperazinyl, and the like. The heterocyclic alkyl may be substituted or unsubstituted. When substituted, the substituent is preferably one or more independently selected from the group consisting of halogen, hydroxyl, amino, alkoxyl, alkyl, cyano, aryl, heterocyclic alkyl, heteroaryl, carbonyl, hydroxyalkyl, —SO$_2$R$^7$, —NR$^4$R$^5$, —C(O)NR$^4$R$^5$, —C(O)R$^7$, carboxylic acid and carboxylic ester.

The term "hydroxy" refers to an —OH group.

The term "alkoxyl" refers to both an —O-(alkyl) and an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like. The alkoxyl may be substituted or unsubstituted. When substituted, the substituent is preferably one or more independently selected from the group consisting of halogen, hydroxyl, amino, alkoxyl, alkyl, cyano, aryl, heterocyclic alkyl, heteroaryl, carbonyl, hydroxyalkyl, —SO$_2$R$^7$, —NR$^4$R$^5$, —C(O)NR$^4$R$^5$, —C(O)R$^7$, carboxylic acid and carboxylic ester.

The term "halogen" refers to fluoro, chloro, bromo or iodo, preferably fluoro or chloro.

The term "trifluoromethyl" refers to a —CF$_3$ group.

The term "amino" refers to a —NH$_2$ group.

The term "cyano" refers to a —C≡N group.

The term "carbonyl" refers to a C(═O) group.

The term "carboxylic acid" refers to a (alkyl) C(═O)OH group.

The term "carboxylic ester" refers to a (alkyl) C(═O)O (alkyl).

The term "hydroxylalkyl" refers to alkyl group substituted with hydroxyl.

A "pharmaceutical composition" refers to a mixture of one or more of the compounds described herein or physiologically/pharmaceutically acceptable salts or prodrugs thereof, with other chemical components such as physiologically/pharmaceutically acceptable carriers and excipients. The purpose of a pharmaceutical composition is to facilitate administration of a compound to an organism.

Synthesis Methods

In order to achieve the objectives of the present disclosure, the following technical solutions are applied:

A preparation process of compounds having formula (I) of the present disclosure, comprising the following steps of:

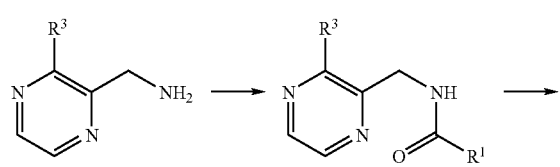

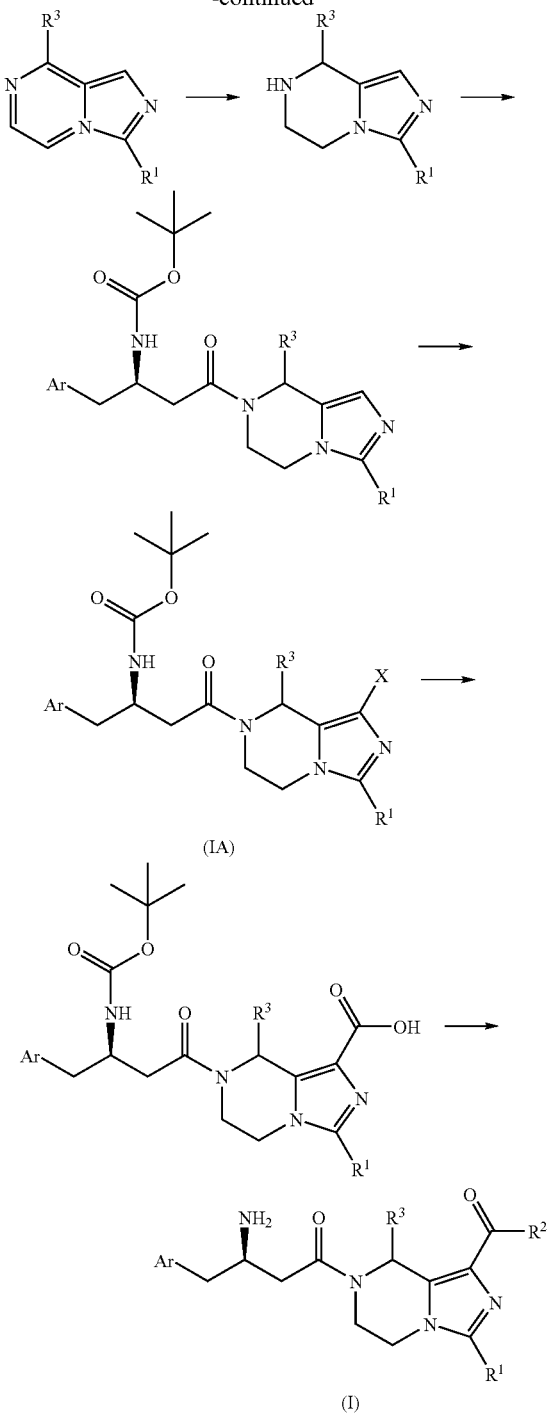

adding dropwise an acid anhydride to the starting material pyrazine 2-methylamine in an ice-water bath and then stirring the reaction mixture at room temperature to obtain an amide product; mixing the amide product and phosphorus oxychloride at room temperature and then adding phosphorous pentoxide to the resulting mixture; allowing the condensation reaction to occur by heating to reflux to obtain the condensation product imidazole[1,5-a]pyrazine derivative; reducing the imidazole[1,5-a]pyrazine derivative in the solvent of ethanol, in the presence of a Pd/C catalyst, with hydrogen to obtain the R$^1$ substituted tetrahydro-imidazo[1,5-a]pyrazine derivative; reacting the R¹ substituted tetrahydro-imidazo[1,5-a]pyrazine derivative in the solvent of dichloromethane with a carboxylic acid in a condensation reaction, in the presence of a condensation reagent bis(2-oxo-3-oxazolidinyl)phosphonic chloride and triethylamine; reacting the resulting condensation product with halogenated succinimide in the solvent of anhydrous ethanol at room temperature to obtain the intermediate having formula (IA); under a carbon monoxide atmosphere, reacting intermediate having formula (IA) with cobalt octacarbonyl and chloracetate in the solvent of methanol in an oil bath and then hydrolyzing the resulting product in the presence of an acid at room temperature to obtain the carboxylic acid; reacting the resulting carboxylic acid with an amine or an alcohol in the presence of a condensation reagent at room temperature or with 1-halogenated carbonate, and then deprotecting the amino protecting group in the presence of an acid to obtain the compound having formula (I).

A preparation process of compounds having formula (I) of the present disclosure, comprising the following steps of nated compound; under a carbon monoxide atmosphere, reacting the resulting halogenated compound with dicobalt octacarbonyl and chloroacetate in the solvent of methanol in an oil bath to obtain the ester substituted tetrahydro-imidazo [1,5-a]pyrazine derivative; hydrolyzing the resulting ester substituted tetrahydro-imidazo[1,5-a]pyrazine derivative in the presence of a base to obtain the carboxylic acid;

reacting the resulting carboxylic acid compound with an haloalkyl in a dry ice-acetone bath to obtain the alkyl substituted product; next, esterifying the carboxyl of the alkyl substituted product to obtain the intermediate having formula (IB); or reacting the resulting carboxylic acid compound with N-methoxyl methylamine in the presence of a condensation reagent bis(2-oxo-3-oxazolidinyl)phosphonic chloride in the solvent of dichloromethane; reacting the resulting condensation compound with a Grignard reagent in the solvent of tetrahydrofuran to obtain the ketone substituted tetrahydro-imidazo[1,5-a]pyrazine derivative; deprotecting the amino

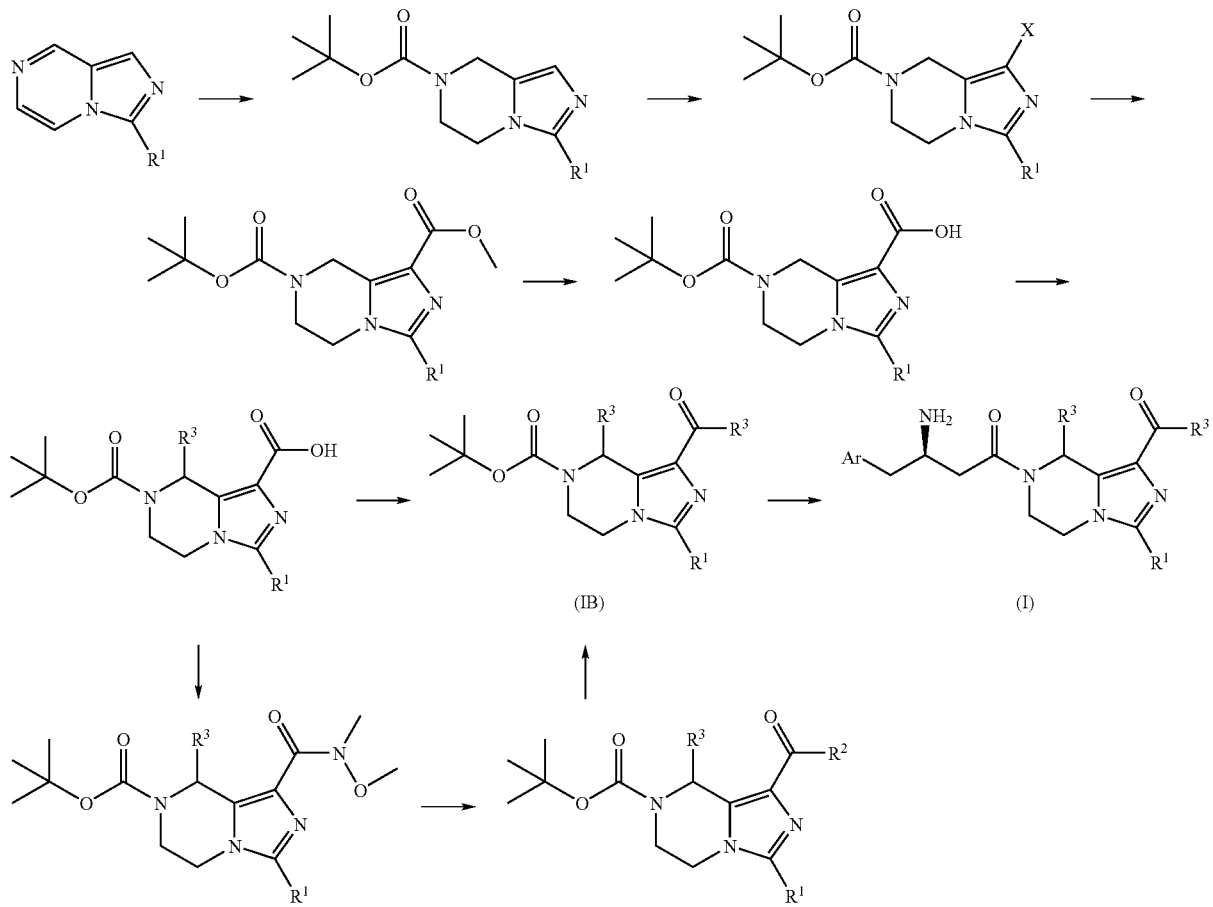

reducing the R¹ substituted imidazole[1,5-a]pyrazine derivative in the solvent of ethanol at room temperature by hydrogenation and then reacting the resulting reduced product with di-tert-butyl dicarbonate in the solvent of ethanol in order to protect the amino group to obtain the amino protected R¹ substituted imidazole[1,5-a]pyrazine derivative; reacting the resulting amino protected R¹ substituted imidazole[1,5-a]pyrazine derivative with halogenated succinimide in the solvent of ethanol at room temperature to obtain the halogenated protecting group from the ketone substituted tetrahydro-imidazo[1,5-a]pyrazine derivative in the presence of an acid to obtain the intermediate having formula (IB); reacting intermediate having formula (IB) with a carboxylic acid in the presence of a condensation reagent bis(2-oxo-3-oxazolidinyl)phosphonic chloride to obtain the condensation product and further deprotecting the amino protecting group in the presence of an acid to obtain the compound having formula (I).

The purified compounds having formula (I) are directly reacted with acids in the solvent of methanol, dichlormethane or ethyl acetate to obtain the acid addition salts.

EXAMPLES

The following examples serve to illustrate the invention, but the examples should not be considered as limiting the scope of the invention.

The compounds' structures were characterized by $^1$H nuclear magnetic resonance spectroscopy (NMR) and mass spectrometry (MS). $^1$H NMR chemical shifts ($\delta$) were given in ppm ($10^{-6}$). $^1$H NMR is determined by a Bruker AVANCE-400 machine. The solvents were deuterated methanol (CD$_3$OD), deuterated chloroform (CDCl$_3$) and deuterated dimethyl sulfoxide (DMSO-d$_6$) with tetramethylsilane (TMS) as an internal standard. Chemical shifts were given in ppm ($10^{-6}$);

MS was determined by a FINNIGAN LCQAd (ESI) mass spectrometer (manufacturer: Therm, type: Finnigan LCQ advantage MAX);

IC$_{50}$ was determined by a NovoStar ELIASA (BMG Co. German);

Thin-layer silica gel was Yantai Huanghai HSGF254 or Qingdao GF254 silica gel plate;

Column chromatography generally used Yantai Huanghai 200-300 mesh silica gel as a carrier;

All examples were performed under nitrogen atmosphere if not otherwise specified.

Nitrogen atmosphere refers to a reaction flask with a balloon filled with 1 L nitrogen.

Hydrogen atmosphere refers to a reaction flask with a balloon filled with 1 L hydrogen.

Example 1

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid methyl ester hydrochloride

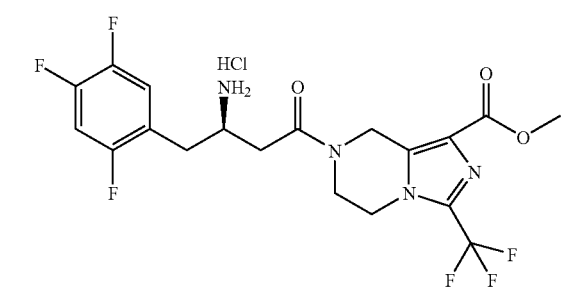

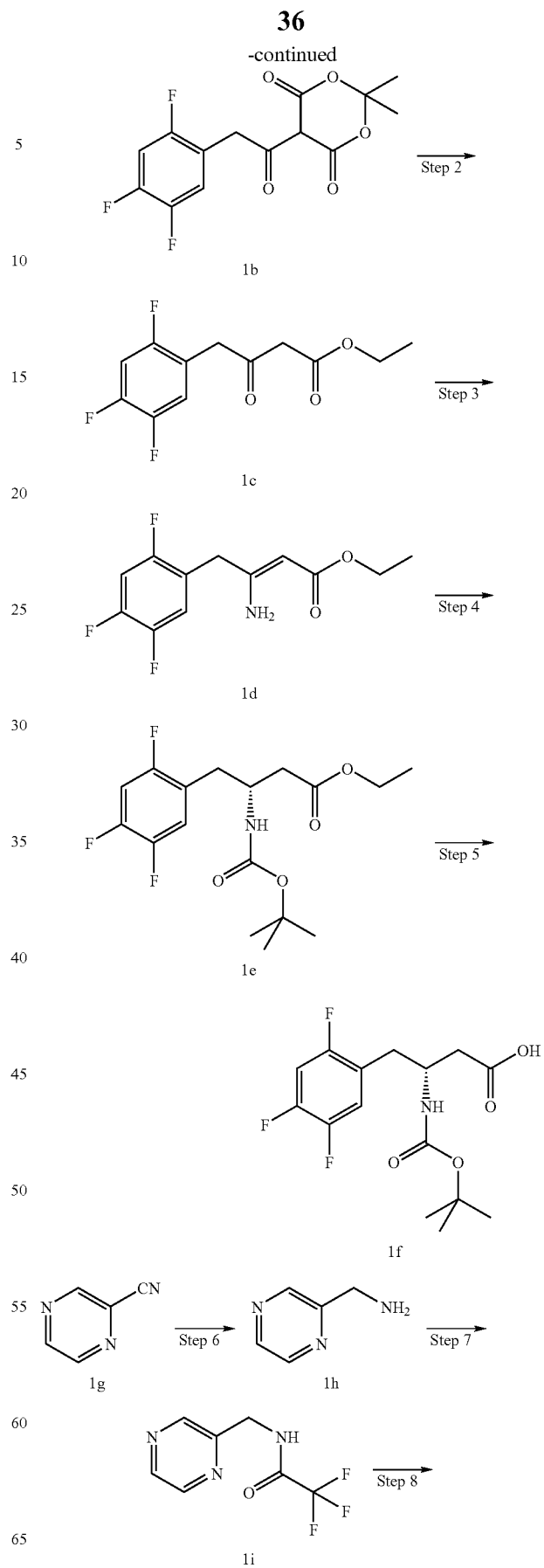

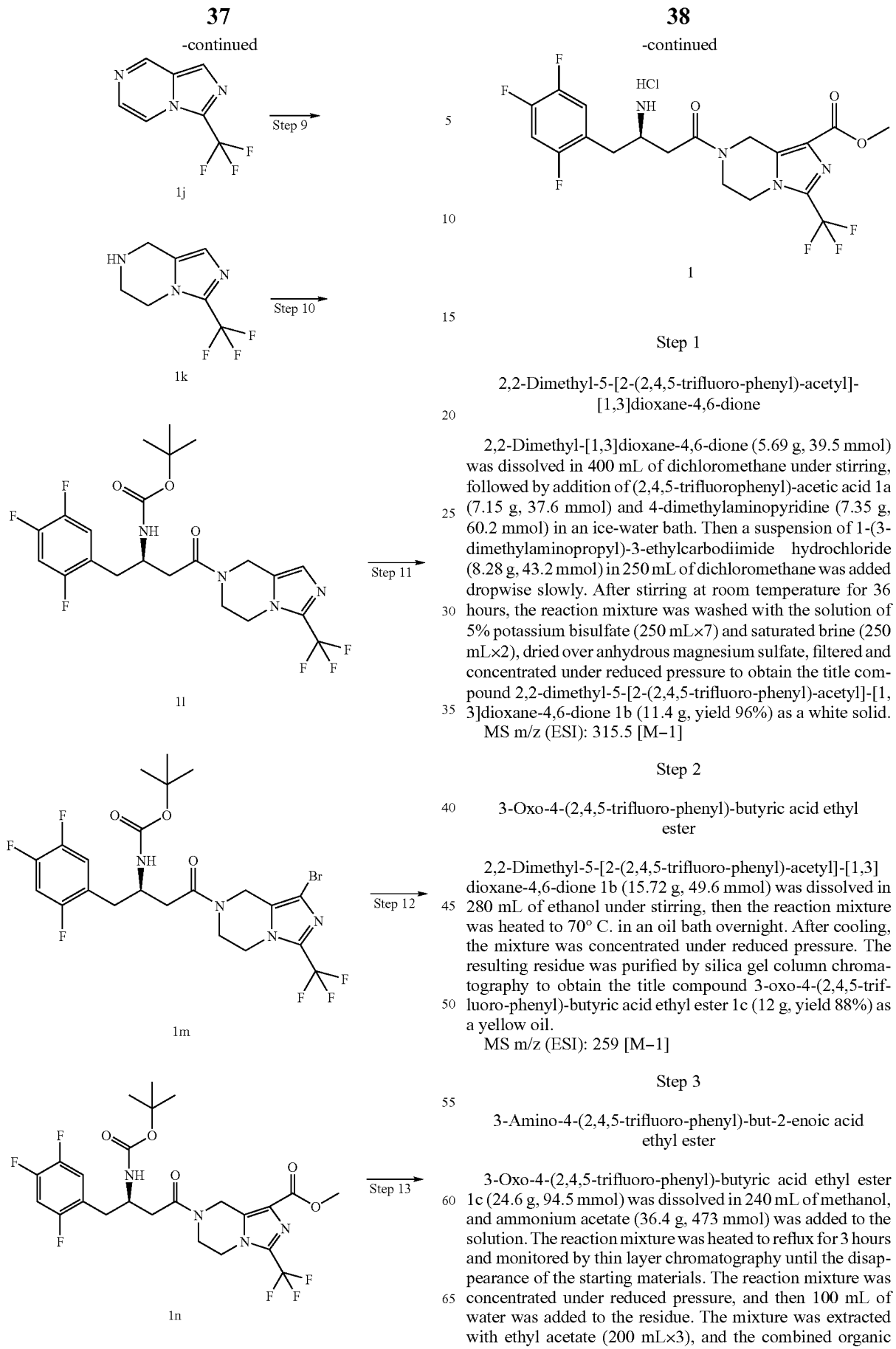

Step 1

2,2-Dimethyl-5-[2-(2,4,5-trifluoro-phenyl)-acetyl]-[1,3]dioxane-4,6-dione 2,2-Dimethyl-[1,3]dioxane-4,6-dione (5.69 g, 39.5 mmol) was dissolved in 400 mL of dichloromethane under stirring, followed by addition of (2,4,5-trifluorophenyl)-acetic acid 1a (7.15 g, 37.6 mmol) and 4-dimethylaminopyridine (7.35 g, 60.2 mmol) in an ice-water bath. Then a suspension of 1-(3-dimethylaminopropyl)-3-ethylcarbodiimide hydrochloride (8.28 g, 43.2 mmol) in 250 mL of dichloromethane was added dropwise slowly. After stirring at room temperature for 36 hours, the reaction mixture was washed with the solution of 5% potassium bisulfate (250 mL×7) and saturated brine (250 mL×2), dried over anhydrous magnesium sulfate, filtered and concentrated under reduced pressure to obtain the title compound 2,2-dimethyl-5-[2-(2,4,5-trifluoro-phenyl)-acetyl]-[1,3]dioxane-4,6-dione 1b (11.4 g, yield 96%) as a white solid.

MS m/z (ESI): 315.5 [M−1]

Step 2

3-Oxo-4-(2,4,5-trifluoro-phenyl)-butyric acid ethyl ester 2,2-Dimethyl-5-[2-(2,4,5-trifluoro-phenyl)-acetyl]-[1,3]dioxane-4,6-dione 1b (15.72 g, 49.6 mmol) was dissolved in 280 mL of ethanol under stirring, then the reaction mixture was heated to 70° C. in an oil bath overnight. After cooling, the mixture was concentrated under reduced pressure. The resulting residue was purified by silica gel column chromatography to obtain the title compound 3-oxo-4-(2,4,5-trifluoro-phenyl)-butyric acid ethyl ester 1c (12 g, yield 88%) as a yellow oil.

MS m/z (ESI): 259 [M−1]

Step 3

3-Amino-4-(2,4,5-trifluoro-phenyl)-but-2-enoic acid ethyl ester

3-Oxo-4-(2,4,5-trifluoro-phenyl)-butyric acid ethyl ester 1c (24.6 g, 94.5 mmol) was dissolved in 240 mL of methanol, and ammonium acetate (36.4 g, 473 mmol) was added to the solution. The reaction mixture was heated to reflux for 3 hours and monitored by thin layer chromatography until the disappearance of the starting materials. The reaction mixture was concentrated under reduced pressure, and then 100 mL of water was added to the residue. The mixture was extracted with ethyl acetate (200 mL×3), and the combined organic phase was washed with 200 mL of saturated brine, dried over anhydrous magnesium sulfate, filtered and concentrated under reduced pressure to obtain a light yellow solid. The resulting solid was dissolved in 50 mL of ethyl acetate at 80° C., and then 50 mL of n-hexane and seed-crystal were added to the solution. The mixture was cooled to room temperature, and, half an hour later, 100 mL of n-hexane was added. The mixture was stored in refrigerator overnight and then filtered under reduced pressure to obtain the title compound 3-amino-4-(2,4,5-trifluoro-phenyl)-but-2-enoic acid ethyl ester 1d (19.5 g, yield 80%) as a white solid.

MS m/z (ESI): 260.1 [M+1]

Step 4

(R)-3-tert-Butoxycarbonylamino-4-(2,4,5-trifluoro-phenyl)-butyric acid ethyl ester 3-Amino-4-(2,4,5-trifluoro-phenyl)-but-2-enoic acid ethyl ester 1d (4.1 g, 15.8 mmol) was added into an autoclave, followed by addition of 70 mL of methanol, di-tert-butyl dicarbonate (3.8 g, 17.4 mmol), chloro(1,5-cyclooctadiene)rhodium(I) dimer (32 mg, 0.0632 mmol) and (R)-1-[(S)-2-(diphenyl phosphino)ferrocenyl]-ethyl-tert-butylphosphine (68 mg, 0.126 mmol). The reaction mixture was hydrogenated for 24 hours under 6.67 atmosphere at 30° C. The mixture was filtered and the filtrate was concentrated under reduced pressure. Then 34 mL of methanol was added to the residue at 50° C., followed by addition of 12 mL of water until all dissolved. After cooling to room temperature, the mixture was stored in the refrigeratory overnight and then filtered. The solid product was washed with the solvent mixture of methanol/water (v:v=3:2), dried in vacuo to obtain the title compound (R)-3-tert-butoxycarbonylamino-4-(2,4,5-trifluoro-phenyl)-butyric acid ethyl ester 1e (4 g, yield 70%) as a light yellow solid.

MS m/z (ESI): 362.4 [M+1]

Step 5

(R)-3-tert-Butoxycarbonylamino-4-(2,4,5-trifluoro-phenyl)-butyric acid (R)-3-tert-Butoxycarbonylamino-4-(2,4,5-trifluoro-phenyl)-butyric acid ethyl ester 1e (10 g, 27.7 mmol) and sodium hydroxide (3.32 g, 83.1 mmol) were dissolved in the solvent mixture of 100 mL of methanol and 50 mL of water under stirring. The reaction mixture was reacted at 40-45° C. for 1-1.5 hours, then part of the solution was evaporated under reduced pressure. The residue was added with some water, then pH was adjusted to 2-3 with 1 N hydrochloric acid in an ice-water bath. The mixture was extracted with ethyl acetate (200 mL×3), and the combined organic phase was washed with 200 mL of saturated brine, dried over anhydrous sodium sulfate, filtered and concentrated under reduced pressure, and then recrystallized from ethyl acetate/n-hexane to obtain the title compound (R)-3-tert-butoxycarbonylamino-4-(2,4,5-trifluoro-phenyl)-butyric acid 1f (9.2 g) as a white solid, which was directly used in the next step.

MS m/z (ESI): 332.3 [M−1]

Reference: *Tetrahedron Asymmetry*, 2006, 17(2), 205-209

Step 6

C-Pyrazin-2-yl-methylamine

Pyrazine-2-carbonitrile 1g (10.5 g, 100 mmol) was dissolved in 150 mL of 1,4-dioxane under stirring, then Raney nickel (1.0 g) was added into a 250 mL autoclave. The reaction mixture was hydrogenated for 8 hours under 40 atmosphere at 60° C., filtered and concentrated under reduced pressure to obtain the title compound C-pyrazin-2-yl-methylamine 1h (10.7 g, yield 98%) as a brown oil.

MS m/z (ESI): 110 [M+1]

Step 7

2,2,2-Trifluoro-N-pyrazin-2-ylmethyl-acetamide

C-Pyrazin-2-yl-methylamine 1h (10.9 g, 100 mmol) was added into a reaction flask, then 20 mL of trifluoroacetic anhydride was added dropwise slowly within an hour at 0° C. in an ice-water bath. The reaction mixture was reacted at room temperature for 2 hours and monitored by thin layer chromatography until the disappearance of the starting materials. Then it was concentrated under reduced pressure. The resulting residue was purified by silica gel column chromatography to obtain the title compound 2,2,2-trifluoro-N-pyrazin-2-ylmethyl-acetamide 1i (21.0 g) as a brown oil.

MS m/z (ESI): 206.1 [M+1]

Step 8

3-Trifluoromethyl-imidazo[1,5-a]pyrazine 2,2,2-Trifluoro-N-pyrazin-2-ylmethyl-acetamide 1i (21.0 g, 100 mmol) was added into a reaction flask at room temperature, followed by addition of 100 mL of phosphorus oxychloride. After stirring at room temperature for 30 minutes, phosphorous pentoxide (17.8 g, 125 mmol) was added to the solution. The reaction mixture was heated to reflux for 5 hours and monitored by thin layer chromatography until the disappearance of the starting materials. Phosphorus oxychloride was removed, and the reaction system was quenched with deionized water. The mixture was adjusted to pH 5-6 with 20% sodium hydroxide solution in an ice-water bath. The mixture was extracted with ethyl acetate (250 mL×4), and the combined organic phase was dried over anhydrous magnesium sulfate, filtered and concentrated under reduced pressure. The resulting residue was purified by silica gel column chromatography to obtain the title compound 3-trifluoromethyl-imidazo[1,5-a]pyrazine 1j (12.0 g, yield 65%) as a yellow solid.

MS m/z (ESI): 188.0 [M+1]

$^1$H NMR (400 MHz, CDCl$_3$): δ 9.15 (s, 1H), 8.06 (d, 1H), 7.92 (s, 1H), 7.81 (d, 1H)

Step 9

3-Trifluoromethyl-5,6,7,8-tetrahydro-imidazo[1,5-a]pyrazine

3-Trifluoromethyl-imidazo[1,5-a]pyrazine 1j (12.0 g, 64.2 mmol) was dissolved in 150 mL of anhydrous ethanol under stirring, then 10% Pd/C (500 mg) was added to the solution. The reaction mixture was stirred at room temperature under a hydrogen atmosphere overnight. The reaction solution was filtered through a pad of coarse silica gel and concentrated under reduced pressure to obtain the title compound 3-trifluoromethyl-5,6,7,8-tetrahydro-imidazo[1,5-a]pyrazine 1k (12.2 g, yield 99%) as a brown solid.

$^1$H NMR (400 MHz, CDCl$_3$): δ 6.84 (s, 1H), 4.10 (m, 4H), 3.26 (m, 2H), 1.81 (s, 1H)

Step 10

(R)-[3-oxo-1-(2,4,5-trifluoro-benzyl)-3-(3-trifluoromethyl-5,6-dihydro-8H-imidazo[1,5-a]pyrazin-7-yl)-propyl]-carbamic acid tert-butyl ester Under a nitrogen atmosphere, 3-tert-butoxycarbonylamino-4-(2,4,5-trifluoro-phenyl)-butyric acid 1k (8.6 g, 45 mmol) and 9.4 mL of triethylamine were dissolved in 300 mL of dichloromethane under stirring. After stirring at room temperature for 5 minutes, 3-trifluoromethyl-5,6,7,8-tetrahydroimidazo[1,5-a]pyrazine if (15.0 g, 45 mmol) and bis(2-oxo-3-oxazolidinyl)phosphonic chloride (17.1 g, 67.3 mmol) were added to the solution successively. The reaction mixture was reacted at room temperature for 2 hours and monitored by thin layer chromatography until the disappearance of the starting materials and then concentrated under reduced pressure. The resulting residue was purified by silica gel column chromatography to obtain the title compound (R-[3-oxo-1-(2,4,5-trifluoro-benzyl)-3-(3-trifluoromethyl-5,6-dihydro-8H-imidazo[1,5-a]pyrazin-7-yl)-propyl]carbamic acid tert-butyl ester 1l (20.0 g, yield 88%) as a white solid.

$^1$H NMR (400 MHz, CD$_3$OD): δ 7.25 (m, 1H), 7.11 (m, 1H), 7.032 (s, 1H), 4.93 (m, 2H), 4.35 (m, 3H), 4.05 (m, 2H), 2.99 (m, 2H), 2.73 (m, 2H), 1.34 (s, 9H)

Step 11

(R)-[3-(1-Bromo-3-trifluoromethyl-5,6-dihydro-8H-imidazo[1,5-a]pyrazin-7-yl)-3-oxo-1-(2,4,5-trifluoro-benzyl)-propyl]carbamic acid tert-butyl ester (R)-[3-oxo-1-(2,4,5-trifluoro-benzyl)-3-(3-trifluoromethyl-5,6-dihydro-8H-imidazo[1,5-a]pyrazin-7-yl)-propyl]-carbamic acid tert-butyl ester 1l (20.0 g, 39.6 mmol) was dissolved in 300 mL of anhydrous ethanol under stirring, and 1-bromo-2,5-pyrrolidinedione (14.1 g, 79.2 mmol) was then added to the solution at room temperature. After stirring for an hour, potassium carbonate (10.9 g, 79.2 mmol) and di-tert-butyl dicarbonate (8.6 g, 39.6 mmol) were added to the mixture, and the mixture was stirred for an hour and monitored by thin layer chromatography until the disappearance of the starting materials. The reaction mixture was filtered through a pad of coarse silica gel to remove potassium carbonate, and then concentrated under reduced pressure. The resulting residue was purified by silica gel column chromatography to obtain the title compound (R)-[3-oxo-1-(2,4,5-trifluoro-benzyl)-3-(1-bromo-3-trifluoromethyl-5,6-dihydro-8H-imidazo[1,5-a]pyrazin-7-yl)-propyl]-carbamic acid tert-butyl ester 1m (20.0 g, yield 86%) as a white solid.

$^1$H NMR (400 MHz, CDCl$_3$): δ 7.063 (m, 1H), 6.88 (m, 1H), 4.72 (s, 1H), 4.56 (s, 1H), 4.13 (m, 3H), 3.88 (m, 2H), 2.94 (m, 2H), 2.62 (m, 2H), 1.36 (s, 9H)

Step 12

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester Octacarbonyldicobalt (4.02 g, 11.76 mmol), ethyl chloroacetate (0.71 g, 5.88 mmol), potassium carbonate (1.62 g, 11.76 mmol) and 50 mL of methanol were added into the reaction flask. After stirring for 5 minutes, (R)—[3-oxo-1-(2, 4,5-trifluoro-benzyl)-3-(1-bromo-3-trifluoromethyl-5,6-dihydro-8H-imidazo[1,5-a]pyrazin-7-yl)-propyl]-carbamic acid tert-butyl ester 1m (2.3 g, 3.92 mmol) was added. The reaction mixture was reacted at 60° C. in an oil bath, and the colour of the reaction mixture turned from puce to purple. 2 hours later, Electro-Spray Ionization (ESI) mass spectrometry showed the starting material disappeared. The reaction mixture was concentrated under reduced pressure. The resulting residue was purified by silica gel column chromatography to obtain the title compound (R)-7-[3-tert-butoxy-carbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester 1n (1.1 g, yield 50%) as a white solid.

MS m/z (ESI): 565.0 [M+1]

Reference: *Journal of Organometallic Chemistry*, 1985, 285(1-3), 293-303

Step 13

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid methyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester 1n (0.12 g, 2.12 mmol) was added to a solution of 2.2 N hydrochloric acid in 5 mL of ethyl acetate. The reaction mixture was reacted at room temperature for 5 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester hydrochloride 1 (0.12 g, yield 94.3%) as a light yellow solid.

MS m/z (ESI): 465.2 [M+1]

$^1$H NMR (400 MHz, CD$_3$OD): δ 7.101-7.08 (m, 1H), 6.906-6.864 (m, 1H), 5.343-4.995 (m, 2H), 4.221-4.093 (m, 5H), 3.954 (s, 3H), 2.978-2.937 (m, 2H), 2.71-2.643 (m, 2H), 2.061 (s, 2H)

Example 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (2-methanesulfonyl-ethyl)-amide hydrochloride

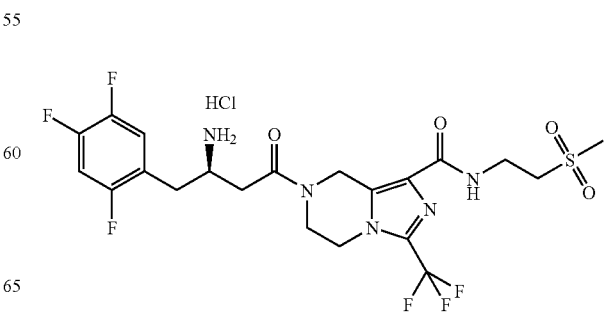

-continued

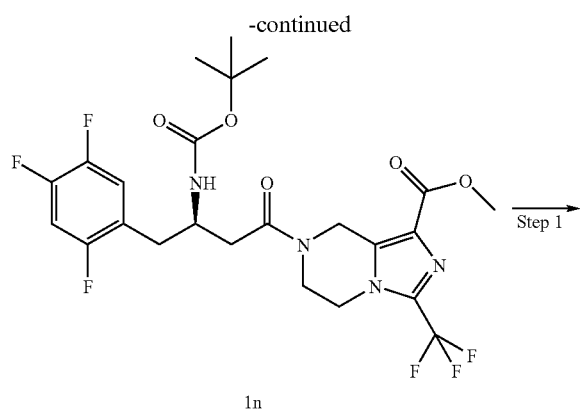

1n

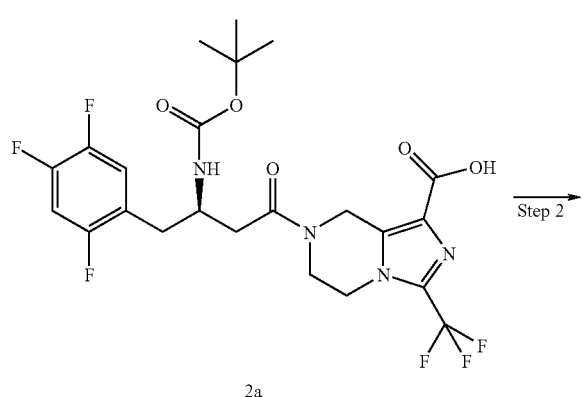

2a

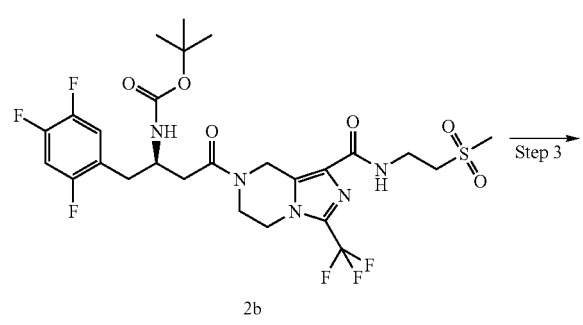

2b

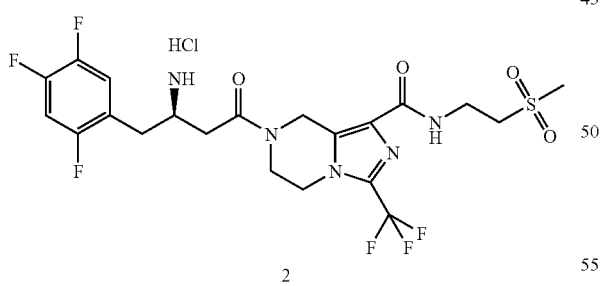

2

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester 1n (2.0 g, 3.5 mmol) was dissolved in 50 mL of methanol under stirring, and 4 N sodium hydroxide solution (30 mL) was added to the solution. The reaction mixture was reacted at room temperature for an hour until thin lay chromatography showed the starting material disappeared, and was adjusted to pH 3 with a 2 N hydrochloric acid solution. The reaction mixture was extracted with ethyl acetate (50 mL×4), and the combined organic phase was dried over anhydrous magnesium sulfate, filtered, and concentrated under reduced pressure to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (1.9 g) as a light yellow solid.

$^1$H NMR (400 MHz, CD$_3$OD): δ 7.29-7.226 (m, 1H), 7.121-7.082 (m, 1H), 5.151-5.028 (m, 2H), 4.409-4.064 (m, 5H), 2.984-2.769 (m, 4H), 1.417-1.255 (m, 9H)

Step 2

(R)-[3-[1-(2-Methanesulfonyl-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), 2-methanesulfonyl-ethylamine (65.5 mg, 0.41 mmol) and bis (2-oxo-3-oxazolidinyl)phosphonic chloride (0.104 g, 0.41 mmol) were dissolved in 5 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(2-methanesulfonyl-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 2b (60 mg, yield 34%) as a white solid.

MS m/z (ESI): 678.2 [M+23]

Reference: *Journal of Organic Chemistry*, 2006, 71(3), 1220-1225

Step 3

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (2-methanesulfonyl-ethyl)-amide hydrochloride (R)-[3-[1-(2-Methanesulfonyl-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 2b (0.06 g, 0.091 mmol) was dissolved in a little ethyl acetate. A solution of 3.1 N hydrochloric acid in 4 mL of ethyl acetate was then added to the solution. The reaction mixture was reacted at room temperature for 4 hours until thin lay chromatography showed the starting material disappeared, and was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (2-methanesulfonyl-ethyl)-amide hydrochloride 2 (60 mg) as a white solid.

MS m/z (ESI): 556.3 [M+1].

$^1$H NMR (400 MHz, CD$_3$OD): δ7.44-7.35 (m, 1H), 7.30-7.21 (m, 1H), 5.15-5.02 (m, 2H), 4.53-4.45 (m, 2H), 4.34-4.27 (m, 2H), 4.05-3.94 (m, 4H), 3.89-3.62 (s, 4H), 3.12-3.07 (m, 2H), 3.03-2.82 (m, 2H).

Example 3

(R)-3-Amino-1-[1-(morpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride

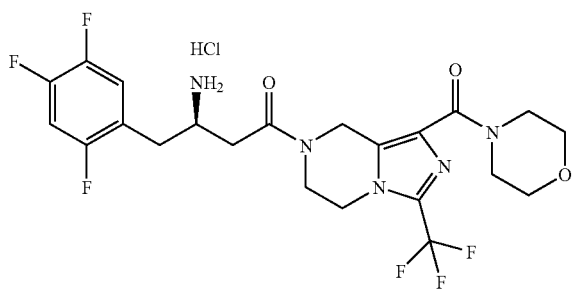

2a

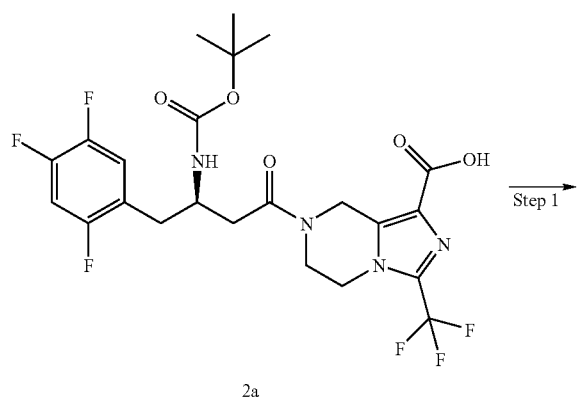

3a

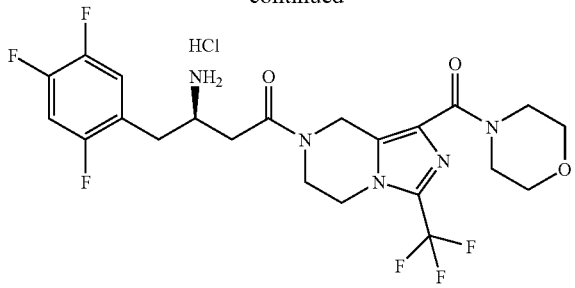

3

Step 1

(R)-[3-[1-(Morpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (60 mg, 0.109 mmol), morpholine (19 mg, 0.218 mmol) and bis(2-oxo-3-oxazolidinyl) phosphonic chloride (53.5 mg, 0.218 mmol) were dissolved in 5 mL of dichloromethane under stirring, and triethylamine (0.1 mL, 0.65 mmol) was then added to the solution. The reaction mixture was reacted at room temperature overnight until thin lay chromatography showed the starting material disappeared, and was concentrated under reduced pressure. The resulting residue was purified by silica gel column chromatography to obtain the title compound (R)-[3-[1-(morpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 3a (60 mg, yield 89%) as a white solid.

MS m/z (ESI): 620.0 [M+1].

Step 2

(R)-3-Amino-1-[1-(morpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-(Morpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 3a (0.07 g, 0.11 mmol) was dissolved in a little ethyl acetate. A solution of 3.1N hydrochloric acid in 6 mL of ethyl acetate was then added to the solution. The reaction mixture was reacted at room temperature for 4 hours and monitored by thin layer chromatography until the disappearance of the starting materials. The reaction mixture was concentrated under reduced pressure to obtain the title compound (R)-3-amino-1-[1-(morpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride 3 (70 mg) as a light yellow solid.

MS m/z (ESI): 520.2 [M+1].

$^1$H NMR (400 MHz, CD$_3$OD): δ7.42-7.37 (m, 1H), 7.26-7.22 (m, 1H), 5.15-5.05 (m, 2H), 4.53-4.44 (m, 2H), 4.34-4.26 (m, 2H), 4.02-3.94 (m, 4H), 3.89-3.84 (m, 1H), 3.76-3.61 (m, 4H), 3.11-3.06 (m, 2H), 3.05-2.83 (m, 2H).

Example 4

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid cyanomethyl-amide hydrochloride

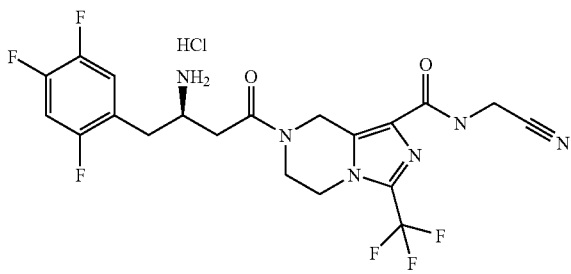

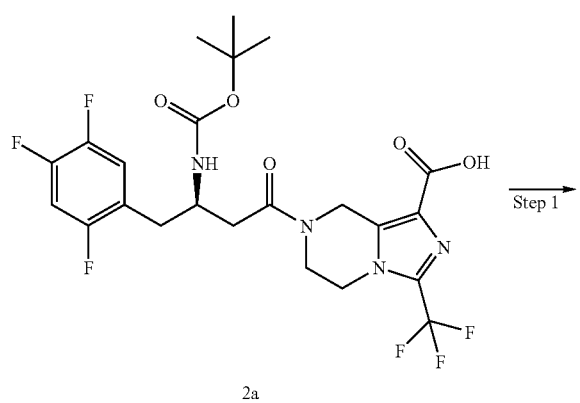

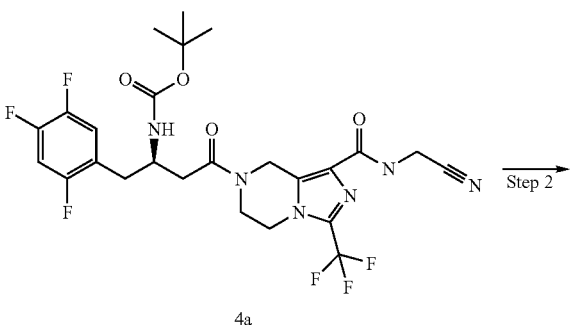

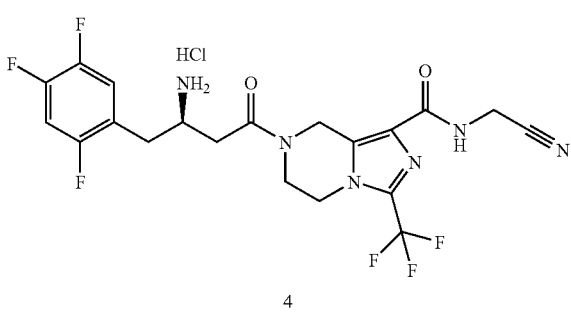

Step 1

(R)-[3-[1-(Cyanomethyl-carbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), aminoacetonitrile sulfate (85 mg, 0.41 mmol), bis(2-oxo-3-oxazolidinyl)phosphonic chloride (0.206 g, 0.81 mmol) and triethylamine (0.37 mL, 2.7 mmol) were dissolved in 10 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(cyanomethyl-carbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 4a (150 mg, yield 94.4%) as a white solid.

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid cyanomethyl-amide hydrochloride (R)-[3-[1-(Cyanomethyl-carbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 4a (0.3 g, 0.25 mmol) was dissolved in 10 mL of dichloromethane, and 5 mL of trifluoroacetic acid was then added to the solution. The reaction mixture was reacted at room temperature for 1 hour until thin lay chromatography showed the starting material disappeared. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid cyanomethyl-amide hydrochloride 4 (130 mg) as a light yellow solid.

MS m/z (ESI): 489.2 [M+1].

Example 5

(R)-3-Amino-1-[1-(4-methyl-piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride

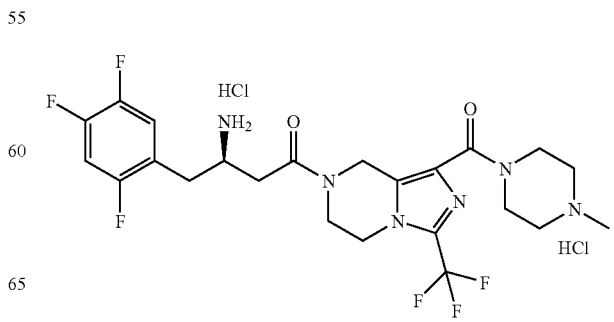

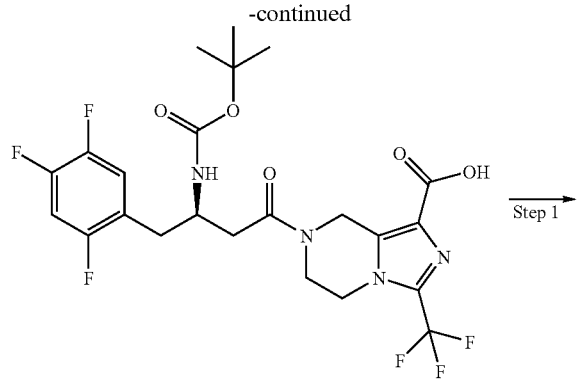

2a

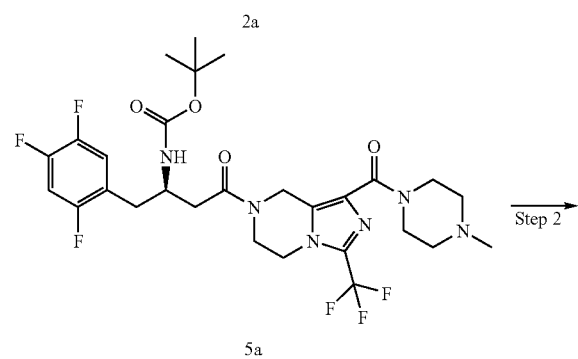

5a

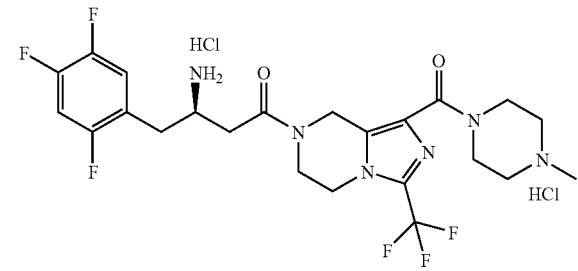

5

Step 1

(R)-[3-[1-(4-Methyl-piperazine-1-carbonyl)-3-trifluoromethyl-5,6-dihydro-8H imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), 1-methylpiperazine (54 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(4-methyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 5a (80 mg, yield 49%) as a white solid.

MS m/z (ESI): 633.2 [M+1].

Step 2

(R)-3-Amino-1-[1-(4-methyl-piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride (R)-[3-[1-(4-Methyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 5a (0.08 g, 0.126 mmol) was dissolved in a solution of 3.1 N hydrochloric acid in 6 mL of ethyl acetate. The reaction mixture was reacted at room temperature overnight and monitored by thin layer chromatography until the disappearance of the starting materials. The reaction mixture was concentrated under reduced pressure to obtain the title compound (R)-3-amino-1-[1-(4-methyl-piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride 5 (90 mg) as a white solid.

MS m/z (ESI): 533.2 [M+1].

$^1$H NMR (400 MHz, CD$_3$OD): δ7.45-7.38 (m, 1H), 7.27-7.23 (m, 1H), 5.10-5.05 (m, 2H), 4.35-4.28 (m, 2H), 4.10-4.09 (m, 1H), 4.00-3.95 (m, 2H), 3.68-3.56 (m, 4H), 3.35-3.24 (m, 4H), 3.13 (m, 2H), 3.00-2.88 (m, 5H).

Example 6

(R)-3-Amino-1-[1-(1,1-dioxo-thiomorpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride

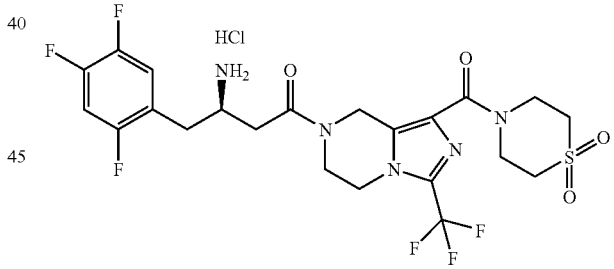

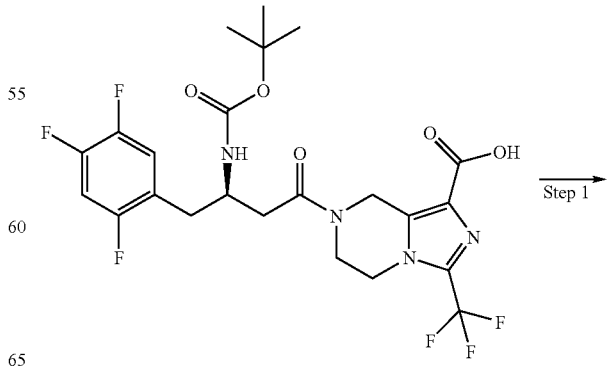

2a

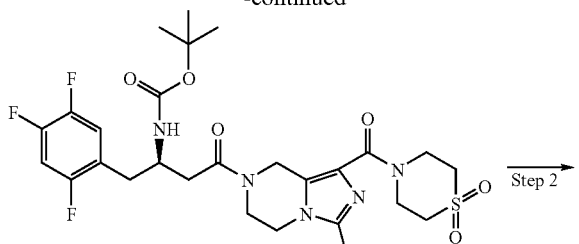

6a

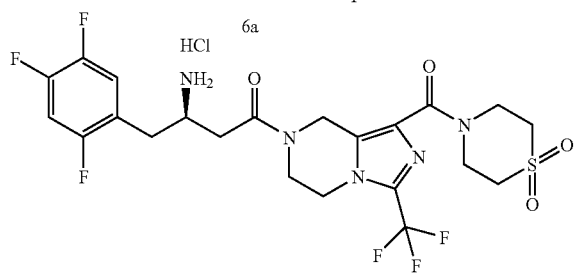

6

Step 1

(R)-[3-[1-(1,1-Dioxo-thiomorpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), thiomorpholine-1,1-dioxide hydrochloride (73 mg, 0.54 mmol), bis(2-oxo-3-oxazolidinyl)phosphonic chloride (0.138 g, 0.54 mmol) and triethylamine (0.25 mL, 1.62 mmol) were dissolved in 8 mL of dichloromethane under stirring, and 4 mL of N,N-dimethylformamide was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(1,1-dioxo-thiomorpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 6a (170 mg, yield 94%) as a white solid.

MS m/z (ESI): 668.1 [M+1].

Step 2

(R)-3-Amino-1-[1-(1,1-dioxo-thiomorpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-(1,1-Dioxo-thiomorpholine-4-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 6a (0.15 g, 0.22 mmol) was dissolved in a solution of 3.1 N hydrochloric acid in 4 mL of ethyl acetate. The reaction mixture was reacted at room temperature overnight and monitored by thin layer chromatography until the disappearance of the starting materials. The reaction mixture was concentrated under reduced pressure to obtain the title compound (R)-3-amino-1-[1-(1,1-dioxo-thiomorpholine-4-carbonyl)-3-trifluoromethyl-5,6-dihydro-8H-imidazo[1,5-a]pyrazin-7-yl]-4-(2,4,5-trifluoro-phenyl)-butan-1-one hydrochloride 6 (140 mg) as a light yellow solid.

MS m/z (ESI): 568.2 [M+1].

$^1$H NMR (400 MHz, CD$_3$OD): δ7.45-7.39 (m, 1H), 7.29-7.20 (m, 1H), 5.10-5.04 (m, 2H), 4.35-4.28 (m, 2H), 4.16-4.09 (m, 2H), 4.02-3.93 (m, 5H), 3.27-3.13 (m, 4H), 3.18-3.04 (m, 2H), 2.99-2.85 (m, 2H).

Example 7

(R)-1-{7-[3-Amino-4-(2,4,5-trifluoro-phenyl)-butyryl]-3-trifluoromethyl-5,6,7,8-tetrahydro-imidazo[1,5-a]pyrazine-1-carbonyl}-piperidine-4-carboxylic acid amide hydrochloride

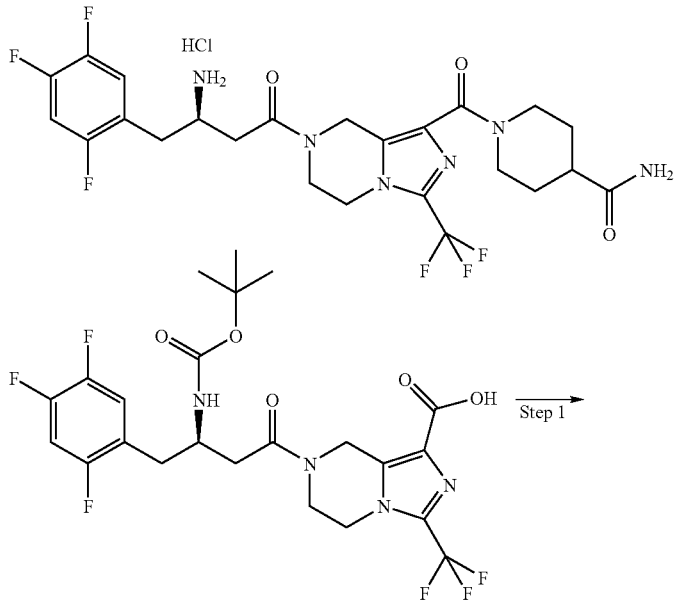

2a

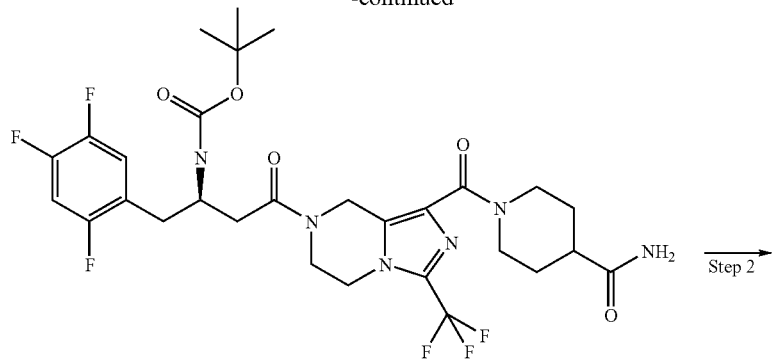

7a

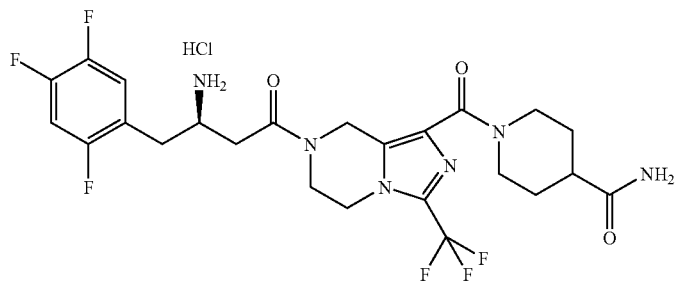

7

Step 1

(R)-[3-[1-(4-Carbamoyl-piperidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), piperidine-4-carboxylic acid amide (70 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) and 4 mL of N,N-dimethylformamide were then added to the solution successively. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(4-carbamoyl-piperidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 7a (180 mg, yield 98%) as a white solid.

MS m/z (ESI): 660.9 [M+1].

Step 2

(R)-1-{7-[3-Amino-4-(2,4,5-trifluoro-phenyl)-butyryl]-3-trifluoromethyl-5,6,7,8-tetrahydro-imidazo[1,5-a]pyrazine-1-carbonyl}-piperidine-4-carboxylic acid amide hydrochloride (R)-[3-[1-(4-Carbamoyl-piperidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 7a (0.18 g, 0.27 mmol) and 2 mL of ethyl acetate were added into the reaction flask. A solution of 2.3 N hydrochloric acid in 6 mL of ethyl acetate was then added to the flask. The reaction mixture was reacted at room temperature for 3.5 hours and monitored by thin layer chromatography until the disappearance of the starting materials. The reaction mixture was concentrated under reduced pressure to obtain the title compound (R)-1-{7-[3-amino-4-(2,4,5-trifluorophenyl)-butyryl]-3-trifluoromethyl-5,6,7,8-tetrahydro-imidazo[1,5-a]pyrazine-1-carbonyl}-piperidine-4-carboxylic acid amide hydrochloride 7 (0.12 g, yield 74%) as a white solid.

MS m/z (ESI): 561.2 [M+1].
$^1$H NMR (400 MHz, CD$_3$OD): δ7.42-7.31 (m, 1H), 7.28-7.16 (m, 1H), 5.17-4.97 (m, 2H), 4.43-4.24 (m, 2H), 4.20-4.03 (m, 1H), 4.03-3.89 (m, 2H), 3.30-3.18 (m, 2H), 3.17-3.06 (m, 2H), 3.03-2.72 (m, 4H), 2.65-2.53 (m, 1H), 2.15-2.03 (m, 2H), 1.93-1.83 (m, 2H), 1.77-1.60 (m, 2H).

Example 8

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid methylamide hydrochloride

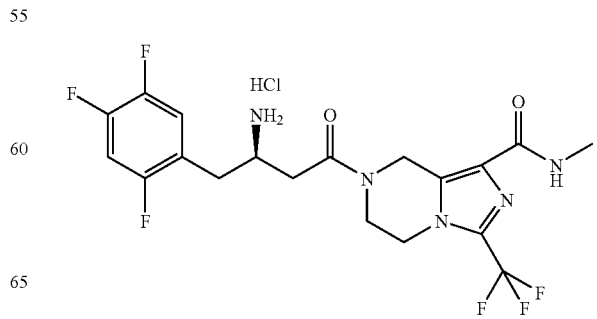

-continued

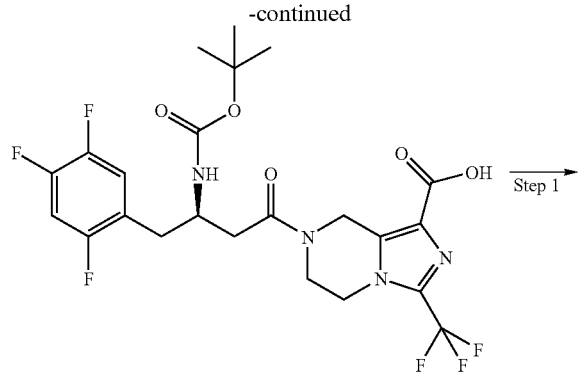

2a

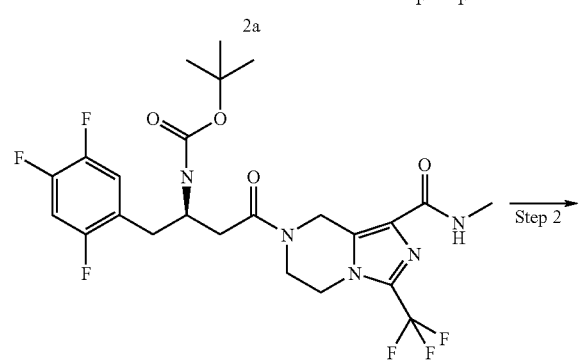

8a

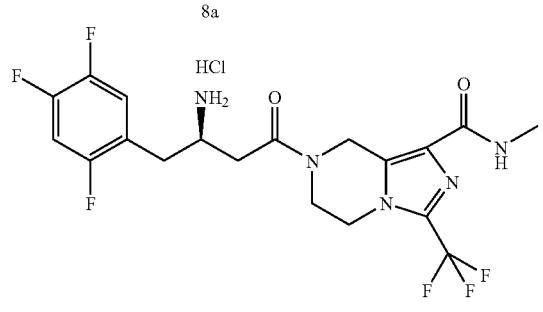

8

Step 1

(R)-[3-(1-Methylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), methylamine hydrochloride (36.5 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-(1-methylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 8a (150 mg, yield 98.6%) as a white solid.

MS m/z (ESI): 563.9 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid methylamide hydrochloride (R)-[3-(1-Methylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 8a (0.15 g, 0.27 mmol) and 2 mL of ethyl acetate were added into the reaction flask. A solution of 2.3 N hydrochloric acid in 5 mL of ethyl acetate was then added to the flask. The reaction mixture was reacted at room temperature for 4 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methylamide hydrochloride 8 (0.135 g, yield 90%) as a white solid.

MS m/z (ESI): 464.2 [M+1].

$^1$H NMR (400 MHz, CD$_3$OD): δ7.40-7.38 (m, 1H), 7.23 (m, 1H), 5.13-5.04 (m, 2H), 4.31-4.25 (m, 2H), 4.07 (m, 1H), 3.96 (m, 2H), 3.10 (m, 2H), 2.99-2.76 (m, 5H).

Example 9

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid dimethylamide hydrochloride

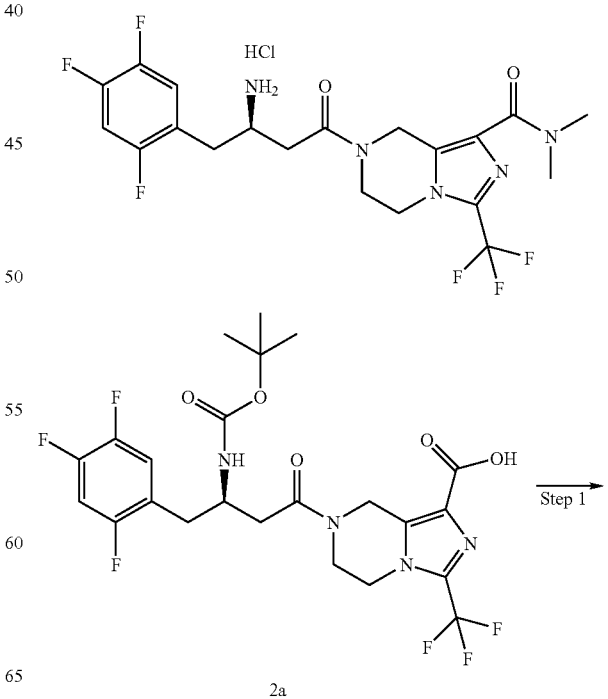

2a

-continued

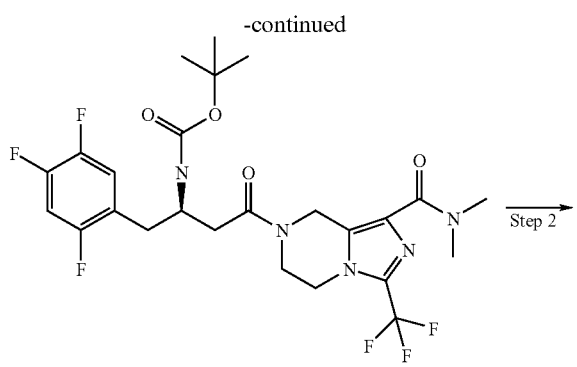

9a

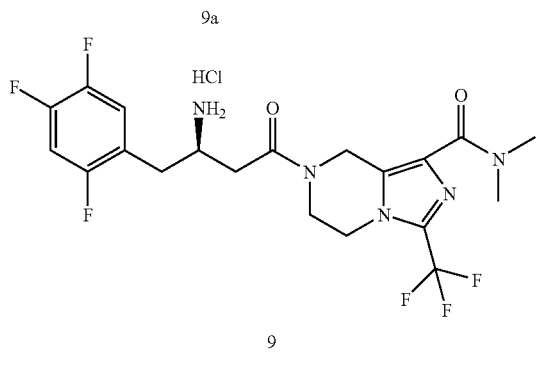

9

Step 1

(R)-[3-(1-Dimethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), dimethylamine hydrochloride (44 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-(1-dimethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 9a (120 mg, yield 77%) as a white solid.

MS m/z (ESI): 578.1 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid dimethylamide hydrochloride (R)-[3-(1-Dimethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 9a (0.138 g, 0.245 mmol) and 2 mL of ethyl acetate were added into the reaction flask. A solution of 2.3 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid dimethylamide hydrochloride 9 (0.12 g, yield 98%) as a white solid.

MS m/z (ESI): 478.2 [M+1].

Example 10

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid hydrochloride

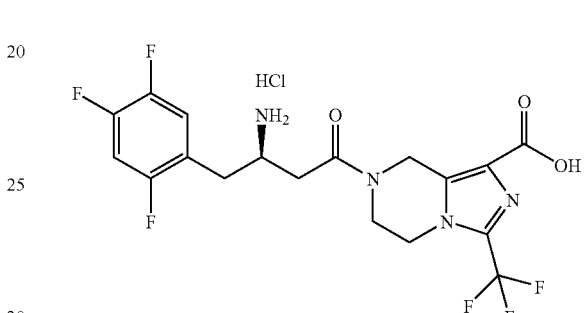

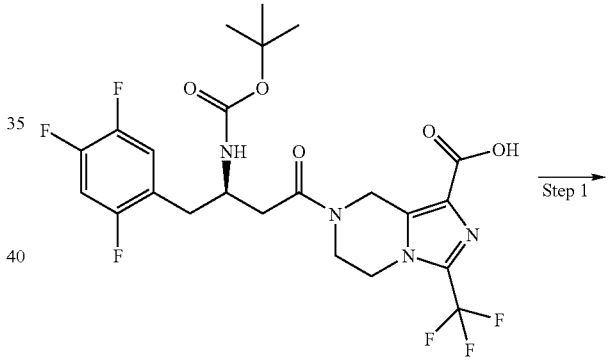

2a

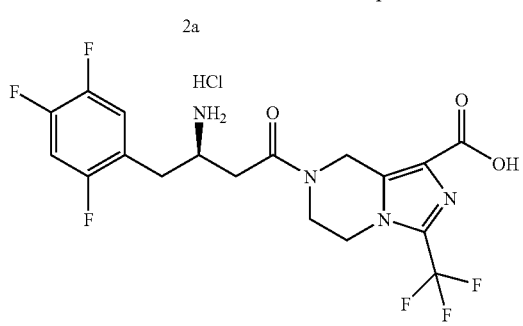

10

Step 1

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (218 mg, 0.4 mmol) was added into the reaction flask. A solution of hydrochloric acid in 5 mL of ethanol was then added to the flask. The reaction mixture was reacted at room temperature and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid hydrochloride 10 (60 mg, yield 30.8%) as a white solid.

MS m/z (ESI): 451.2 [M+1].

$^1$H NMR (400 MHz, CD$_3$OD): δ 7.416-7.37 (m, 1H), 7.281-7.234 (m, 1H), 5.189-5.053 (m, 2H), 4.361-4.286 (m, 1H), 4.15-3.999 (m, 2H), 3.941-3.925 (m, 2H), 3.212-2.883 (m, 2H), 2.861-2.805 (m, 2H).

Example 11

(R)-3-Amino-1-[1-(3-amino-piperidine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride

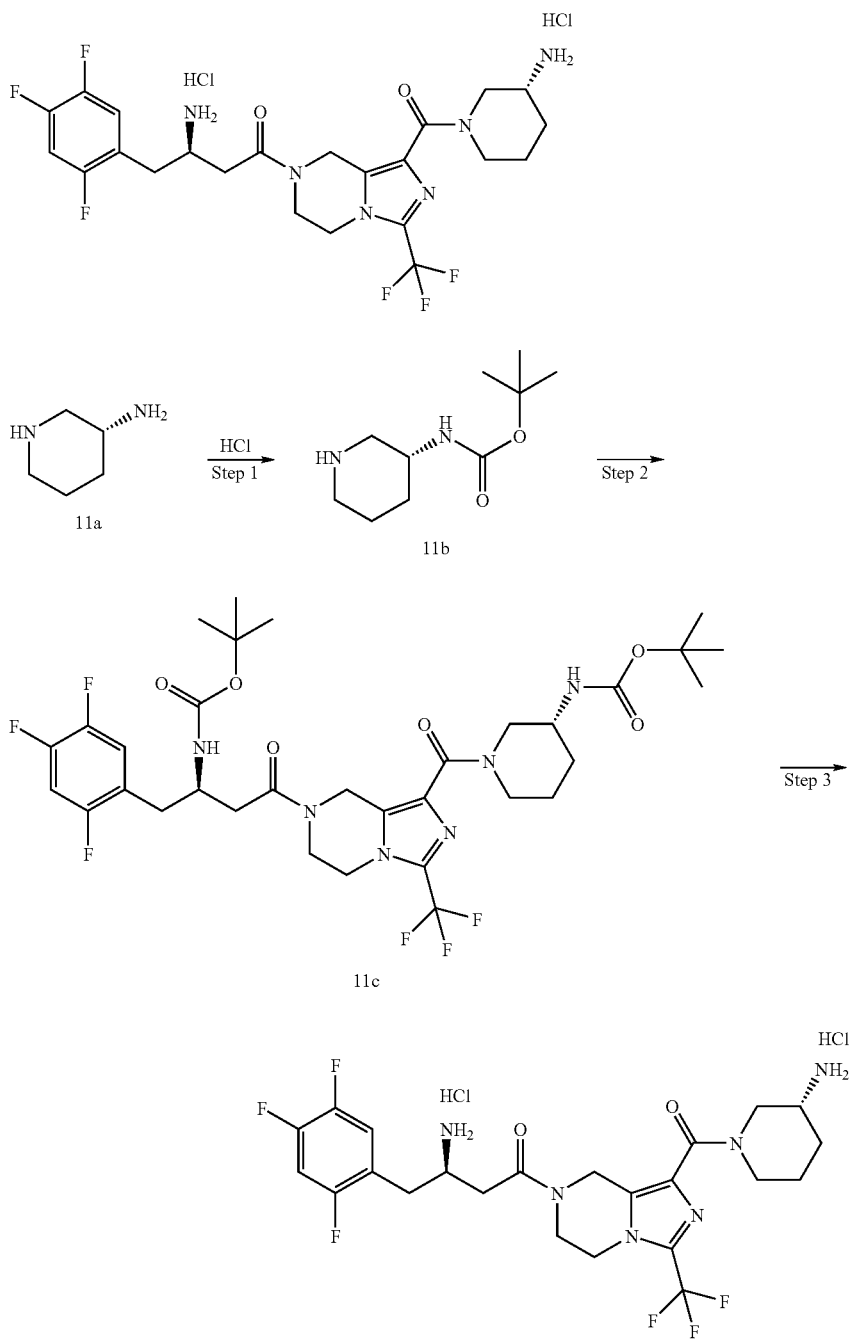

Step 1

Piperidin-3-yl-carbamic acid tert-butyl ester (R)-Piperidin-3-yl amine hydrochloride 11a (3 g, 22.1 mmol) and potassium carbonate (6.1 g, 44.2 mmol) were dissolved in 60 mL of methanol under stirring. After stirring for 30 minutes, di-tert-butyl dicarbonate (4.8 g, 22.1 mmol) was added to the mixture. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound piperidin-3-yl-carbamic acid tert-butyl ester 11b (1.3 g, yield 29%) as an oil.

MS m/z (ESI): 201.0 [M+1].

Step 2

(R)-(1-{7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperidin-3-yl)-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.12 g, 0.218 mmol), piperidin-3-yl-carbamic acid tert-butyl ester 11b (0.173 g, 0.545 mmol) and triethylamine (0.275 g, 2.18 mmol) were dissolved in 12 mL of dichloromethane under stirring, and bis(2-oxo-3-oxazolidinyl)phosphinic chloride (0.138 g, 0.545 mmol) was then added to the mixture. The reaction mixture was reacted at room temperature overnight. The reaction mixture was concentrated under reduced pressure. The resulting residue was purified by silica gel column chromatography to obtain the title compound (R)-(1-{7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperidin-3-yl)-carbamic acid tert-butyl ester 11c (0.1 g, yield 63%) as an oil.

MS m/z (ESI): 733.1 [M+1].

Step 3

(R)-3-Amino-1-[1-(3-amino-piperidine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride (R)-(1-{7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperidin-3-yl)-carbamic acid tert-butyl ester 11c (0.1 g, 0.163 mmol) was added to a solution of 2.3 N hydrochloric acid in 10 mL of ethyl acetate. The reaction mixture was reacted at room temperature overnight and monitored by thin layer chromatography until the disappearance of the starting materials. The reaction mixture was concentrated under reduced pressure to obtain the title compound (R)-3-amino-1-[1-(3-amino-piperidine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride 11 (0.09 g, yield 98%) as a white solid.

MS m/z (ESI): 533.3 [M+1].

$^1$H NMR (400 MHz, CD$_3$OD): δ 7.415-7.396 (m, 1H), 7.26-7.2154 (m, 1H), 5.131-4.085 (m, 11H), 3.994-2.837 (m, 8H), 2.11-1.846 (m, 5H).

Example 12

(R)-3-Amino-1-[1-(pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride

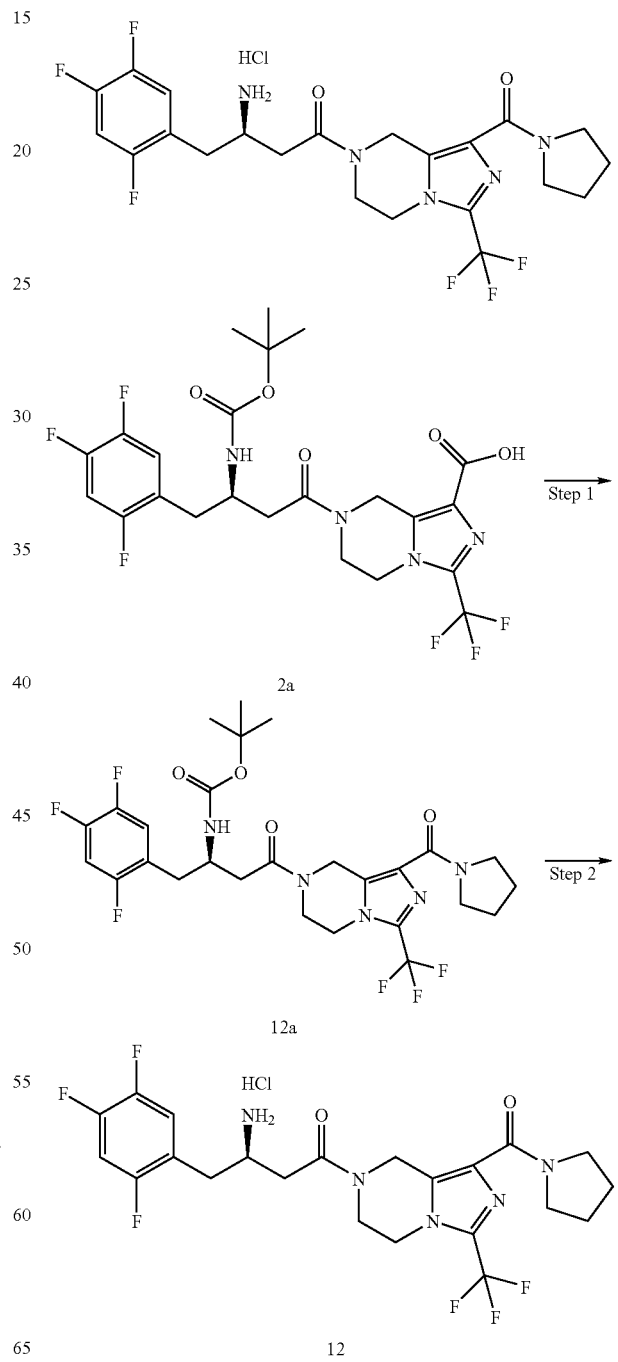

63

Step 1

(R)-[3-Oxo-3-[1-(pyrrolidine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (150 mg, 0.27 mmol), pyrrolidine (38.4 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-oxo-3-[1-(pyrrolidine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 12a (120 mg, yield 74%) as a white solid.

64

Step 2

(R)-3-Amino-1-[1-(pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-Oxo-3-[1-(pyrrolidine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 12a (0.12 g, 0.199 mmol) and 2 mL of ethyl acetate were added into the reaction flask. A solution of 2.3 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-3-amino-1-[1-(pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 12 (0.10 g, yield 94%) as a white solid.

MS m/z (ESI): 504.2 [M+1].

Example 13

(R)-3-Amino-1-[1-(piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride

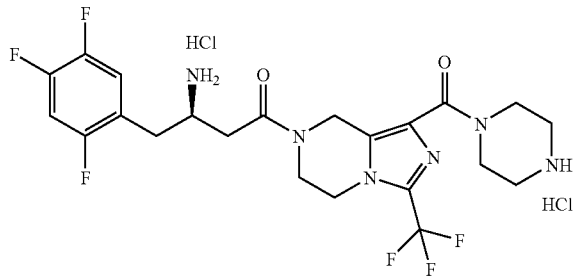

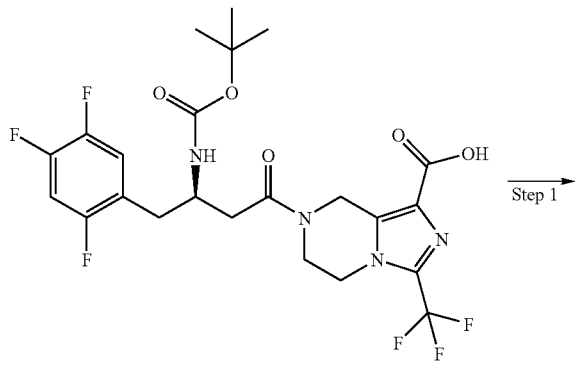

2a

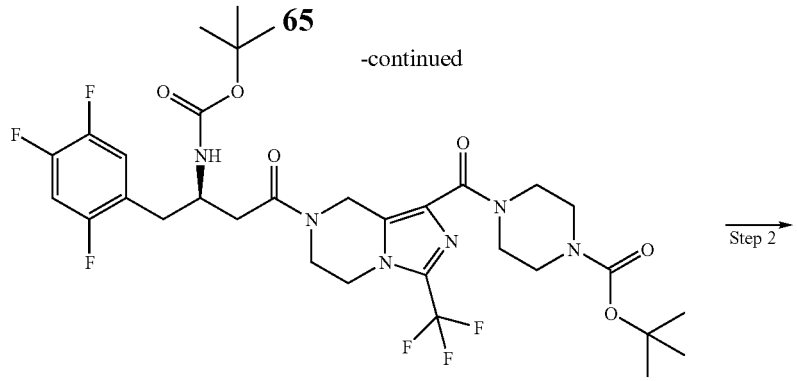

13a

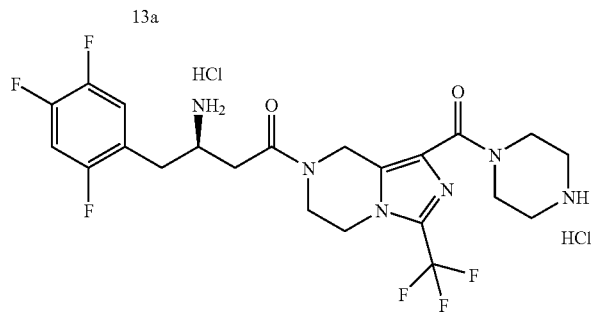

13

Step 1

(R)-4-{7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperazine-1-carboxylic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), tert-butyl piperazine-1-carboxylate (100.6 mg, 0.54 mmol), bis(2-oxo-3-oxazolidinyl)phosphonic chloride (0.138 g, 0.54 mmol) and triethylamine (0.25 mL, 1.62 mmol) were dissolved in 6 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-4-{7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperazine-1-carboxylic acid tert-butyl ester 13a (200 mg, yield 99%) as a white solid.

MS m/z (ESI): 719.0 [M+1].

Step 2

(R)-3-Amino-1-[1-(piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride (R)-4-{7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-piperazine-1-carboxylic acid tert-butyl ester 13a (0.12 g, 0.199 mmol) was added into the reaction flask. A solution of 2.3 N hydrochloric acid in 5 mL of methanol was then added to the flask. The reaction mixture was reacted at room temperature overnight, and then was concentrated under reduced pressure. The resulting residue was purified by silica gel column chromatography to obtain the title compound (R)-3-amino-1-[1-(piperazine-1-carbonyl)-3-trifluoromethyl-5,6-dihydro-8H-imidazo[1,5-a]pyrazin-7-yl]-4-(2,4,5-trifluoro-phenyl)-butan-1-one dihydrochloride 13 (0.10 g, yield 94%) as a white solid.

MS m/z (ESI): 504.2 [M+1].

$^1$H NMR (400 MHz, CD$_3$OD): δ7.45-7.40 (m, 1H), 7.26-7.23 (m, 1H), 5.10-5.04 (m, 2H), 4.71-4.46 (m, 2H), 4.42-4.24 (m, 2H), 4.18-4.06 (m, 2H), 4.06-3.89 (m, 3H), 3.78-3.55 (m, 4H), 3.24-3.06 (m, 2H), 3.06-2.80 (m, 2H).

Example 14

(R)-3-Amino-1-[1-((R)-3-hydroxy-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride

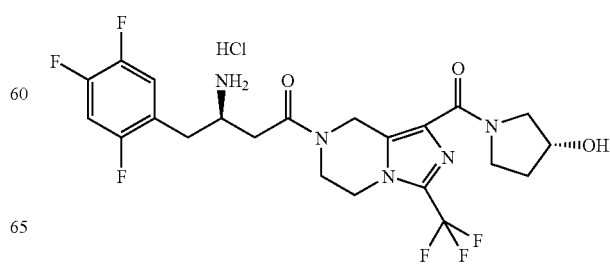

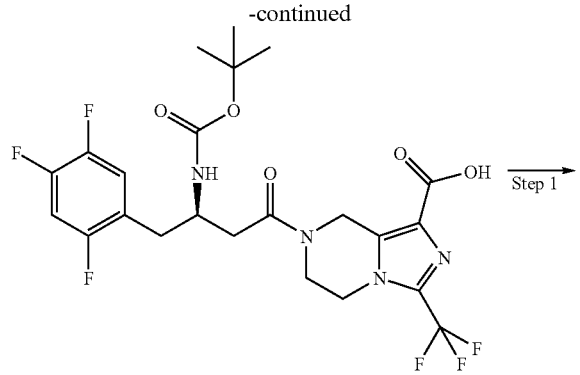

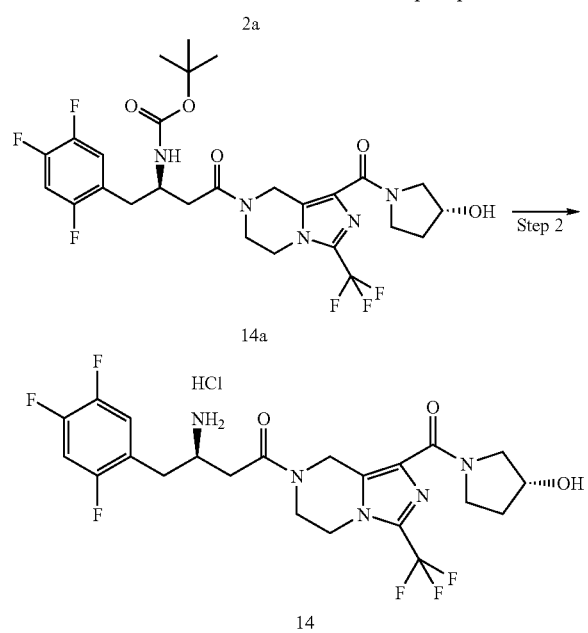

Step 1

(R)-[3-[1-((R)-3-Hydroxy-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), (R)-3-pyrrolidinol (47 mg, 0.54 mmol), bis(2-oxo-3-oxazolidinyl)phosphonic chloride (0.138 g, 0.54 mmol) and triethylamine (0.25 mL, 1.62 mmol) were dissolved in 6 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-((R)-3-hydroxy-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 14a (90 mg, yield 53%) as a white solid.

MS m/z (ESI): 620.0 [M+1].

Step 2

(R)-3-Amino-1-[1-((R)-3-hydroxy-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-((R)-3-Hydroxy-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 14a (90 mg, 0.15 mmol) was added to a solution of 2.3 N hydrochloric acid in 10 mL of ethyl acetate. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-3-amino-1-[1-((R)-3-hydroxy-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 14 (60 mg, yield 72%) as a white solid.

MS m/z (ESI): 520.3 [M+1].

$^1$H NMR (400 MHz, CD$_3$OD): δ 7.417-7.372 (m, 1H), 7.275-7.234 (m, 1H), 5.527-4.87 (m, 2H), 4.87-4.346 (m, 1H), 4.346-4.117 (m, 2H), 4.117-3.352 (m, 8H), 3.349-2.98 (m, 2H), 2.98-2.088 (m, 2H), 2.088-2.029 (m, 2H).

Example 15

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid cyclopropylamide hydrochloride

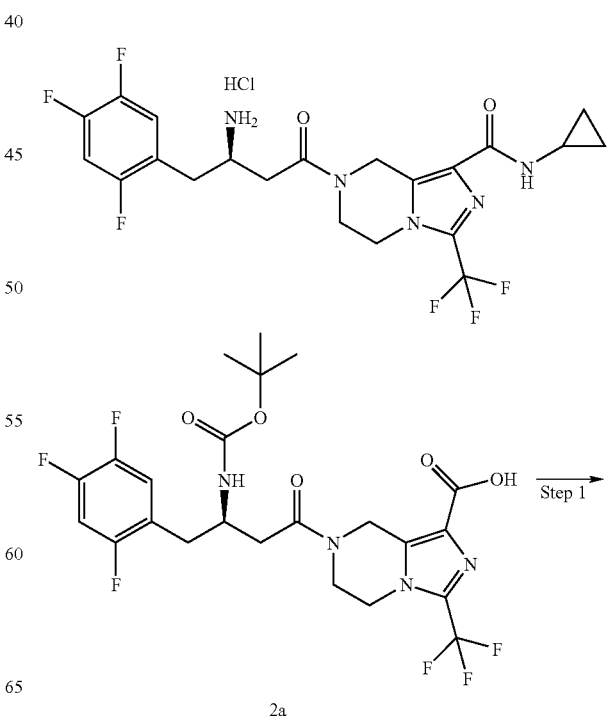

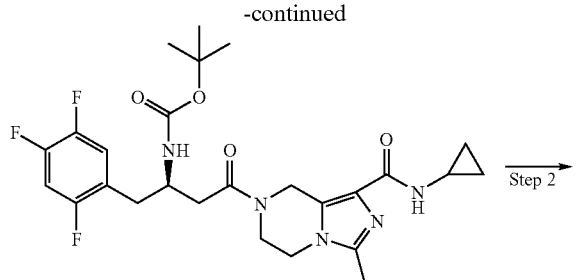

15a

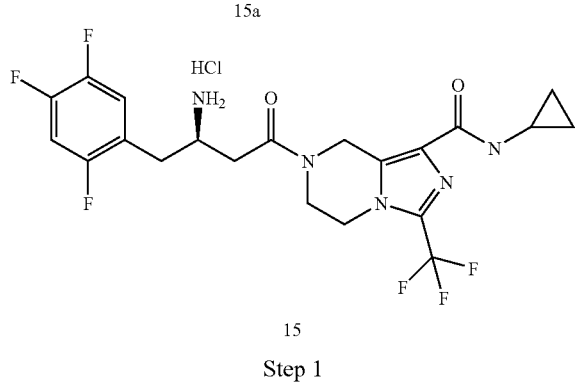

15

Step 1

(R)-[3-(1-Cyclopropylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.2 g, 0.36 mmol), cyclopropylamine (0.05 g, 0.54 mmol) and bis(2-oxo-3-oxazolidinyl)phosphinic chloride (0.18 g, 0.72 mmol) were dissolved in 20 mL of dichloromethane under stirring, and triethylamine (0.36 g, 3.6 mmol) was added to the solution at room temperature. The reaction mixture was reacted at room temperature for 2 hours, and then concentrated under reduced pressure. The resulting residue was purified by silica gel column chromatography to obtain the title compound (R)-[3-(1-cyclopropylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 15a (0.1 g, yield 45%) as an oil.

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid cyclopropylamide hydrochloride (R)-[3-(1-Cyclopropylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 15a (0.1 g, 0.16 mmol) was added to a solution of 2.2 N hydrochloric acid in 5 mL of ethyl acetate. The reaction mixture was reacted at room temperature overnight and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid cyclopropylamide hydrochloride 15 (82 mg, yield 95%) as a light yellow solid.

MS m/z (ESI): 490.2 [M+1].

$^1$H NMR (400 MHz, CD$_3$OD): δ 7.423-7.174 (m, 2H), 5.284-4.872 (m, 2H), 4.716-2.019 (m, 10H), 2.019 (s, 2H), 1.349-1.191 (m, 2H), 0.907-0.596 (m, 2H).

Example 16

(R)-({7-[3-Amino-4-(2,4,5-trifluoro-phenyl)-butyryl]-3-trifluoromethyl-5,6,7,8-tetrahydro-imidazo[1,5-a]pyrazine-1-carbonyl}-amino)-acetic acid methyl ester hydrochloride

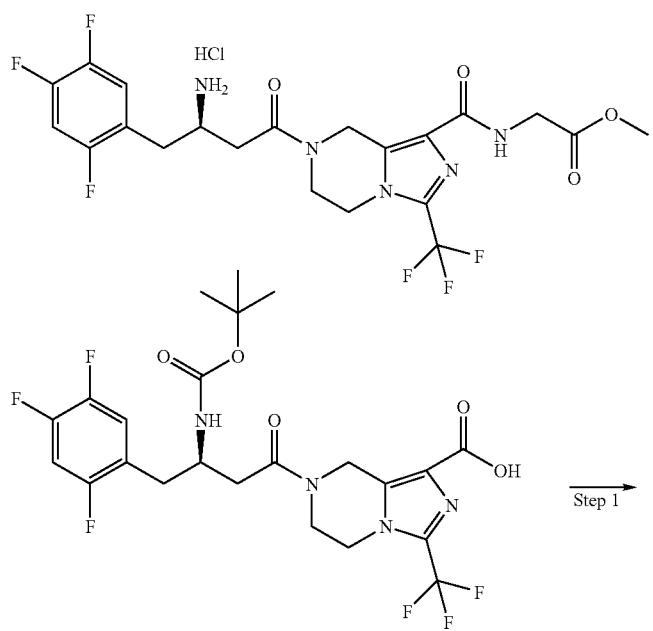

2a

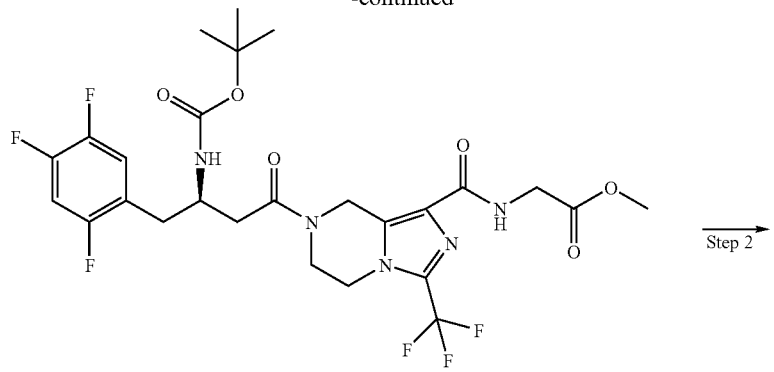

16a

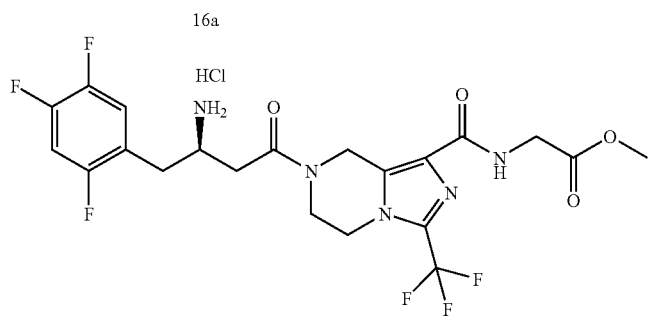

16

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol) and methyl glycinate hydrochloride (512 mg, 0.408 mmol) were dissolved in 8 mL of dichloromethane under stirring, and triethylamine (0.25 mL, 1.62 mmol) was then added to the solution. After stirring for 5 minutes, bis(2-oxo-3-oxazolidinyl)phosphonic chloride (0.138 g, 0.54 mmol) was added. The reaction mixture was reacted at room temperature for 20 hours and monitored by thin layer chromatography until the disappearance of the starting materials. The reaction mixture was concentrated under reduced pressure. The resulting residue was purified by silica gel column chromatography to obtain the title compound (R)-({7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carbonyl}-amino)-acetic acid methyl ester 16a (90 mg, yield 53.6%) as a light yellow oil.

Step 2

(R)-({7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carbonyl}-amino)-acetic acid methyl ester 16a (0.09 g, 0.145 mmol) and 2 mL of ethyl acetate were added into the reaction flask. A solution of 2.3 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-({7-[3-amino-4-(2,4,5-trifluorophenyl)-butyryl]-3-trifluoromethyl-5,6,7,8-tetrahydro-imidazo[1,5-a]pyrazine-1-carbonyl}-amino)-acetic acid methyl ester hydrochloride 16 (80 mg, yield 99%) as a white solid.

MS m/z (ESI): 522.2 [M+1].

$^1$H NMR (400 MHz, CD$_3$OD): δ7.47-7.30 (m, 1H), 7.30-7.14 (m, 1H), 5.23-5.00 (m, 2H), 4.39-4.20 (m, 2H), 4.18-4.06 (m, 3H), 4.17-4.07 (m, 3H), 4.01-3.89 (m, 2H), 3.84-3.24 (m, 3H), 3.20-2.76 (m, 4H).

Example 17

(R)-1-[1-(4-Acetyl-piperazine-1-carbonyl)-3-trifluoromethyl-5,6-dihydro-8H-imidazo[1,5-a]pyrazin-7-yl]-3-amino-4-(2,4,5-trifluoro-phenyl)-butan-1-one hydrochloride

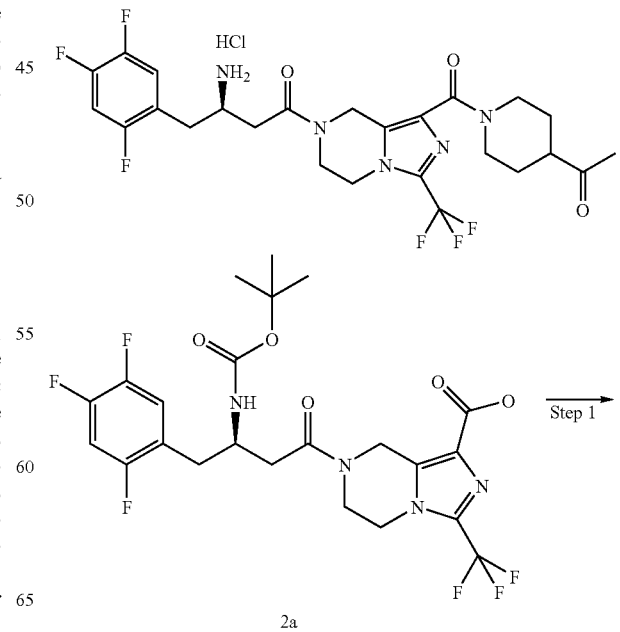

2a

-continued

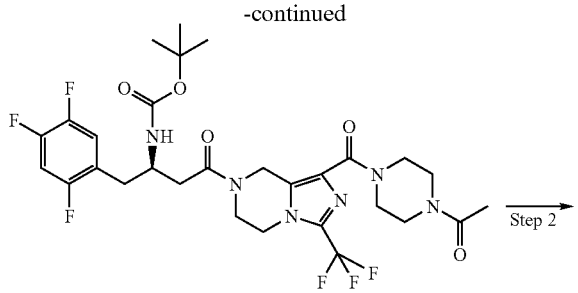

17a

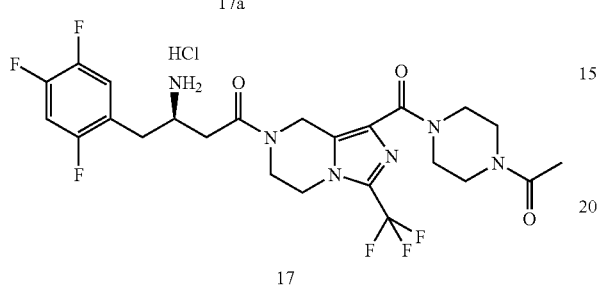

17

Step 1

(R)-[3-[1-(4-Acetyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (150 mg, 0.27 mmol), 1-piperazin-1-yl-ethanone hydrochloride (90 mg, 0.54 mmol) and bis(2-oxo-3-oxazolidinyl)phosphonic chloride (0.138 g, 0.54 mmol) were dissolved in 8 mL of dichloromethane under stirring, and triethylamine (0.25 mL, 1.62 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(4-acetyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 17a (80 mg, yield 45%) as a white solid.

MS m/z (ESI): 660.9 [M+1].

Step 2

(R)-1-[1-(4-Acetyl-piperazine-1-carbonyl)-3-trifluoromethyl-5,6-dihydro-8H-imidazo[1,5-a]pyrazin-7-yl]-3-amino-4-(2,4,5-trifluoro-phenyl)-butan-1-one hydrochloride (R)-[3-[1-(4-Acetyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 17a (0.08 g, 0.12 mmol) and 2 mL of ethyl acetate were added into the reaction flask. A solution of 2.7 N hydrochloric acid in 2 mL of ethyl acetate was then added to the flask. The reaction mixture was reacted at room temperature overnight and monitored by thin layer chromatography until the disappearance of the starting materials. The reaction mixture was concentrated under reduced pressure to obtain the title compound (R)-1-[1-(4-acetyl-piperazine-1-carbonyl)-3-trifluoromethyl-5,6-dihydro-8H-imidazo[1,5-a]pyrazin-7-yl]-3-amino-4-(2,4,5-trifluoro-phenyl)-butan-1-one hydrochloride 17 (70 mg, yield 98%) as a white solid.

MS m/z (ESI): 561.2 [M+1].

¹H NMR (400 MHz, CD₃OD): δ7.50-7.36 (m, 1H), 7.33-7.15 (m, 1H), 5.23-4.97 (m, 2H), 4.60-4.06 (m, 5H), 4.06-3.88 (m, 2H), 3.88-3.48 (m, 6H), 3.24-2.71 (m, 4H), 2.26-2.12 (m, 3H).

Example 18

(R)-3-Amino-1-[1-(-hydroxymethyl-pyrrolidine-1-carbonyl)-3-trifluoromethyl-5,6-dihydro-8H-imidazo[1,5-a]pyrazin-7-yl]-4-(2,4,5-trifluorohenyl)-butan-1-one hydrochloride

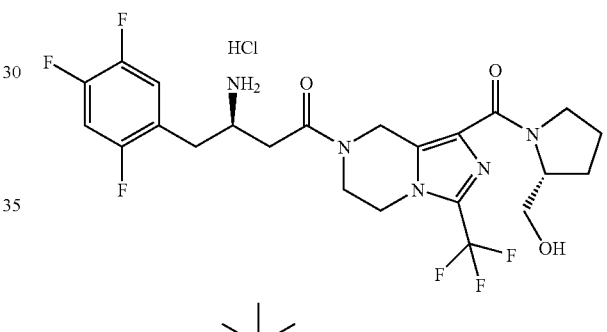

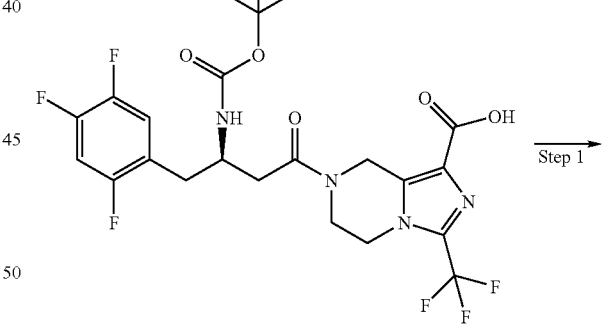

2a

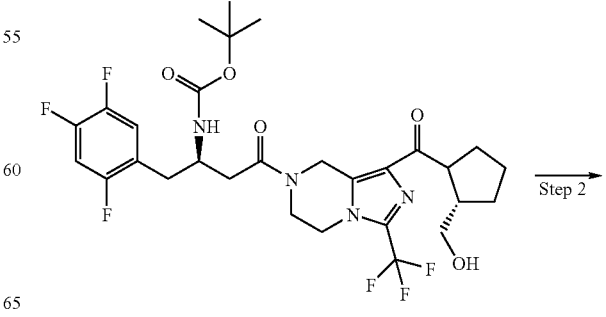

18a

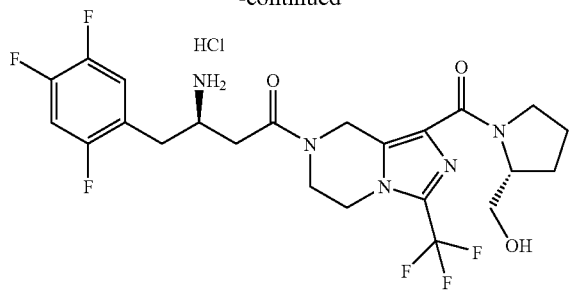

18

Step 1

(R)-[3-[1-(2R)-(2-Hydroxymethyl-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (150 mg, 0.27 mmol), (R)-pyrrolidin-2-ylmethanol (54.6 mg, 0.54 mmol), bis(2-oxo-3-xazolidinyl)hosphonic chloride (0.138 g, 0.54 mmol) and triethylamine (0.25 mL, 1.62 mmol) were dissolved in 8 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-((2R)-2-hydroxy-methyl-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 18a (120 mg, yield 70%) as a colourness oil.

MS m/z (ESI): 633.9 [M+1].

Step 2

(R)-3-Amino-1-[1-((2R)-2-hydroxymethyl-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-((2R)-2-Hydroxymethyl-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 18a (0.12 g, 0.19 mmol) and 2 mL of ethyl acetate were added into the reaction flask. A solution of 2.3 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-3-amino-1-[1-((2R)-2-hydroxymethyl-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 18 (0.12 g, yield 88%) as a white solid.

MS m/z (ESI): 534.2 [M+1].

$^1$H NMR (400 MHz, CD$_3$OD): δ7.39-7.35 (m, 1H), 7.23-7.19 (m, 1H), 5.16-5.04 (m, 2H), 4.33-4.26 (m, 2H), 4.15-4.09 (m, 2H), 3.98 (m, 1H), 3.86-3.57 (m, 5H), 3.04 (m, 2H), 2.93-2.86 (m, 1H), 2.82-2.72 (m, 1H)

Example 19

(R)-4-{7-[3-Amino-4-(2,4,5-trifluoro-phenyl)-butyryl]-3-trifluoromethyl-5,6,7,8-tetrahydro-imidazo[1,5-a]pyrazine-1-carbonyl}-piperazin-2-one hydrochloride

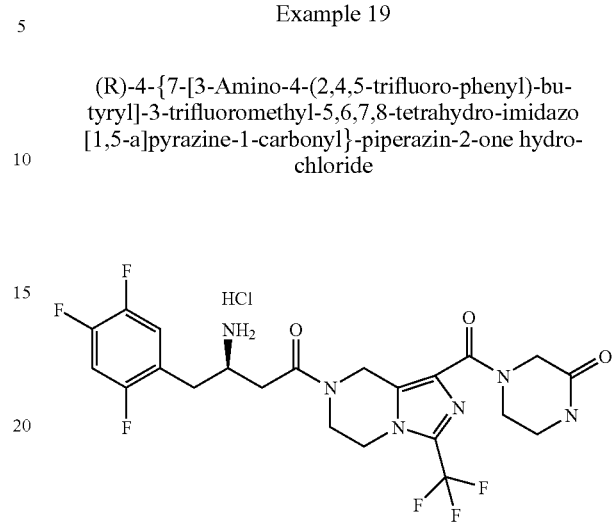

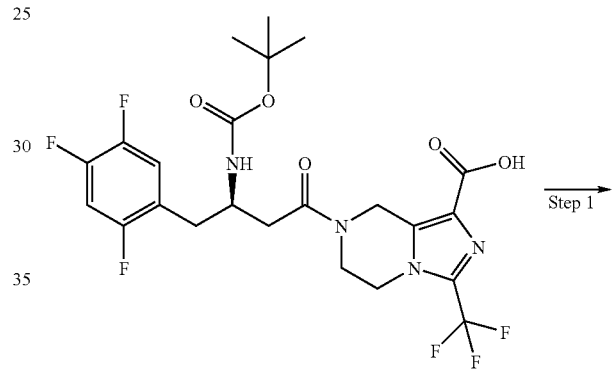

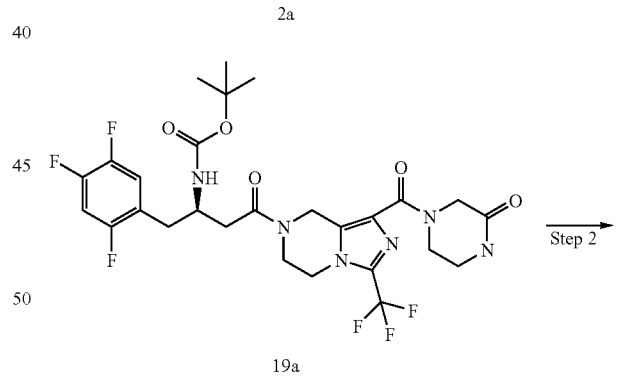

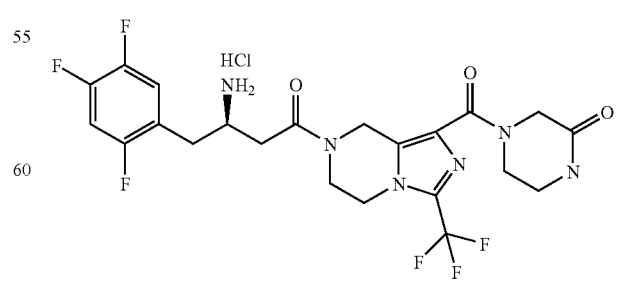

Step 1

(R)-[3-Oxo-3-[1-(3-oxo-piperazine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (150 mg, 0.27 mmol), piperazin-2-one (60 mg, 0.6 mmol), bis(2-oxo-3-oxazolidinyl) phosphonic chloride (0.138 g, 0.54 mmol), triethylamine (0.25 mL, 1.62 mmol) and 8 mL of dichloromethane were added into the reaction flask, and 10 mL of N,N-dimethylformamide was then added to the flask. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-oxo-3-[1-(3-oxo-piperazine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 19a (140 mg, yield 82%) as a colourness oil.

MS m/z (ESI): 632.7 [M+1].

Step 2

(R)-4-{7-[3-Amino-4-(2,4,5-trifluoro-phenyl)-butyryl]-3-trifluoromethyl-5,6,7,8-tetrahydro-imidazo[1,5-a]pyrazine-1-carbonyl}-piperazin-2-one hydrochloride (R)-[3-Oxo-3-[1-(3-oxo-piperazine-1-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 19a (0.14 g, 0.22 mmol) and 2 mL of ethyl acetate were added into the reaction flask. A solution of 2.3 N hydrochloric acid in 4 mL of ethyl acetate was then added to the flask. The reaction mixture was reacted at room temperature overnight and monitored by thin layer chromatography until the disappearance of the starting materials. The reaction mixture was concentrated under reduced pressure to obtain the title compound (R)-4-{7-[3-amino-4-(2,4,5-trifluorophenyl)-butyryl]-3-trifluoromethyl-5,6,7,8-tetrahydro-imidazo[1,5-a]pyrazine-1-carbonyl}-piperazin-2-one hydrochloride 19 (0.12 g, yield 93%) as a white solid.

MS m/z (ESI): 533.2 [M+1].

$^1$H NMR (400 MHz, CD$_3$OD): δ 7.38 (m, 1H), 7.24-7.22 (m, 1H), 5.08-5.01 (m, 2H), 4.57 (m, 2H), 4.32-4.27 (m, 2H), 4.08 (m, 1H), 3.97-3.94 (m, 4H), 3.47 (m, 2H), 3.11 (m, 2H), 2.97-2.84 (m, 2H).

Example 20

(R)-3-Amino-1-[1-(thiazolidine-3-carbonyl)-3-trifluoromethyl-5,6-dihydro-8H-imidazo[1,5-a]pyrazin-7-yl]-4-(2,4,5-trifluoro-phenyl)-butan-1-one hydrochloride

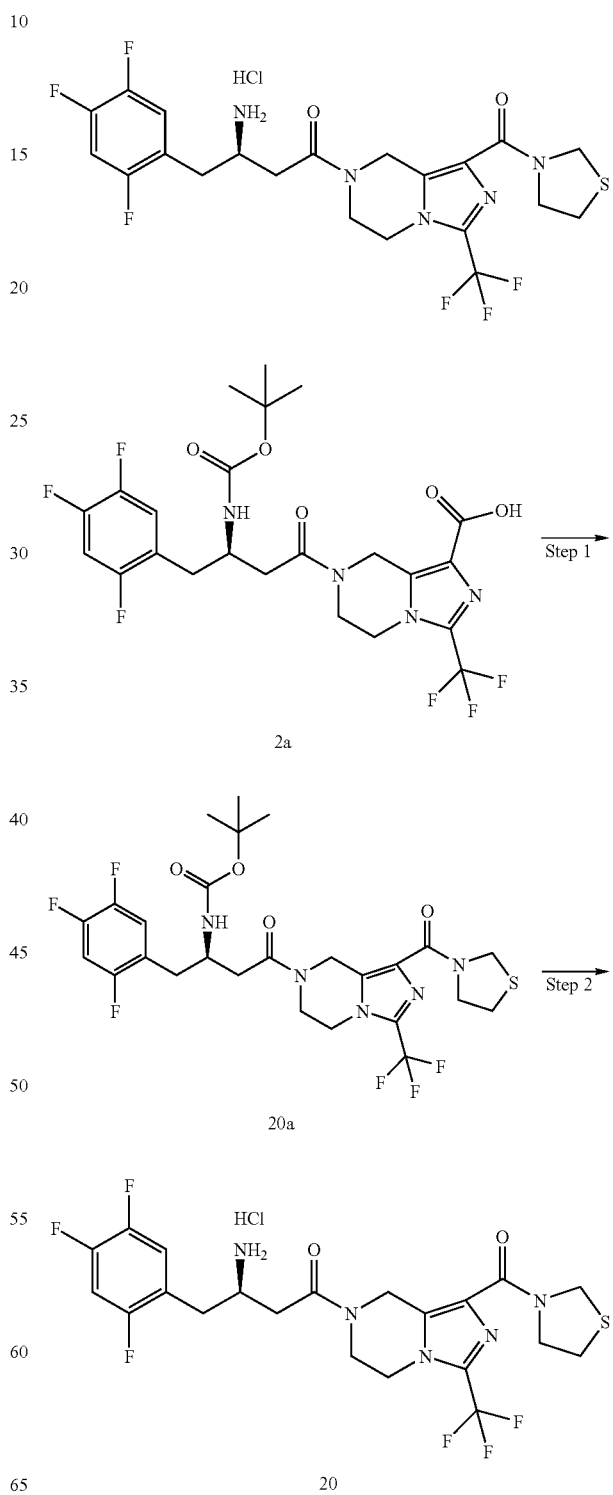

Step 1

(R)-[3-oxo-3-[1-(thiazolidine-3-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (0.15 g, 0.27 mmol), thiazolidine (57 mg, 0.6 mmol), triethylamine (0.275 g, 2.72 mmol) and bis(2-oxo-3-oxazolidinyl)phosphinic chloride (0.138 g, 0.544 mmol) were dissolved in 10 mL of dichloromethane under stirring. The reaction mixture was stirred at room temperature for 2 hours and monitored by thin layer chromatography until the disappearance of the starting materials. The reaction mixture was concen-trated under reduced pressure. The resulting residue was purified by silica gel column chromatography to obtain the title compound (R)-[3-oxo-3-[1-(thiazolidine-3-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 20a (0.15 g, yield 89%) as a white solid.

MS m/z (ESI): 644.1 [M+23].

Step 2

(R)-3-Amino-1-[1-(thiazolidine-3-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-oxo-3-[1-(thiazolidine-3-carbonyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 20a (0.15 g, 0.24 mmol) was added to a solution of 2.2 N hydrochloric acid in 5 mL of ethyl acetate. The reaction mixture was reacted at room temperature for 4 hours and monitored by thin layer chromatography until the disappearance of the starting materials. The reaction mixture was concentrated under reduced pressure. The resulting residue was purified by silica gel column chromatography to obtain the title compound (R)-3-amino-1-[1-(thiazolidine-3-carbonyl)-3-trifluoromethyl-5,6-dihydro-8H-imidazo[1,5-a]pyrazin-7-yl]-4-(2,4,5-trifluorophenyl)-butan-1-one hydrochloride 20 (100 mg, yield 75%) as a light yellow solid.

MS m/z (ESI): 522.1 [M+1].

$^1$H NMR (400 MHz, CD$_3$OD): δ 7.447-7.358 (m, 1H), 7.3-7.204 (m, 1H), 5.217-5.05 (m, 2H), 4.752-4.461 (m, 2H), 4.37-4.284 (m, 2H), 4.284-4.086 (m, 2H), 4.086-3.952 (m, 2H), 3.719-3.607 (m, 1H), 3.211-2.827 (m, 4H), 2.827-2.784 (m, 2H).

Example 21

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride

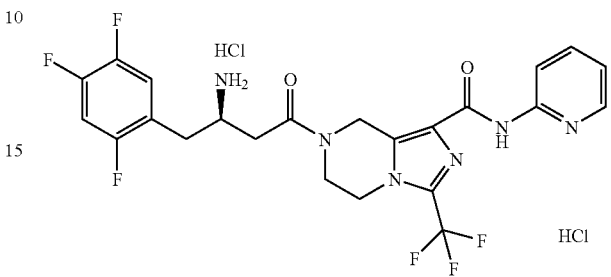

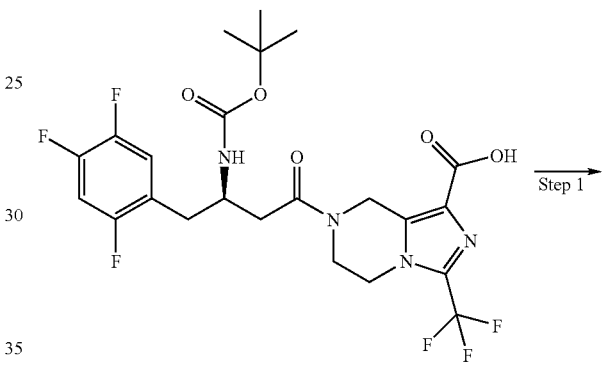

2a

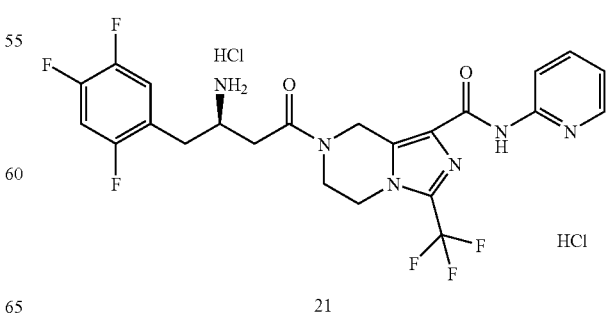

21a

21

Step 1

(R)-[3-Oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (0.15 g, 0.272 mmol) was dissolved in 10 mL of dichloromethane under stirring, and 3-aminopyridine (38.4 mg, 0.41 mmol), triethylamine (0.275 g, 2.72 mmol) and bis(2-oxo-3-oxazolidinyl)phosphinic chloride (0.138 g, 0.544 mmol) were then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 21a (0.1 g, yield 58.8%) as a white solid.

MS m/z (ESI): 627.1 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride (R)-[3-oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 21a (0.1 g, 0.16 mmol) was added to a solution of 2.2 N hydrochloric acid in 10 mL of ethyl acetate. The reaction mixture was reacted at room temperature for 4 hours and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride 21 (80 mg, yield 89%) as a white solid.

MS m/z (ESI): 527.2 [M+1].

$^1$H NMR (400 MHz, CD$_3$OD): δ 9.584 (s, 1H), 8.88-8.857 (m, 1H), 8.63-8.601 (m, 1H), 8.115-8.07 (m, 1H), 7.438-7.215 (m, 2H), 5.209-5.137 (m, 2H), 4.87-3.937 (m, 5H), 3.34-2.902 (m, 5H), 2.061 (m, 2H).

Example 22

(R)-3-Amino-1-[1-(4-methanesulfonyl-piperazine-1-carbonyl)-3-trifluoromethyl-5,6-dihydro-8H-imidazo[1,5-a]pyrazin-7-yl]-4-(2,4,5-trifluorophenyl)-butan-1-one hydrochloride

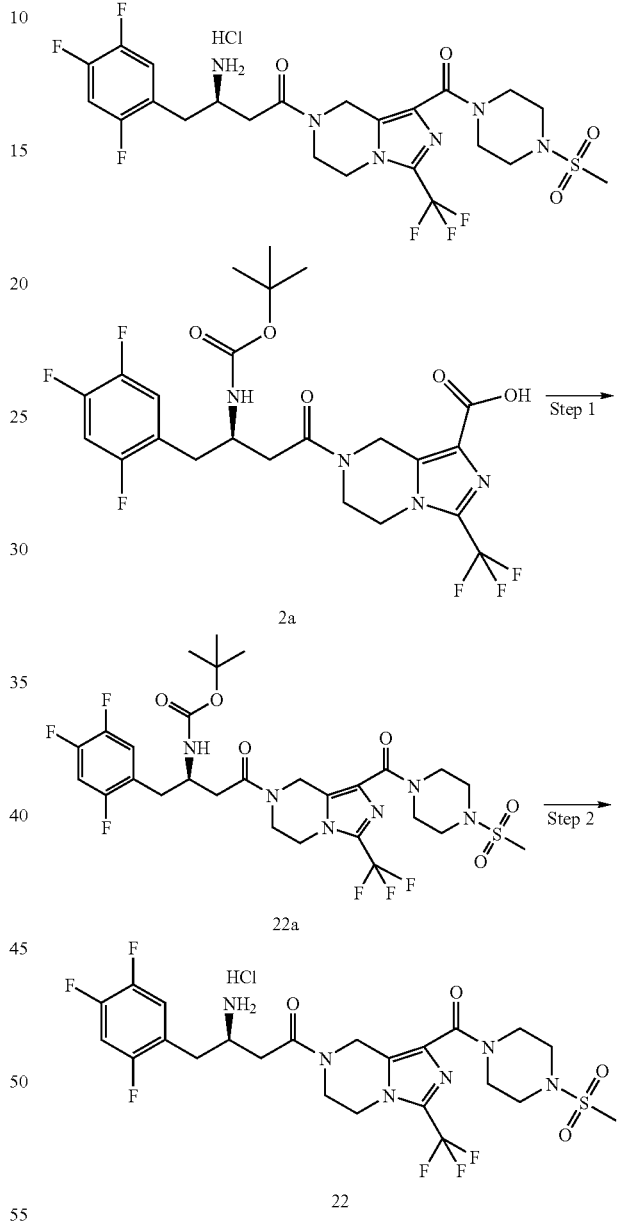

Step 1

(R)-[3-[1-(4-Methanesulfonyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (0.15 g, 0.27 mmol), 1-methanesulfonyl-piperazine (0.109 g, 0.55 mmol) and triethylamine (0.38 mL, 2.7 mmol) were dissolved in 10 mL of dichloromethane under stirring, and bis(2-oxo-3-oxazolidinyl)phosphinic chloride (0.139 g, 0.55 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(4-methanesulfonyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 22a (0.2 g) as a white solid.

MS m/z (ESI): 696.9 [M+1].

Step 2

(R)-3-Amino-1-[1-(4-methanesulfonyl-piperazine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-(4-Methanesulfonyl-piperazine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 22a (0.19 g, 0.27 mmol) and 2 mL of ethyl acetate were added into the reaction flask. A solution of 2.7 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-3-amino-1-[1-(4-methanesulfonyl-piperazine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 22 (170 mg, yield 99%) as a white solid.

MS m/z (ESI): 597.2 [M+1].

$^1$H NMR (400 MHz, CD$_3$OD): δ7.46-7.34 (m, 1H), 7.33-7.20 (m, 1H), 5.18-5.07 (s, 1H), 5.06-4.97 (s, 1H), 4.56-4.28 (m, 4H), 4.17-4.07 (m, 1H), 4.03-3.78 (m, 4H), 3.73-3.17 (m, 3H), 3.16-2.75 (m, 8H).

Example 23

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid ethyl ester hydrochloride

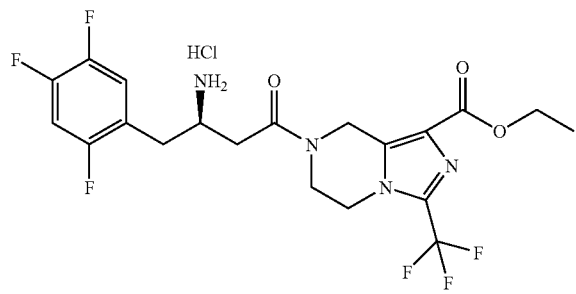

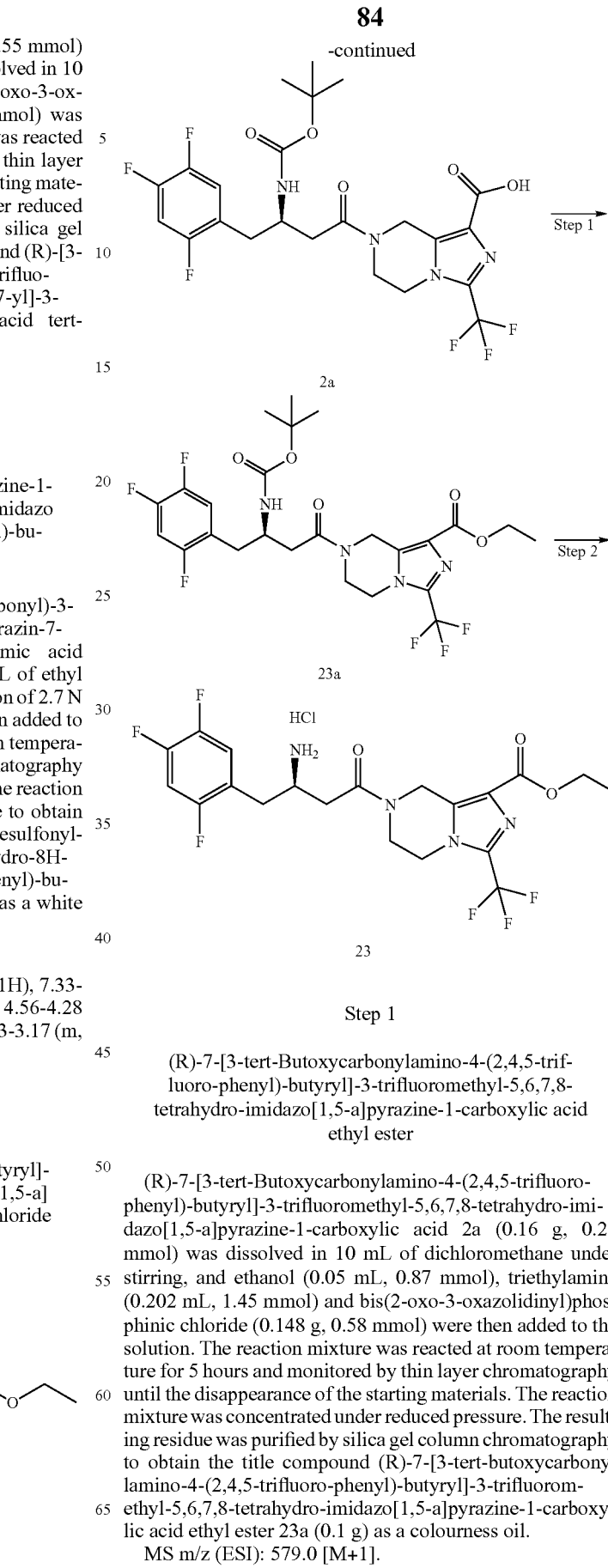

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid ethyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.16 g, 0.29 mmol) was dissolved in 10 mL of dichloromethane under stirring, and ethanol (0.05 mL, 0.87 mmol), triethylamine (0.202 mL, 1.45 mmol) and bis(2-oxo-3-oxazolidinyl)phosphinic chloride (0.148 g, 0.58 mmol) were then added to the solution. The reaction mixture was reacted at room temperature for 5 hours and monitored by thin layer chromatography until the disappearance of the starting materials. The reaction mixture was concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid ethyl ester 23a (0.1 g) as a colourness oil.

MS m/z (ESI): 579.0 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid ethyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid ethyl ester 23a (0.09 g, 0.156 mmol) and 2 mL of ethyl acetate were added into the reaction flask. A solution of 2.7 N hydrochloric acid in 4 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid ethyl ester hydrochloride 23 (80 mg, yield 99%) as a white solid.

MS m/z (ESI): 479.1 [M+1].

$^1$H NMR (400 MHz, CD$_3$OD): δ7.50-7.45 (m, 1H), 7.40-7.18 (m, 1H), 5.20-5.00 (m, 2H), 4.5-4.22 (m, 4H), 4.15-4.06 (m, 1H), 4.06-3.89 (m, 2H), 3.23-2.78 (m, 4H), 1.40-1.48 (m, 3H).

Example 24

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid amide hydrochloride

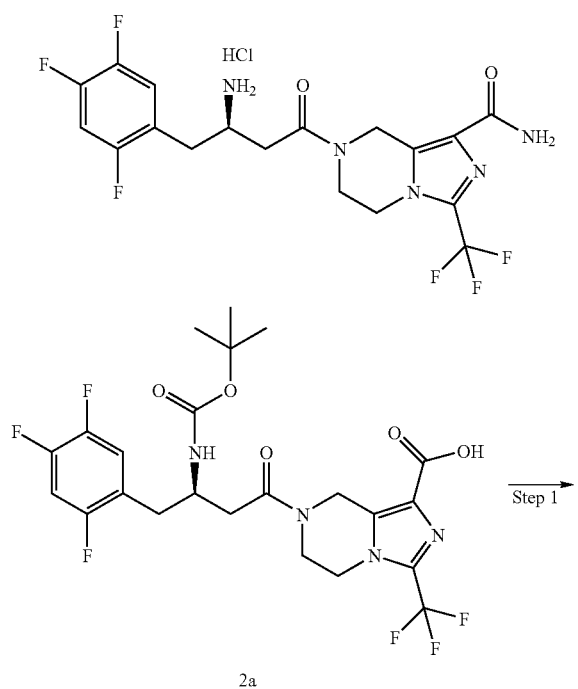

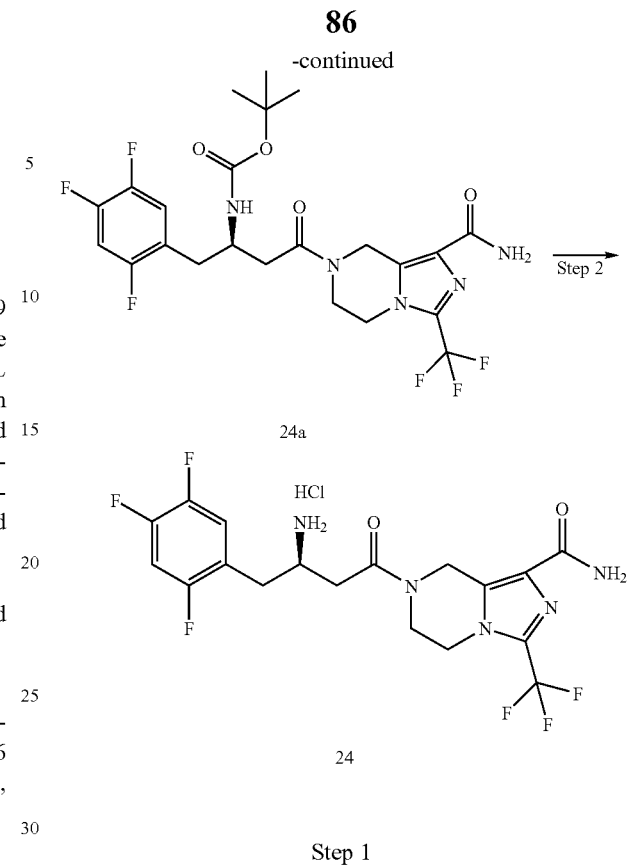

Step 1

(R)-[3-(1-Carbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), bis(2-oxo-3-oxazolidinyl)phosphinic chloride (0.206 g, 1.08 mmol) and triethylamine (0.25 mL, 1.62 mmol) were dissolved in 10 mL of tetrahydrofuran under stirring. After stirring for 10 minutes, ammonium carbonate (78 mg, 0.81 mmol) was added. The reaction mixture was reacted at room temperature over-night and monitored by thin layer chromatography until the disappearance of the starting materials. The reaction mixture was concentrated under reduced pressure. The resulting residue was purified by silica gel column chromatography to obtain the title compound (R)-[3-(1-carbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 24a (0.162 g) as a white solid.

MS m/z (ESI): 549.9 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid amide hydrochloride (R)-[3-(1-Carbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 24a (0.16 g, 0.29 mmol) and 2 mL of ethyl acetate were added into the reaction flask. A solution of 2.7 N hydrochloric acid in 5 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid amide hydrochloride 24 (150 mg, yield 95%) as a white solid.

MS m/z (ESI): 450.2 [M+1].

$^1$H NMR (400 MHz, CD$_3$OD): δ7.40-7.36 (m, 1H), 7.28-7.22 (m, 1H), 5.14-5.05 (m, 2H), 4.34-4.27 (m, 2H), 4.10-4.07 (m, 1H), 3.99-3.94 (m, 1H), 3.21-3.09 (m, 2H), 3.02-2.85 (m, 1H), 2.82-2.76 (m, 11-1).

Example 25

(R)-3-Amino-1-[1-((R)-3-fluoro-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride

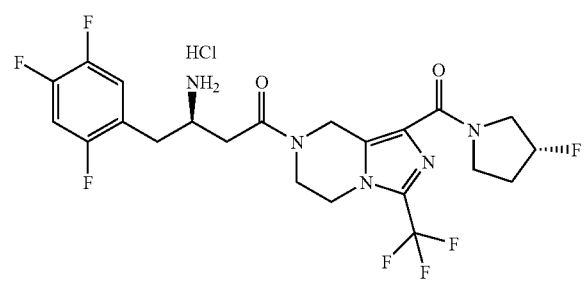

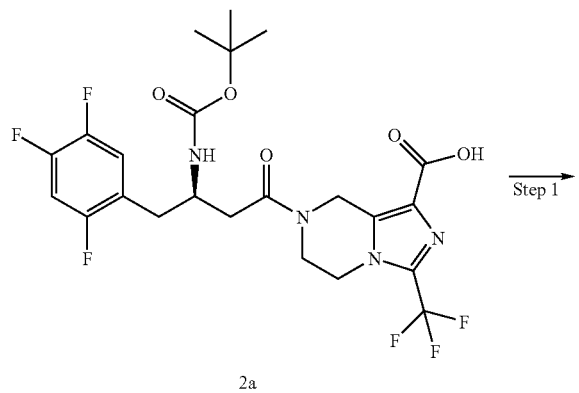
2a

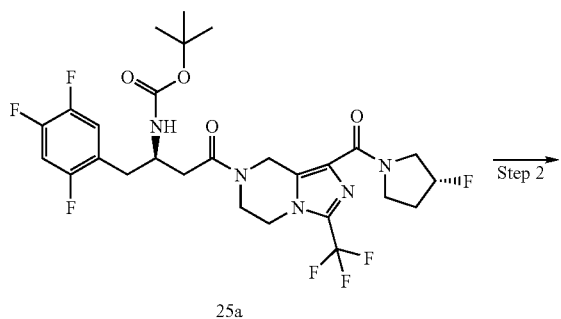
25a

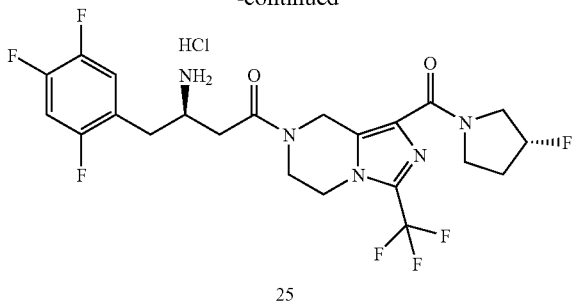
25

Step 1

(R)-[3-[1-((R)-3-Fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), bis(2-oxo-3-oxazolidinyl)phosphinic chloride (0.140 g, 0.54 mmol), triethylamine (0.4 mL, 2.6 mmol) and (R)-3-fluoropyrrolidine hydrochloride (68 mg, 0.54 mmol) were dissolved in 10 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-((R)-3-fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 25a (0.162 g) as a white solid.

MS m/z (ESI): 622.0 [M+1].

Step 2

(R)-3-Amino-1-[1-((R)-3-fluoro-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-((R)-3-Fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 25a (0.15 g, 0.27 mmol) and 2 mL of ethyl acetate were added into the reaction flask. A solution of 2.7 N hydrochloric acid in 5 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-3-amino-1-[1-((R)-3-fluoro-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 25 (140 mg, yield 94%) as a white solid.

MS m/z (ESI): 522.2 [M+1].

$^1$H NMR (400 MHz, CD$_3$OD): δ7.42-7.37 (m, 1H), 7.26-7.22 (m, 1H), 5.47-5.29 (m, 1H), 5.18-5.10 (m, 2H), 4.56-

4.48 (m, 1H), 4.37-4.28 (m, 2H), 4.16-3.89 (m, 5H), 3.74-3.68 (m, 1H), 3.16-3.11 (m, 2H), 3.07-2.77 (m, 2H), 2.39-2.03 (m, 2H).

Example 26

(R)-3-Amino-1-[1-((S)-3-fluoro-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride

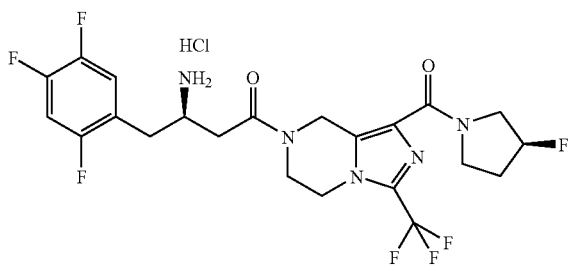

2a

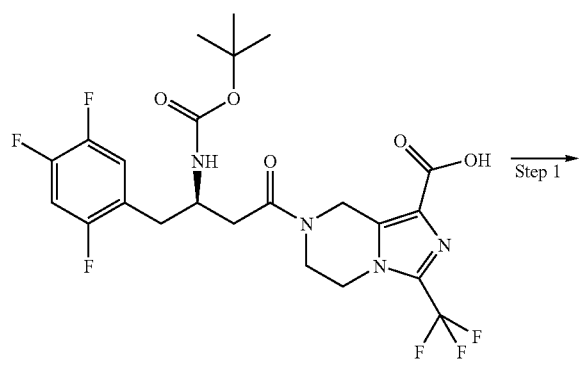

26a

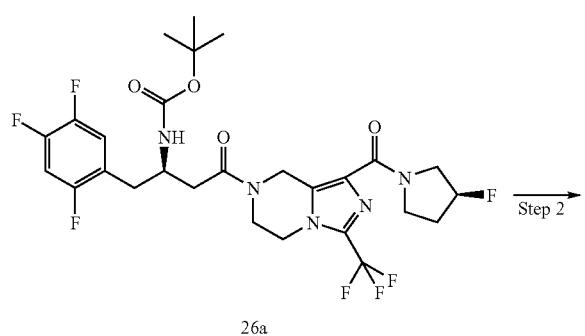

26

Step 1

(R)-[3-[1-((S)-3-Fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), bis(2-oxo-3-oxazolidinyl)phosphinic chloride (0.140 g, 0.54 mmol), triethylamine (0.4 mL, 2.6 mmol) and (S)-3-fluoropyrrolidine hydrochloride (68 mg, 0.54 mmol) were dissolved in 10 mL of dichloromethane under stirring. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-((S)-3-fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 26a (0.15 g, yield 89%) as a white solid.

MS m/z (ESI): 622.0 [M+1].

Step 2

(R)-3-Amino-1-[1-((S)-3-fluoro-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride (R)-[3-[1-((S)-3-Fluoro-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 26a (0.15 g, 0.24 mmol) and 2 mL of ethyl acetate were added into the reaction flask. A solution of 2.7 N hydrochloric acid in 5 mL of ethyl acetate was then added to the flask. The reaction mixture was reacted at room temperature for 3 hours and monitored by thin layer chromatography until the disappearance of the starting materials. The reaction mixture was concentrated under reduced pressure to obtain the title compound (R)-3-amino-1-[1-((S)-3-fluoropyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 26 (140 mg, yield 94%) as a white solid.

MS m/z (ESI): 522.2 [M+1].

$^1$H NMR (400 MHz, CD$_3$OD): δ7.42-7.37 (m, 1H), 7.26-7.22 (m, 1H), 5.47-5.29 (m, 1H), 5.18-5.10 (m, 2H), 4.56-4.48 (m, 1H), 4.37-4.28 (m, 2H), 4.16-3.89 (m, 5H), 3.74-3.68 (m, 1H), 3.16-3.11 (m, 2H), 3.07-2.77 (m, 2H), 2.39-2.03 (m, 2H).

Example 27
(R)-1-(1-Acetyl-3-trifluoromethyl-5,6-dihydro-8H-imidazo[1,5-a]pyrazin-7-yl)-3-amino-4-(2,4,5-trifluoro-phenyl)-butan-1-one hydrochloride
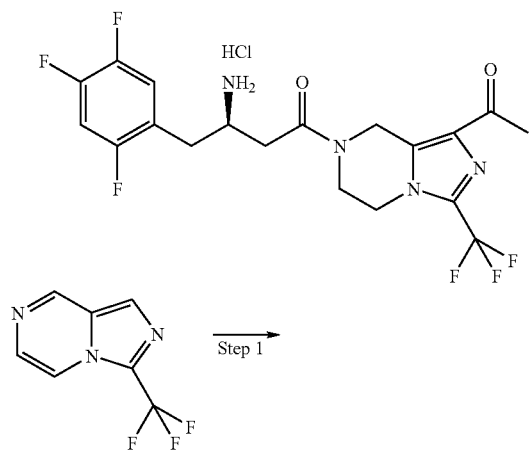
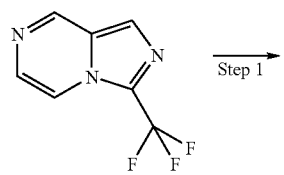
1j
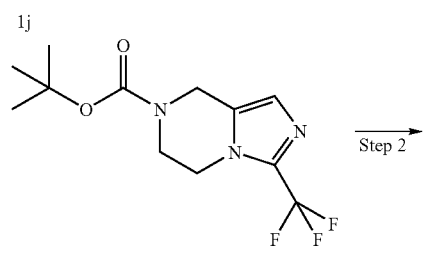
27a
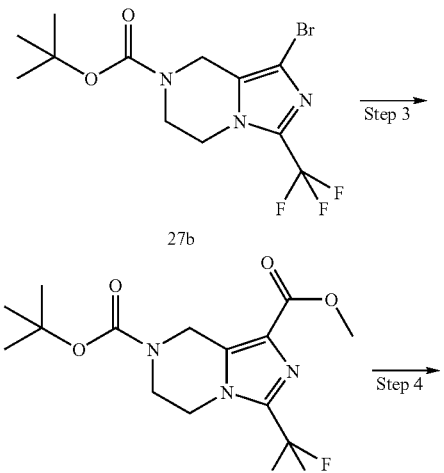
27b
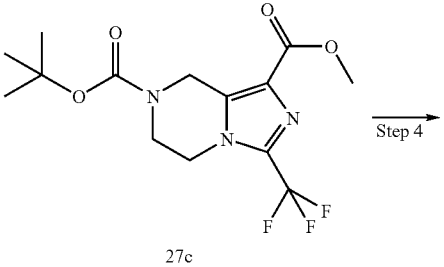
27c
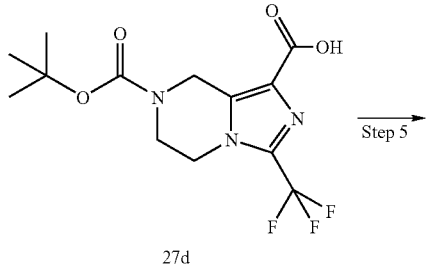
27d
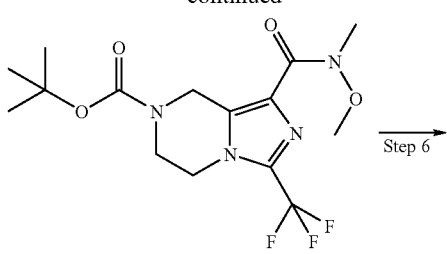
27e
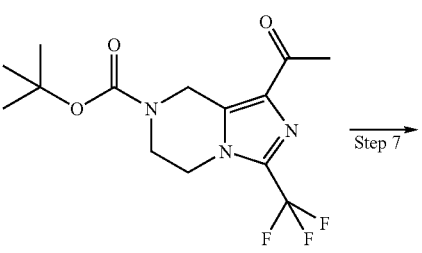
27f
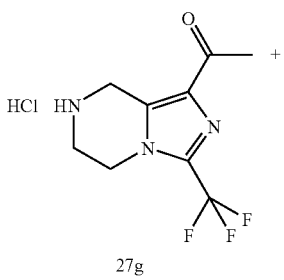
27g
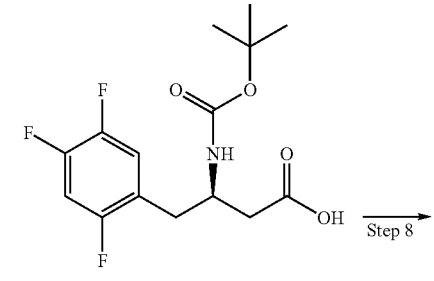
1f
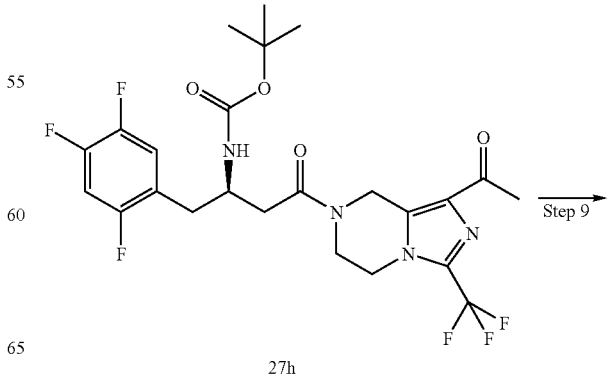
27h

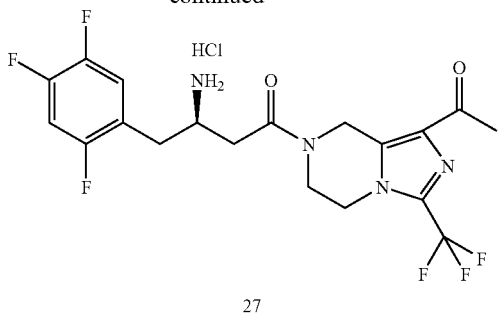

27

Step 1

3-Trifluoromethyl-5,6-dihydro-8H-imidazo[1,5-a]pyrazine-7-carboxylic acid tert-butyl ester 3-Trifluoromethyl-imidazo[1,5-a]pyrazine 1j (3.5 g, 18.7 mmol) was dissolved in 50 mL of ethanol, and 10% Pd/C (0.5 g) was then added to the solution under stirring. The reaction mixture was reacted overnight under a hydrogen atmosphere until the reaction was complete. The reaction mixture was flitered through a pad of Celite, and the filtrate was concentrated under reduced pressure. The resulting residue was washed with 100 mL of ethanol. A solution of di-tert-butyl dicarbonate (6.2 g, 28.1 mmol) in 100 mL of ethanol was then added dropwise to the reaction mixture under stirring. Upon completion of the addition, the reaction mixture was stirred for another 30 minutes until the reaction was complete. The reaction mixture was concentrated under reduced pressure. The resulting residue was purified by silica gel column chromatography to obtain the title compound 3-trifluoromethyl-5,6-dihydro-8H-imidazo[1,5-a]pyrazine-7-carboxylic acid tert-butyl ester 27a (3.7 g, yield 68%) as a white solid.

Step 2

1-Bromo-3-trifluoromethyl-5,6-dihydro-8H-imidazo[1,5-a]pyrazine-7-carboxylic acid tert-butyl ester In a 100 mL dried flask, the compound obtained from the previous step, 3-trifluoromethyl-5,6-dihydro-8H-imidazo[1,5-a]pyrazine-7-carboxylic acid tert-butyl ester 27a (300 mg, 1.04 mmol) was dissolved in 50 mL of ethanol under stirring, and N-bromosuccinimide (369 mg, 2.08 mmol) was then added to the solution. The reaction mixture was stirred at room temperature for an hour until the reaction was complete. The reaction mixture was concentrated under reduced pressure. The resulting residue was purified by silica gel column chromatography to obtain the title compound 1-bromo-3-trifluoromethyl-5,6-dihydro-8H-imidazo[1,5-a]pyrazine-7-carboxylic acid tert-butyl ester 27b (220 mg, yield 57.8%) as a white solid.

Step 3

3-Trifluoromethyl-5,6-dihydro-8H-imidazo[1,5-a]pyrazine-1,7-dicarboxylic acid 7-tert-butyl ester 1-methyl ester Octacarbonyldicobalt (5.54 g, 16.2 mmol) and potassium carbonate (11.2 g, 81.1 mmol) was dissolved in 100 mL of methanol under stirring. The reaction mixture was stirred for 15 minutes at 60° C., and 1-bromo-3-trifluoromethyl-5,6-dihydro-8H-imidazo[1,5-a]pyrazine-7-carboxylic acid tert-butyl ester 27b (3 g, 8.11 mmol) and methyl chloroacetate (5.25 g, 48.6 mmol) were then added to the solution. The reaction mixture was reacted for 6 hours under a carbon monoxide atmosphere and monitored by thin layer chromatography until the disappearance of the starting materials. After cooling to room temperature, the reaction mixture was filtered through a pad of silica gel, rinsed with methanol. The filtrate was concentrated under reduced pressure. The resulting residue was purified by silica gel column chromatography to obtain the title compound 3-trifluoromethyl-5,6-dihydro-8H-imidazo[1,5-a]pyrazine-1,7-dicarboxylic acid 7-tert-butyl ester 1-methyl ester 27c (1.92 g, yield 67%) as a white solid. (Reference: *J. Organomet. Chem,* 1985, 293)

MS m/z (ESI): 350.5 [M+1].

Step 4

3-Trifluoromethyl-5,6-dihydro-8H-imidazo[1,5-a]pyrazine-1,7-dicarboxylic acid 7-tert-butyl ester 3-Trifluoromethyl-5,6-dihydro-8H-imidazo[1,5-a]pyrazine-1,7-dicarboxylic acid 7-tert-butyl ester 1-methyl ester 27c (1.92 g, 5.5 mmol) was dissolved in 50 mL of methanol under stirring, and 30 mL of 4 N sodium hydroxide was then added to the solution. The reaction mixture was reacted for 30 minutes at room temperature and monitored by thin layer chromatography until the disappearance of the starting materials. The mixture was adjusted to pH 4-5 with 2 N hydrochloric acid, and then extracted with ethyl acetate (100 mL×3). The combined organic phase was dried over anhydrous magnesium sulfate, filtered and concentrated under reduced pressure to obtain the title compound 3-trifluoromethyl-5,6-dihydro-8H-imidazo[1,5-a]pyrazine-1,7-dicarboxylic acid 7-tert-butyl ester 27d (2 g) as a white solid, which was directly used in the next step.

Step 5

1-(Methoxy-methyl-carbamoyl)-3-trifluoromethyl-5,6-dihydro-8H-imidazo[1,5-a]pyrazine-7-carboxylic acid tert-butyl ester 3-Trifluoromethyl-5,6-dihydro-8H-imidazo[1,5-a]pyrazine-1,7-dicarboxylic acid 7-tert-butyl ester 27d (1.84 g, 5.5 mmol) and N-methoxy methyl-amine (0.805 g, 8.25 mmol) were dissolved in 50 mL of dichloromethane under stirring, and triethylamine (3 mL, 22 mmol) and bis(2-oxo-3-oxazolidinyl)phosphinic chloride (2.1 g, 8.25 mmol) were then added to the solution. The reaction mixture was reacted overnight at room temperature and monitored by thin layer chromatography until the disappearance of the starting materials. The reaction mixture was concentrated under reduced pressure. The resulting residue was purified by silica gel column chromatography to obtain the title compound 1-(methoxy-methyl-carbamoyl)-3-trifluoromethyl-5,6-dihydro-8H-imidazo[1,5-a]pyrazine-7-carboxylic acid tert-butyl ester 27e (2.1 g) as a white solid.

MS m/z (ESI): 379.1 [M+1].

Step 6

1-Acetyl-3-trifluoromethyl-5,6-dihydro-8H-imidazo[1,5-a]pyrazine-7-carboxylic acid tert-butyl ester 1-(Methoxy-methyl-carbamoyl)-3-trifluoromethyl-5,6-dihydro-8H-imidazo[1,5-a]pyrazine-7-carboxylic acid tert-butyl ester 27e (0.3 g, 0.79 mmol) was dissolved in 20 mL of tetrahydrofuran under stirring, and methylmagnesium bromide (1.13 mL, 1.58 mmol) was then added dropwise to the solution at 0° C. The reaction mixture was reacted at 0° C. for 1.5 hours and monitored by thin layer chromatography until the disappearance of the starting materials. 50 mL of saturated ammonium chloride and 10 mL of saturated brine were added to the reaction mixture. The mixture was extracted with ethyl acetate (50 mL×3). The combined organic phase was dried with anhydrous magnesium sulfate, filtered and concentrated under reduced pressure. The resulting residue was purified by silica gel column chromatography to obtain the title compound 1-acetyl-3-trifluoromethyl-5,6-dihydro-8H-imidazo[1,5-a]pyrazine-7-carboxylic acid tert-butyl ester 27f (0.24 g, yield 90%) as a yellow oil.

MS m/z (ESI): 334.0 [M+1].

Step 7

1-(3-Trifluoromethyl-5,6,7,8-tetrahydro-imidazo[1,5-a]pyrazin-1-yl)-ethanone

1-Acetyl-3-trifluoromethyl-5,6-dihydro-8H-imidazo[1,5-a]pyrazine-7-carboxylic acid tert-butyl ester 27f (0.24 g, 0.72 mmol) was dissolved in a little ethyl acetate. A solution of 2.7 N hydrochloric acid in 5 mL of ethyl acetate was then added. The reaction mixture was reacted at room temperature and monitored by thin layer chromatography until the disappearance of the starting materials. The reaction mixture was concentrated under reduced pressure to obtain the title compound 1-(3-trifluoromethyl-5,6,7,8-tetrahydro-imidazo[1,5-a]pyrazin-1-yl)-ethanone 27g, which was directly used in the next step.

Step 8

(R)-[3-(1-Acetyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 1-(3-Trifluoromethyl-5,6,7,8-tetrahydro-imidazo[1,5-a]pyrazin-1-yl)-ethanone 27g (192 mg, 0.72 mmol) and (R)-3-tert-butoxycarbonylamino-4-(2,4,5-trifluoro-phenyl)-butyric acid 1f (0.24 g, 0.72 mmol) were dissolved in 20 mL of dichloromethane under stirring, and triethylamine (0.4 mL, 2.88 mmol) was then added to the solution. After stirring to mix well, bis(2-oxo-3-oxazolidinyl)phosphinic chloride (0.275 g, 1.08 mmol) was then added. The reaction mixture was reacted overnight at room temperature and monitored by thin layer chromatography until the disappearance of the starting materials. The reaction mixture was concentrated under reduced pressure. The resulting residue was purified by silica gel column chromatography to obtain the title compound (R)-[3-(1-acetyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 27h (0.3 g) as a white solid.

MS m/z (ESI): 449.2 [M+1].

Step 9

(R)-1-(1-Acetyl-3-trifluoromethyl-5,6-dihydro-8H-imidazo[1,5-a]pyrazin-7-yl)-3-amino-4-(2,4,5-trifluoro-phenyl)-butan-1-one hydrochloride (R)-[3-(1-Acetyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 27h (0.3 g, 0.55 mmol) was dissolved in 2 mL of ethyl acetate under stirring. A solution of 2.4 N hydrochloric acid in 5 mL of ethyl acetate was then added to the above solution. The reaction mixture was reacted at room temperature and monitored by thin layer chromatography until the disappearance of the starting materials. The reaction mixture was concentrated under reduced pressure. The resulting residue was purified by silica gel column chromatography to obtain the title compound (R)-1-(1-acetyl-3-trifluoromethyl-5,6-dihydro-8H-imidazo[1,5-a]pyrazin-7-yl)-3-amino-4-(2,4,5-trifluoro-phenyl)-butan-1-one hydrochloride 27 (0.15 g, yield 57%) as a white solid.

MS m/z (ESI): 548.9 [M+1].

$^1$H NMR (400 MHz, CD$_3$OD): δ 7.37 (m, 1H), 7.26 (m, 1H), 5.09 (m, 1H), 5.02 (d, 1H), 4.87-3.92 (m, 5H), 3.1-2.78 (m, 4H), 2.57 (d, 2H), 2.04 (d, 1H).

Example 28

(R)-3-Amino-1-(1-cyclopentanecarbonyl-3-trifluoromethyl-5,6-dihydro-8H-imidazo[1,5-a]pyrazin-7-yl)-4-(2,4,5-trifluoro-phenyl)-butan-1-one hydrochloride

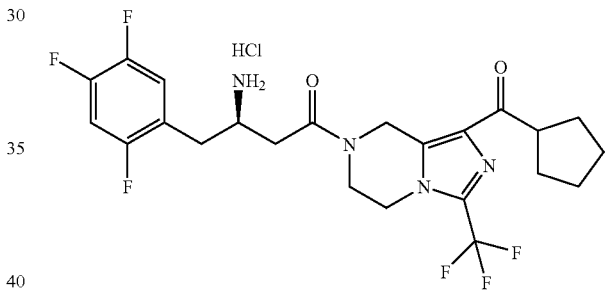

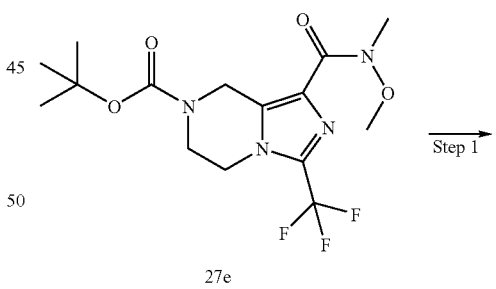

27e

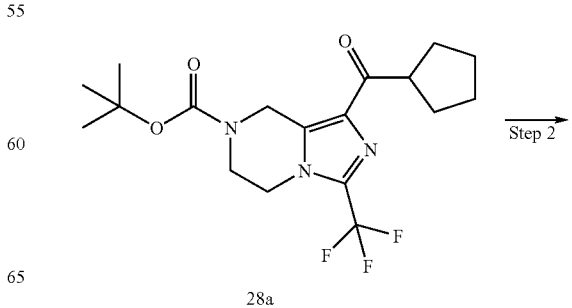

28a

-continued

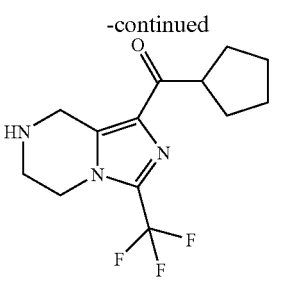

28b

+

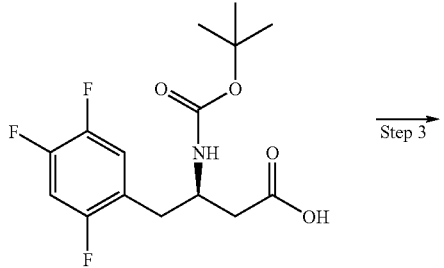

1f

Step 3 →

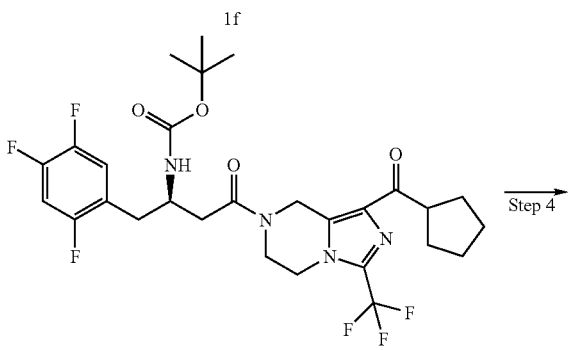

28c

Step 4 →

28

Step 1

1-Cyclopentanecarbonyl-3-trifluoromethyl-5,6-dihydro-8H-imidazo[1,5-a]pyrazine-7-carboxylic acid tert-butyl ester 1-(Methoxy-methyl-carbamoyl)-3-trifluoromethyl-5,6-dihydro-8H-imidazo[1,5-a]pyrazine-7-carboxylic acid tert-butyl ester 27e (0.3 g, 0.79 mmol) was dissolved in 20 mL of tetrahydrofuran under stirring, and then cyclopentylmagnesium bromide (0.79 mL, 1.58 mmol) was added dropwise to the solution at 0° C. The reaction mixture was stirred at 0° C. for 3 hours and monitored by thin layer chromatography until the disappearance of the starting materials. 50 mL of saturated ammonium chloride and 10 mL of saturated brine were added. The crude mixture was extracted with ethyl acetate (100 mL×3), and then the combined organic phase was dried with anhydrous magnesium sulfate, filtered and concentrated under reduced pressure. The resulting residue was purified by silica gel column chromatography to obtain the title compound 1-cyclopentanecarbonyl-3-trifluoromethyl-5,6-dihydro-8H-imidazo[1,5-a]pyrazine-7-carboxylic acid tert-butyl ester 28a (0.1 g, yield 30%) as a yellow oil.

MS m/z (ESI): 388.1 [M+1].

Step 2

Cyclopentyl-(3-trifluoromethyl-5,6,7,8-tetrahydro-imidazo[1,5-a]pyrazin-1-yl)-methanone 1-Cyclopentanecarbonyl-3-trifluoromethyl-5,6-dihydro-8H-imidazo[1,5-a]pyrazine-7-carboxylic acid tert-butyl ester 28a (0.1 g, 0.258 mmol) was dissolved in a little ethyl acetate under stirring. A solution of 2.7 N hydrochloric acid in 5 mL of ethyl acetate was then added. The reaction mixture was reacted at room temperature for 2 hours and monitored by thin layer chromatography until the disappearance of the starting materials. The reaction mixture was concentrated under reduced pressure to obtain the title compound cyclopentyl-(3-trifluoromethyl-5,6,7,8-tetrahydro-imidazo[1,5-a]pyrazin-1-yl)-methanone 28b, which was directly used in the next step.

MS m/z (ESI): 288.2 [M+1].

Step 3

(R)-[3-(1-Cyclopentanecarbonyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester Cyclopentyl-(3-trifluoromethyl-5,6,7,8-tetrahydro-imidazo[1,5-a]pyrazin-1-yl)-methanone 28b (83 mg, 0.258 mmol) and (R)-3-tert-butoxycarbonylamino-4-(2,4,5-trifluoro-phenyl)-butyric acid if (0.129 g, 0.388 mmol) were dissolved in 10 mL of dichloromethane under stirring, and triethylamine (0.143 mL, 1.03 mmol) was then added to the solution. After stirring to mix well, bis(2-oxo-3-oxazolidinyl)phosphinic chloride (0.099 g, 0.388 mmol) was added. The reaction mixture was reacted overnight at room temperature and monitored by thin layer chromatography until the disappearance of the starting materials. The reaction mixture was concentrated under reduced pressure. The resulting residue was purified by silica gel column chromatography to obtain the title compound (R)-[3-(1-cyclopentanecarbonyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 28c (0.11 g, yield 72%) as an orange oil.

MS m/z (ESI): 602.9 [M+1].

Step 4

(R)-3-Amino-1-(1-cyclopentanecarbonyl-3-trifluoromethyl-5,6-dihydro-8H-imidazo[1,5-a]pyrazin-7-yl)-4-(2,4,5-trifluoro-phenyl)-butan-1-one hydrochloride (R)-[3-(1-Cyclopentanecarbonyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 28c (0.11 g, 0.183 mmol) was dissolved in 2 mL of ethyl acetate under stirring. A solution of 2.4 N hydrochloric acid in 5 mL of ethyl acetate was added to the above solution. The reaction mixture was stirred at room temperature and monitored by thin layer chromatography until the disappearance of the starting materials.

The reaction mixture was concentrated under reduced pressure. The resulting residue was purified by silica gel column chromatography to obtain the title compound (R)-3-amino-1-(1-cyclopentanecarbonyl-3-trifluoromethyl-5,6-dihydro-8H-imidazo[1,5-a]pyrazin-7-yl)-4-(2,4,5-trifluoro-phenyl)-butan-1-one hydrochloride 28 (80 mg, yield 81%) as a yellow solid.

MS m/z (ESI): 503.2 [M+1].

$^1$H NMR (400 MHz, CD$_3$OD): δ 7.41 (m, 1H), 7.25 (m, 1H), 5.10 (d, 1H), 4.87 (s, 1H), 4.37-3.91 (m, 6H), 3.14-2.82 (m, 4H), 2.03-1.72 (m, 8H).

Example 29

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (2-dimethylamino-ethyl)-amide dihydrochloride

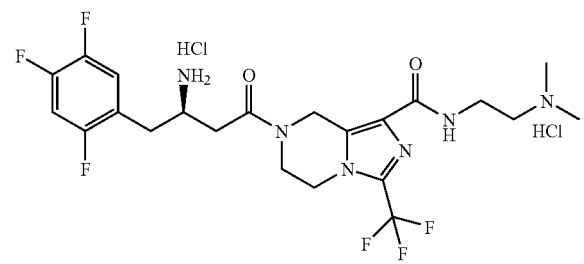

2a

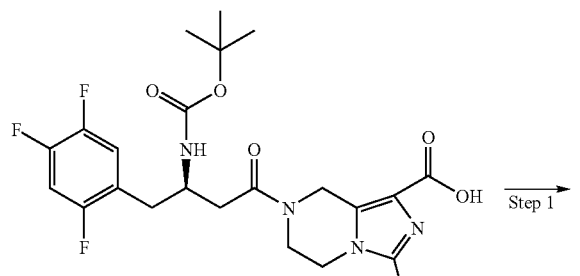

29a

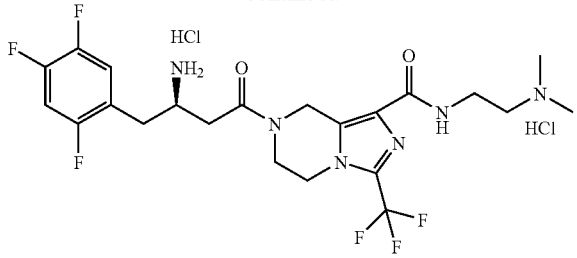

29

Step 1

(R)-[3-[1-(2-Dimethylamino-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), bis(2-oxo-3-oxazolidinyl)phosphinic chloride (0.14 g, 0.54 mmol) and triethylamine (0.25 mL, 1.62 mmol) were dissolved in 10 mL of dichloromethane under stirring, and N,N'-dimethylethane-1,2-diamine (48 mg, 0.54 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-(2-dimethylamino-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 29a (0.1 g) as a white solid.

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (2-dimethylamino-ethyl)-amide dihydrochloride (R)-[3-[1-(2-Dimethylamino-ethylcarbamoyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 29a (0.10 g, 0.16 mmol) was dissolved in 2 mL of ethyl acetate under stirring. A solution of 2.4 N hydrochloric acid in 6 mL of ethyl acetate was then added to the above solution. The reaction mixture was reacted at room temperature for 4 hours and monitored by thin layer chromatography until the disappearance of the starting materials. The reaction mixture was concentrated under reduced pressure, and 5 mL of ethyl acetate was added to the residue and filtered. The resulting white solid was rinsed with ethyl acetate to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (2-dimethylamino-ethyl)-amide dihydrochloride 29 (80 mg, yield 63%) as a white solid.

$^1$H NMR (400 MHz, CD$_3$OD): δ7.46-7.39 (m, 1H), 7.29-7.23 (m, 1H), 5.18-5.09 (m, 2H), 4.37-4.27 (m, 2H), 4.15-

4.09 (m, 1H), 4.00-3.95 (m, 1H), 3.77-3.75 (m, 2H), 3.39-3.35 (m, 2H), 3.13-3.12 (m, 2H), 3.02 (s, 3H), 3.01 (m, 4H), 2.98-2.88 (m, 1H).

Example 30

(R)-3-Amino-1-[1-((S)-2-hydroxymethyl-pyrrolidine-1-carbonyl)-3-trifluoromethyl-5,6-dihydro-8H-imidazo[1,5-a]pyrazin-7-yl]-4-(2,4,5-trifluorophenyl)-butan-1-one hydrochloride

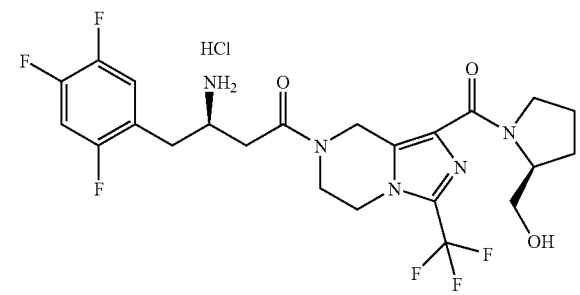

2a

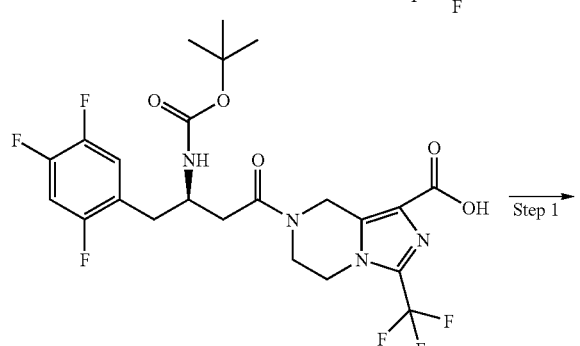

30a

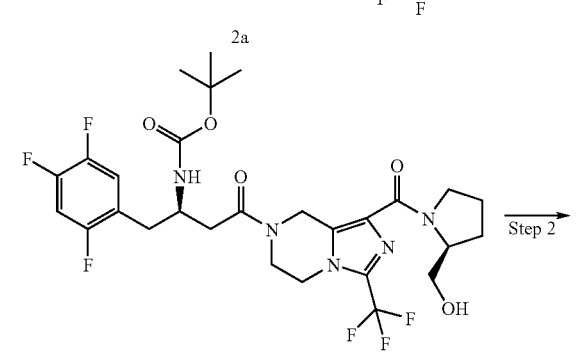

30

Step 1

(R)-[3-[1-((S)-2-Hydroxymethyl-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), (S)-pyrrolidin-2-ylmethanol (54.62 mg, 0.54 mmol) and triethylamine (0.25 mL, 1.62 mmol) were dissolved in 10 mL of dichloromethane under stirring, and bis(2-oxo-3-oxazolidinyl)phosphinic chloride (0.14 g, 0.54 mmol) was then added to the solution. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-[3-[1-((S)-2-hydroxymethyl-pyrrolidine-1-carbonyl)-3-trifluoromethyl-5,6-dihydro-8H-imidazo[1,5-a]pyrazin-7-yl]-3-oxo-1-(2,4,5-trifluoro-benzyl)-propyl]-carbamic acid tert-butyl ester 30a (0.2 g) as a white solid.

Step 2

(R)-3-Amino-1-[1-((S)-2-hydroxymethyl-pyrrolidine-1-carbonyl)-3-trifluoromethyl-5,6-dihydro-8H-imidazo[1,5-a]pyrazin-7-yl]-4-(2,4,5-trifluorophenyl)-butan-1-one hydrochloride (R)-[3-[1-((S)-2-Hydroxymethyl-pyrrolidine-1-carbonyl)-3-trifluoromethyl-5,6-dihydro-8H-imidazo[1,5-a]pyrazin-7-yl]-3-oxo-1-(2,4,5-trifluorobenzyl)-propyl]-carbamic acid tert-butyl ester 30a (0.16 g, 0.25 mmol) and 2 mL of dichloromethane were added into the reaction flask. A solution of 2.7 N hydrochloric acid in 5 mL of methanol was then added to the flask. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-3-amino-1-[1-((S)-2-hydroxymethyl-pyrrolidine-1-carbonyl)-3-trifluoromethyl-5,6-dihydro-8H-imidazo[1,5-a]pyrazin-7-yl]-4-(2,4,5-trifluoro-phenyl)-butan-1-one hydrochloride 30 (120 mg, yield 84%) as a white solid.

$^1$H NMR (400 MHz, CD$_3$OD): δ7.34-7.30 (m, 1H), 7.19-7.12 (m, 1H), 5.10-4.92 (m, 2H), 4.27-4.25 (m, 2H), 4.21-4.18 (m, 1H), 4.06-3.98 (m, 2H), 3.91-3.90 (m, 1H), 3.84-3.80 (m, 1H), 3.72-3.48 (m, 3H), 3.03-2.99 (m, 2H), 2.93-2.73 (m, 2H), 2.01-1.85 (m, 4H).

Example 31

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride

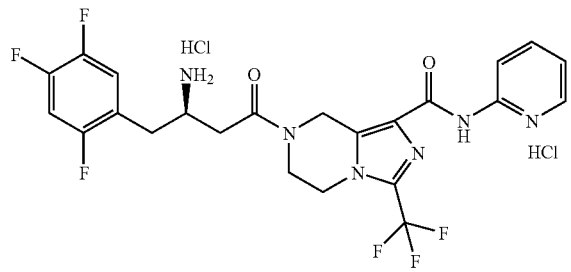

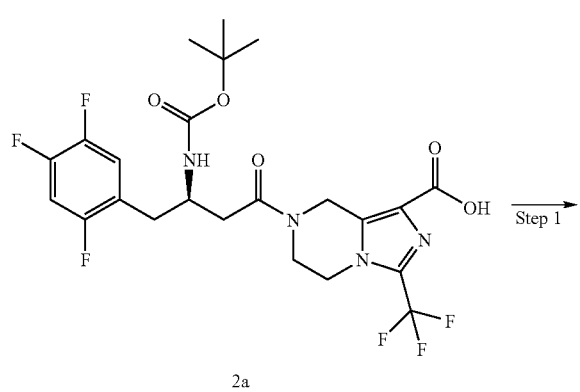

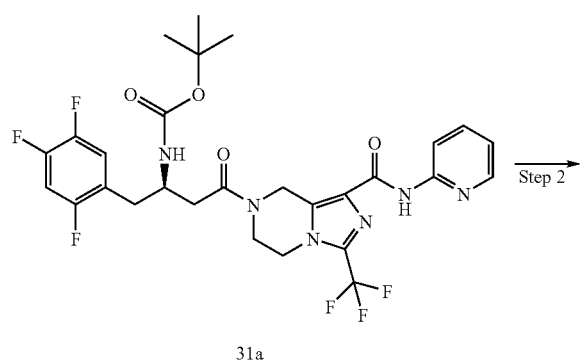

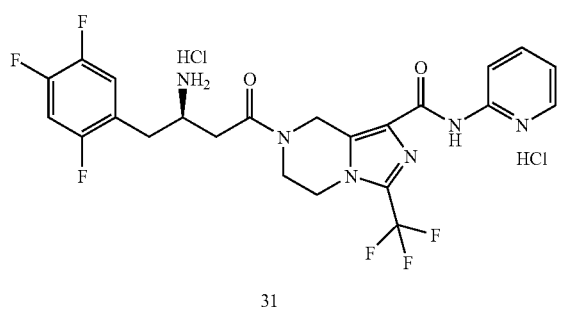

Step 1

(R)-[3-oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), 2-aminopyridine (51 g, 0.54 mmol) and triethylamine (0.25 mL, 1.62 mmol) were dissolved in 10 mL of dichloromethane under stirring. After stirring for 20 minutes, bis(2-oxo-3-oxazolidinyl)phosphinic chloride (0.14 g, 0.54 mmol) was added to the solution. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-[3-oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 31a (0.1 g, yield 59%) as a white solid.

MS m/z (ESI): 627.1 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride (R)-[3-oxo-3-[1-(pyridin-2-ylcarbamoyl)-3-trifluoromethyl-5,6-dihydro-8H-imidazo[1,5-a]pyrazin-7-yl]-1-(2,4,5-trifluoro-benzyl)-propyl]-carbamic acid tert-butyl ester 31a (0.10 g, 0.16 mmol) and 2 mL of dichloromethane were added into the reaction flask. A solution of 2.7 N hydrochloric acid in 5 mL of methanol was added to the flask. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (pyridin-2-yl)amide dihydrochloride 31(80 mg, yield 95.2%) as a white solid.

MS m/z (ESI): 527.1 [M+1].

$^1$H NMR (400 MHz, CD$_3$OD): δ8.48 (m, 2H), 8.08-8.05 (m, 1H), 7.65-7.63 (m, 1H), 7.45-7.41 (m, 1H), 7.27-7.26 (m, 1H), 5.24-5.17 (m, 2H), 4.43-4.34 (m, 2H), 4.14 (m, 1H), 4.05 (m, 1H), 3.96 (m, 1H), 3.21-3.03 (m, 2H), 2.96-2.72 (m, 2H).

Example 32

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (4-fluoro-phenyl)-amide hydrochloride

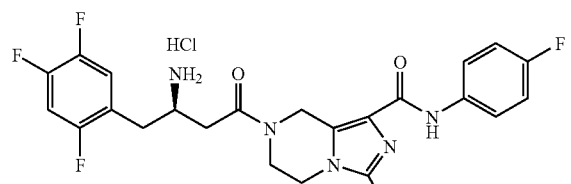

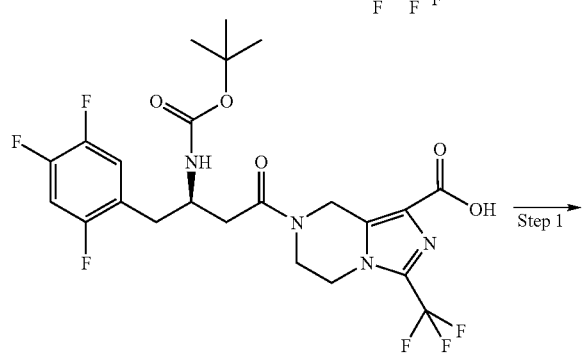

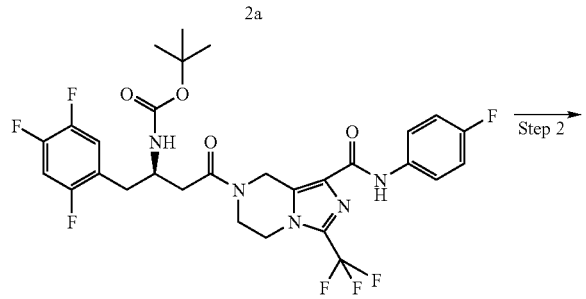

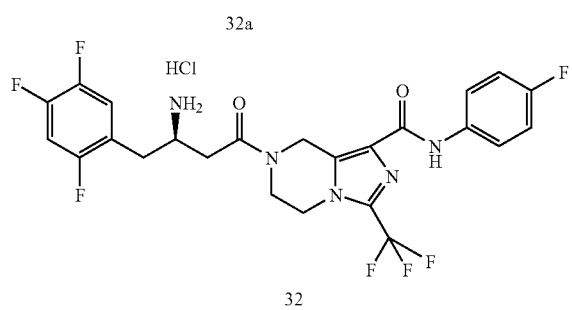

Step 1

(R)-4-(1-(4-Fluoro-phenylcarbamoyl)-3-trifluoromethyl-5,6-dihydro-8H-imidazo[1,5-a]pyrazin-7-yl)-3-oxo-1-(2,4,5-trifluoro-benzyl)-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.15 g, 0.27 mmol), bis(2-oxo-3-oxazolidinyl)phosphinic chloride (0.14 g, 0.54 mmol) and triethylamine (0.25 mL, 1.62 mmol) were dissolved in 10 mL of dichloromethane under stirring, and 4-fluoroaniline (0.06 g, 0.54 mmol) was then added by one time to the solution. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-4-(1-(4-fluoro-phenylcarbamoyl)-3-trifluoromethyl-5,6-dihydro-8H-imidazo[1,5-a]pyrazin-7-yl)-3-oxo-1-(2,4,5-trifluoro-benzyl)-carbamic acid tert-butyl ester 32a (0.12 g, yield 69%) as a white solid.

MS m/z (ESI): 643.9 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (4-fluoro-phenyl)-amide hydrochloride (R)-4-(1-(4-Fluoro-phenylcarbamoyl)-3-trifluoromethyl-5,6-dihydro-8H-imidazo[1,5-a]pyrazin-7-yl)-3-oxo-1-(2,4,5-trifluoro-benzyl)-carbamic acid tert-butyl ester 32a (0.12 g, 0.186 mmol) and 2 mL of ethyl acetate were added into the reaction flask. A solution of 2.7 N hydrochloric acid in 8 mL of ethyl acetate was then added to the flask. The reaction mixture was stirred at room temperature overnight and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (4-fluoro-phenyl)-amide hydrochloride 32 (110 mg, yield 100%) as a white solid.

MS m/z (ESI): 544.1 [M+1].

$^1$H NMR (400 MHz, DMSO): δ10.124 (d, 1H), 8.190 (s, 2H), 7.849 (s, 1H), 7.552 (m, 1H), 7.157 (d, 2H), 5.023 (m, 2H), 4.231 (m, 2H), 3.897 (m, 3H), 3.014 (m, 4H), 2.0 (m, 2H).

Example 33

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid benzyl ester hydrochloride

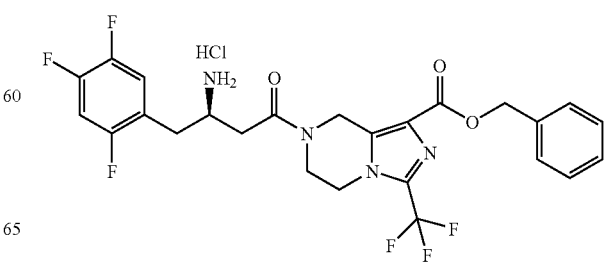

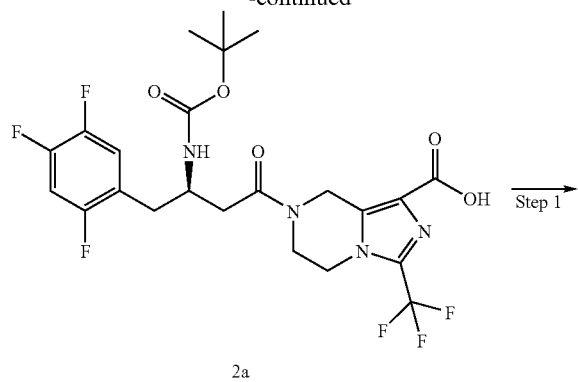

2a

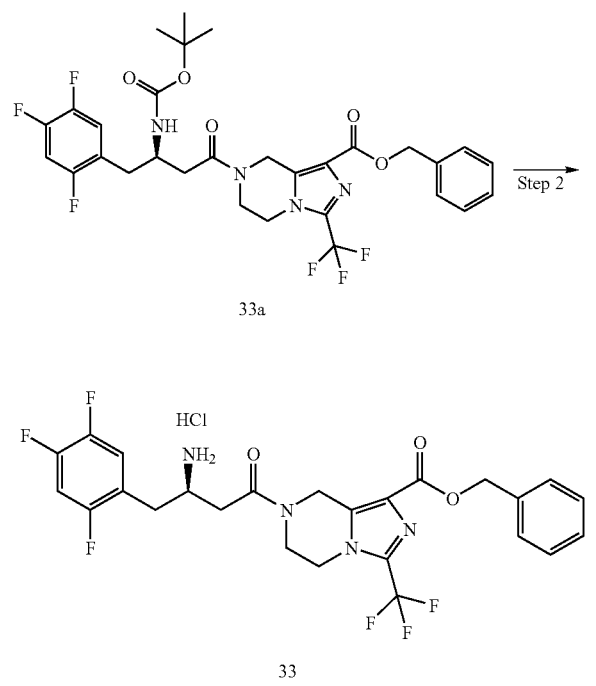

33a

33

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid benzyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.24 g, 0.44 mmol), 1-hydroxybenzotriazole (0.072 g, 0.53 mmol) and N-(3-dimethylaminopropyl)-N'-ethylcarbodiimide hydrochloride (0.102 g, 0.53 mmol) were dissolved in 10 mL of dichloromethane under stirring, and benzyl alcohol (0.1 mL, 0.88 mmol) was then added to the solution. The reaction mixture was reacted at room temperature overnight and monitored by thin layer chromatography until the disappearance of the starting materials. The reaction mixture was concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid benzyl ester 33a (0.056 g, yield 20%) as a white solid.

MS m/z (ESI): 640.9 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid benzyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid benzyl ester 33a (0.056 g, 0.087 mmol) and a solution of 2.7 N hydrochloric acid in 2 mL of ethyl acetate were added into the reaction flask. The reaction mixture was stirred at room temperature for 2 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid benzyl ester hydrochloride 33 (0.043 g, yield 86%) as a white solid.

MS m/z (ESI): 541.2 [M+1].

$^1$H NMR (400 MHz, CD$_3$OD): 7.526-7.498 (m, 2H), 7.498-7.364 (m, 5H), 5.415 (s, 2H), 5.121-5.003 (m, 2H), 4.498-3.820 (m, 5H), 3.341-2.903 (m, 4H).

Example 34

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester hydrochloride

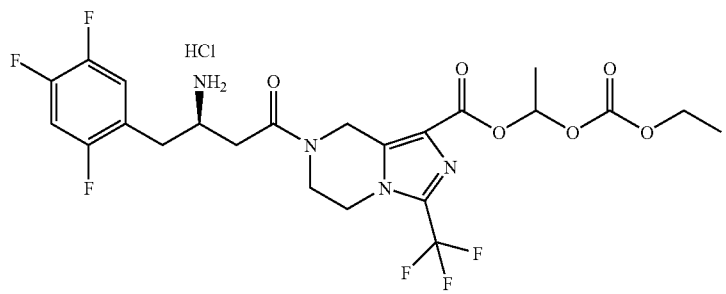

-continued

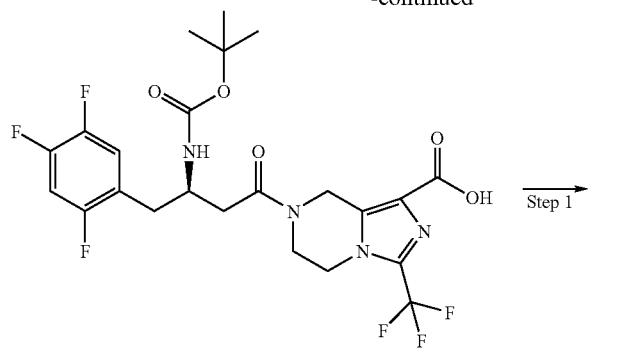

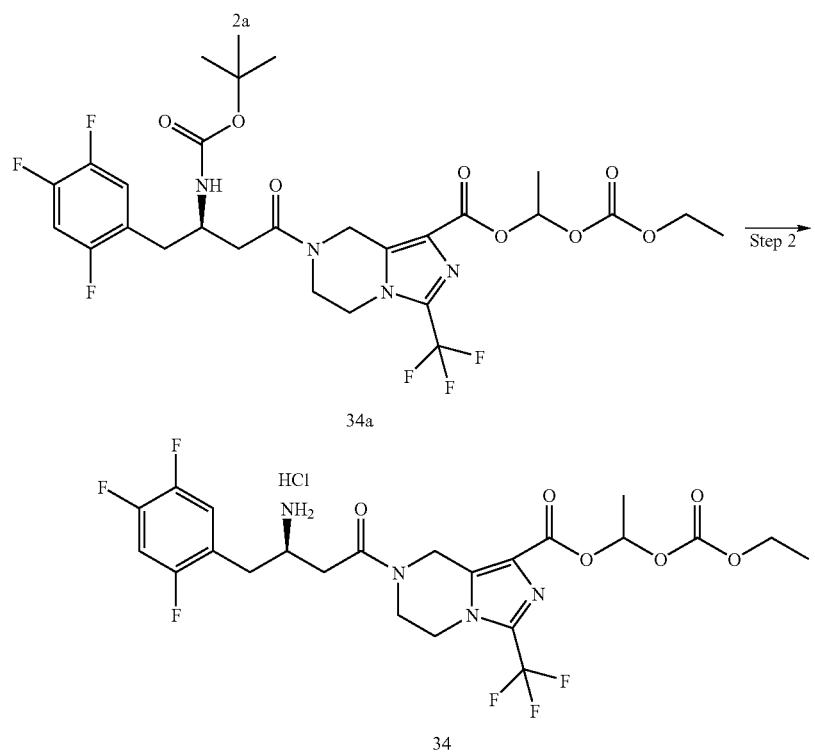

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.275 g, 0.5 mmol) and 4 mL of N,N-dimethylformamide were added into the reaction tube, and then 1-chloroethyl ethyl carbonate (0.092 g, 0.6 mmol), potassium iodide (0.0415 g, 0.25 mmol) and potassium carbonate (0.083 g, 0.6 mmol) were added successively under stirring. Then the reaction tube was sealed up. The reaction mixture was reacted at 65° C. in an oil bath for 2 hours and monitored by thin layer chromatography until the disappearance of the starting materials. After cooling to room temperature, 40 mL of water was added to the reaction tube. The reaction mixture was extracted with ethyl acetate (25 mL×3), and the combined organic phase was washed with water (20 mL×2), dried over anhydrous magnesium sulfate, filtered and concentrated under reduced pressure. The resulting residue was purified by silica gel column chromatography to obtain the title compound, (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester 34a (0.26 g, yield 78.1%) as a white solid.

MS m/z (ESI): 666.9 [M+1], 689.1 [M+23].

$^1$H NMR (400 MHz, CDCl$_3$): δ7.08 (m, 2H), 6.90 (m, 1H), 5.36 (m, 1H), 5.15 (m, 1H), 5.01 (m, 1H), 4.27-3.94 (m, 6H), 3.0 (m, 2H), 2.68 (m, 1H), 1.71 (d, 3H), 1.61 (s, 2H), 1.40 (s, 9H).

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester 34a (0.26 g, 0.39 mmol) and 5 mL of ethyl acetate were added into the reaction flask. A solution of 6.5 N hydrochloric acid in 3 mL of ethyl acetate was then added to the flask. The reaction mixture was stirred at room temperature for 6 hours and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid (1-ethoxycarbonyloxy)-ethyl ester hydrochloride 34 (0.2 g, yield 85%) as a white solid.

MS m/z (ESI): 567.0 [M+1].

$^1$H NMR (400 MHz, CD$_3$OD): δ7.30 (m, 1H), 7.15 (m, 1H), 6.96 (m, 1H), 5.06 (m, 2H), 4.32 (t, 1H), 4.24 (m, 3H), 4.03 (m, 2H), 3.60 (m, 1H), 2.88 (d, 2H), 2.67 (m, 2H), 1.93 (s, 1H), 1.65 (t, 31-1).

Example 35

R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid isopropyl ester hydrochloride

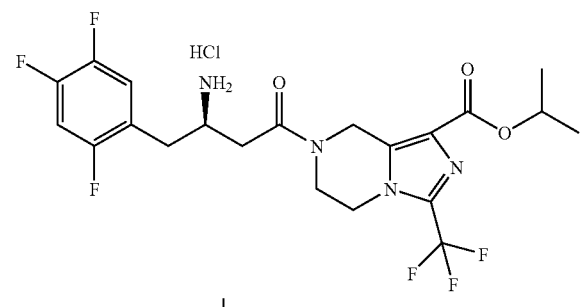

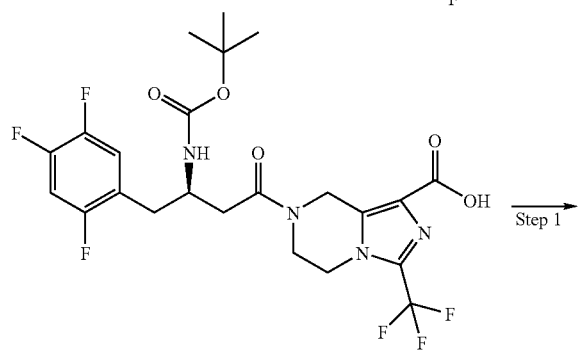

2a

35a

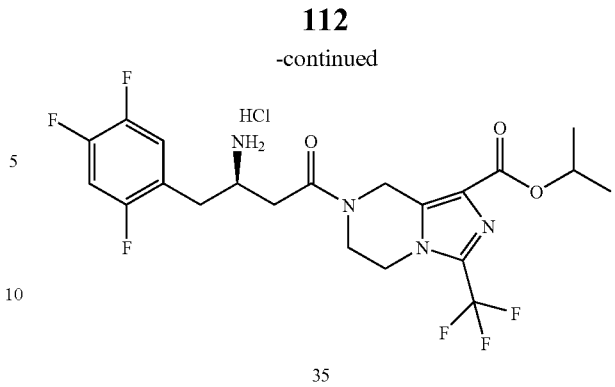

35

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid isopropyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.3 g, 0.54 mmol) was added into a 50 mL reaction flask, followed by addition of 10 mL of dichloromethane, 2 mL of isopropanol and 0.3 mL of triethylamine. After stirring for 1 minutes, bis(2-oxo-3-oxazolidinyl)phosphinic chloride (0.277 g, 1.09 mmol) was added to the solution. The reaction mixture was stirred at room temperature for 2 hours, and then 10 mL of isopropanol and isopropoxysodium (0.177 g, 2.16 mmol) were added. The reaction mixture was stirred at room temperature for 1.5 hours and monitored by thin layer chromatography until the disappearance of the starting materials. 10 mL of saturated ammonium chloride was added to the reaction mixture, and white precipitates were formed. The precipitates were filtered through a pad of silica gel, and 50 mL of water was added to the filtrate. The filtrate was extracted with ethyl acetate (25 mL×5), and the combined organic phase was washed with 30 mL of saturated brine, dried over anhydrous sodium sulfate, filtered and concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid isopropyl ester 35a (0.185 g, yield 57.8%) as a white solid.

MS m/z (ESI): 593.0 [M+1].

$^1$HNMR (400 MHz, CDCl$_3$): δ7.146-7.082 (m, 1H), 6.929-6.883 (m, 1H), 5.405-5.010 (m, 3H), 4.219-3.937 (m, 5H), 3.022-2.307 (m, 4H), 1.484-1.242 (m, 15H).

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid isopropyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid isopropyl ester 35a (0.17 g, 0.29 mmol) and 10 mL of ethyl acetate were added into the reaction flask. A solution of 5.5 N hydrochloric acid in 5 mL of ethyl acetate was then added to the reaction flask in an ice-water bath. Upon completion of the addition, the ice-water bath was removed. The reaction mixture was stirred at room temperature for 2 hours and monitored by thin layer chromatography until the disappearance of the starting materials. The reaction mixture was concentrated under reduced pressure, and washed with n-hexane (10 mL×2). The filtrate was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid isopropyl ester hydrochloride 35 (0.15 g, yield 97.8%) as a white solid.

MS m/z (ESI): 493.1 [M+1].

¹H NMR (400 MHz, DMSO): δ7.631-7.482 (m, 2H), 5.159-4.308 (m, 3H), 4.285-3.742 (m, 5H), 3.110-2.735 (m, 4H), 1.473-1.063 (m, 6H).

Example 36

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid tert-butyl ester hydrochloride

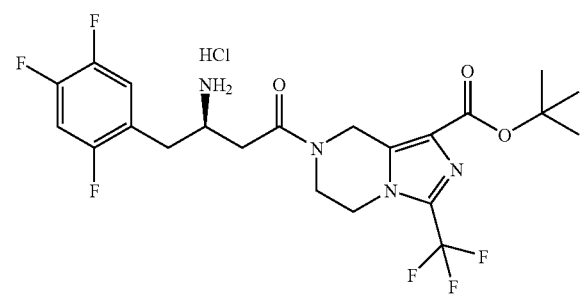

2a

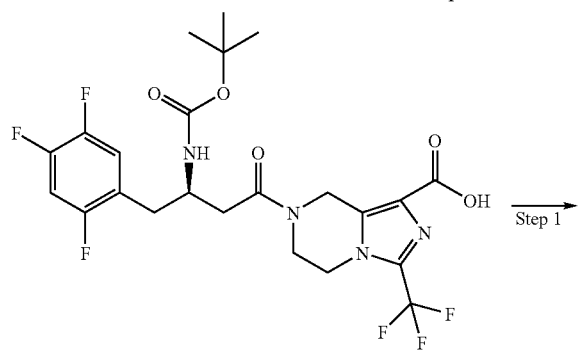

36a

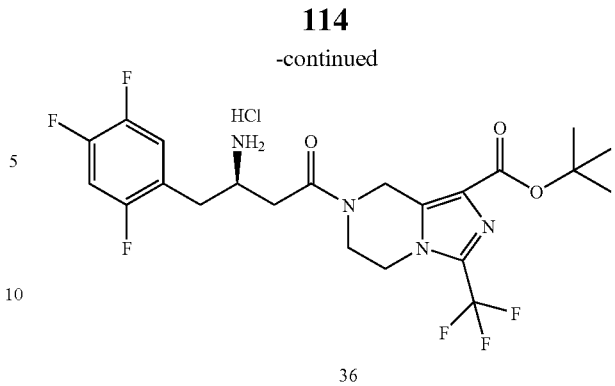

36

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.3 g, 0.54 mmol), 10 mL of dichloromethane and 5 mL of tert-butanol were added into a 100 mL reaction flask, followed by addition of 0.3 mL of triethylamine and bis(2-oxo-3-oxazolidinyl)phosphinic chloride (0.277 g, 1.09 mmol) under stirring. After stirring at room temperature for 2 hours, 10 mL of tert-butanol and potassium tert-butoxide (0.24 g, 2.16 mmol) were added to the solution. The reaction mixture was stirred at room temperature for another 2 hours and monitored by thin layer chromatography until the disappearance of the starting materials. 10 mL of statured ammonium chloride was added to the reaction mixture and white precipitates were formed. The precipitates were filtered through a pad of 100-200 mesh silica gel and 50 mL of water was added to the filtrate. Then the filtrate was extracted with ethyl acetate (25 mL×5). The combined organic phase was washed with 30 mL of saturated brine, dried over anhydrous sodium sulfate, filtered and concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid tert-butyl ester 36a (0.11 g, yield 33.6%) as a white solid.

MS m/z (ESI): 629.2 [M+23].

¹H NMR (400 MHz, CH₃OD): δ7.255-7.090 (m, 2H), 5.077-4.964 (m, 2H), 4.500-4.227 (m, 3H), 4.227-4.032 (m, 2H), 2.994-2.744 (m, 4H), 1.496-1.202 (m, 18H).

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid tert-butyl ester hydrochloride (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid tert-butyl ester 36a (0.094 g, 0.15 mmol) and 10 mL of ethyl acetate were added into the reaction flask. A solution of 5.5 N hydrochloric acid in 3 mL of ethyl acetate was added to the reaction flask in a ice-water bath. Upon completion of the addition, the ice-water bath was removed. The reaction mixture was stirred at room temperature for 3 hours and monitored by thin layer chromatography until the disappearance of the starting materials. The reaction mixture was concentrated under reduced pressure, and washed with 20 mL of n-hexane. The filtrate was concentrated under reduced pressure to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid tert-butyl ester hydrochloride 36 (0.084 g, yield 100%) as a white solid.

MS m/z (ESI): 507.0 [M+1].

$^1$H NMR (400 MHz, CH$_3$OD): δ7.431-7.387 (m, 1H), 7.246-7.198 (m, 1H), 5.108-4.981 (m, 2H), 4.354-3.926 (m, 5H), 3.174-3.095 (m, 2H), 2.996-2.896 (m, 2H), 1.276 (s, 9H).

Example 37

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid 1-isopropoxycarbonyloxy-ethyl ester hydrochloride

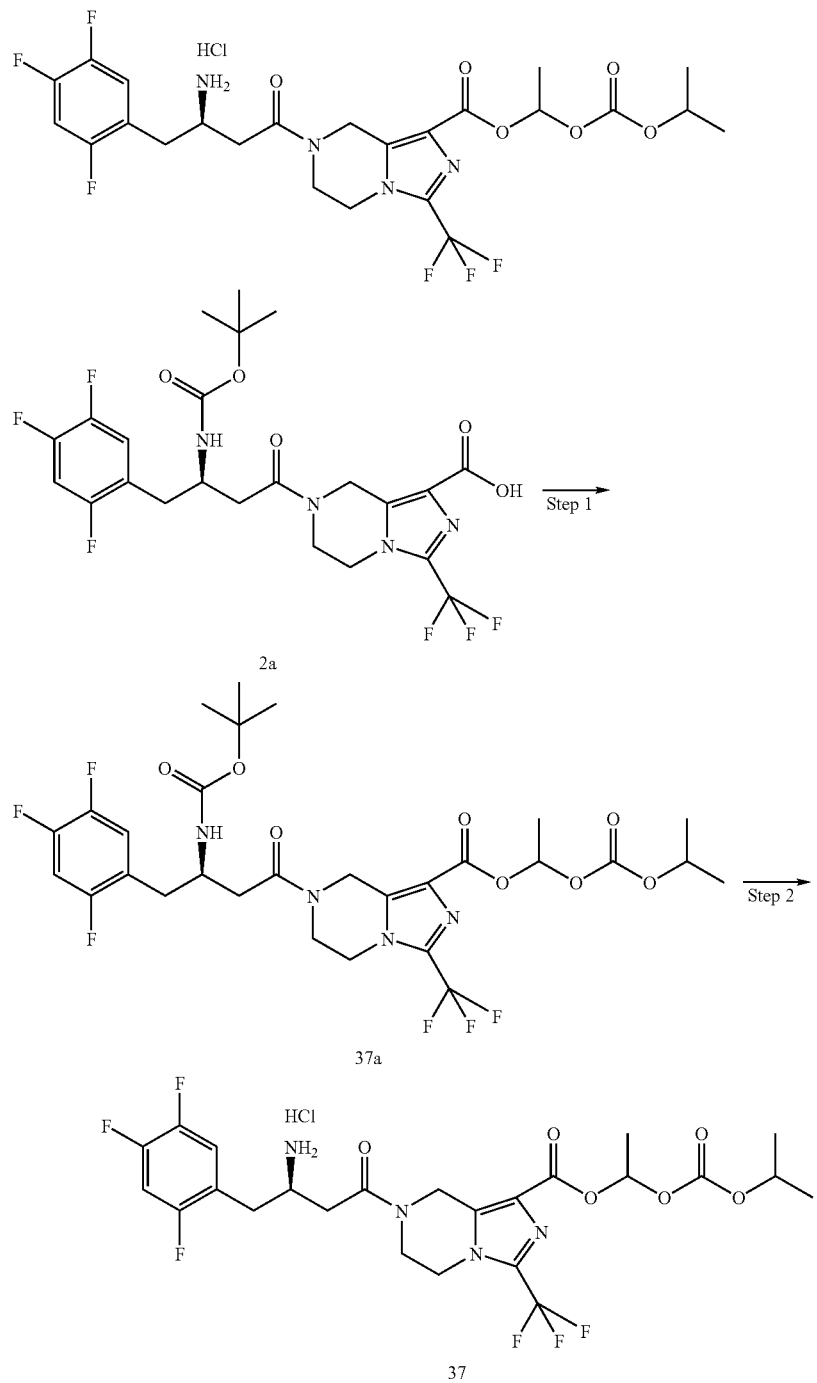

Step 1

(R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid isopropoxycarbonyloxy-ethyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (0.275 g, 0.5 mmol) and 4 mL of N,N-dimethylformamide were added into the reaction tube. After stirring until 2a was dissolved, 1-chloroethyl isopropyl carbonate (0.1 g, 0.6 mmol), potassium iodide (0.0415 g, 0.25 mmol) and potassium carbonate (0.083 g, 0.6 mmol) were then added to the solution successively. Upon completion of the addition, the reaction tube was sealed up. The reaction mixture was reacted at 65° C. for 2 hours in an oil bath and monitored by thin layer chromatography until the disappearance of the starting materials, and then the oil bath was removed. After cooling to room temperature, 40 mL of water was added to the reaction tube. The reaction mixture was extracted with ethyl acetate (25 mL×3). Thin layer chromatography showed there was no product in the aqueous phase, and the organic phase was collected, then washed with water (20 mL×2), then the combined organic phase was dried over anhydrous magnesium sulfate, filtered and concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 1-isopropoxycarbonyloxy-ethyl ester 37a (0.29 g, yield 85.3%) as a yellow solid.

MS m/z (ESI): 698.0 (M+18).

$^1$H NMR (400 MHz, CDCl$_3$): δ7.12 (m, 1H), 7.05 (m, 1H), 6.92 (m, 1H), 5.38 (d, 1H), 5.15 (d, 1H), 5.01 (s, 1H), 4.94 (m, 1H), 4.23-3.94 (m, 5H), 2.98 (m, 2H), 2.70 (m, 1H), 1.70 (d, 2H), 1.62 (s, 1H), 1.40 (s, 9H).

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid 1-isopropoxycarbonyloxy-ethyl ester hydrochloride (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 1-isopropoxycarbonyloxy-ethyl ester 37a (0.29 g, 0.43 mmol) and 5 mL of ethyl acetate were added into the reaction flask. A solution of 6.5 N hydrochloric acid in 3 mL of ethyl acetate was then added to the flask. The reaction mixture was stirred at room temperature for 4 hours and monitored by thin layer chromatography until the disappearance of the starting materials. The reaction mixture was concentrated under reduced pressure. The resulting residue was purified by silica gel column chromatography to obtain the title compound R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid 1-isopropoxycarbonyloxy-ethyl ester hydrochloride 37 (0.24 g, yield 91.2%) as a white solid.

MS m/z (ESI): 581.1 [M+1].

$^1$H NMR (400 MHz, CD$_3$OD): δ7.38 (m, 1H), 7.25 (m, 1H), 6.96 (m, 1H), 5.10 (m, 2H), 4.88 (m, 1H), 4.33 (m, 2H), 4.11 (m, 2H), 3.95 (m, 2H), 3.05 (m, 2H), 3.00 (m, 1H), 2.85 (m, 1H), 2.03 (m, 3H), 1.64 (m, 3H).

Example 38

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (1-cyclohexyloxy-carbonyloxy)-ethyl ester hydrochloride

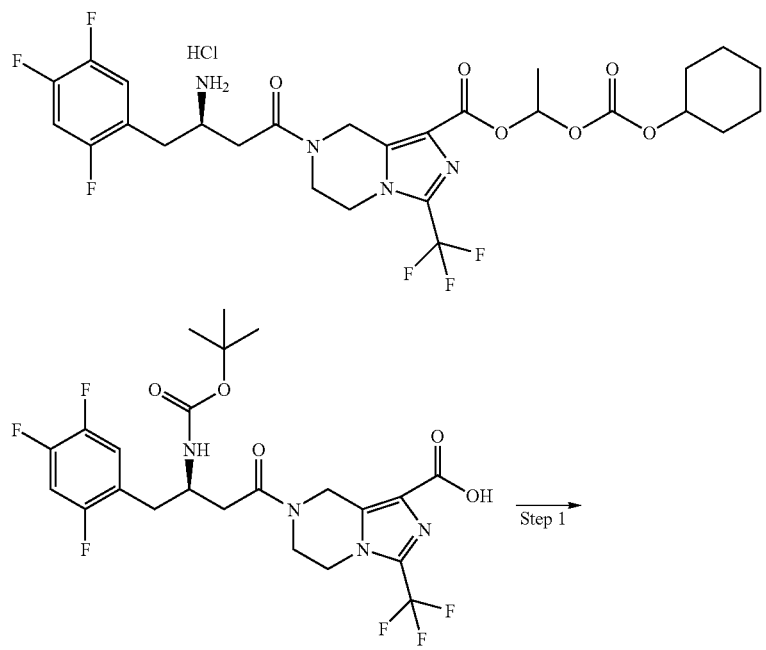

2a

-continued

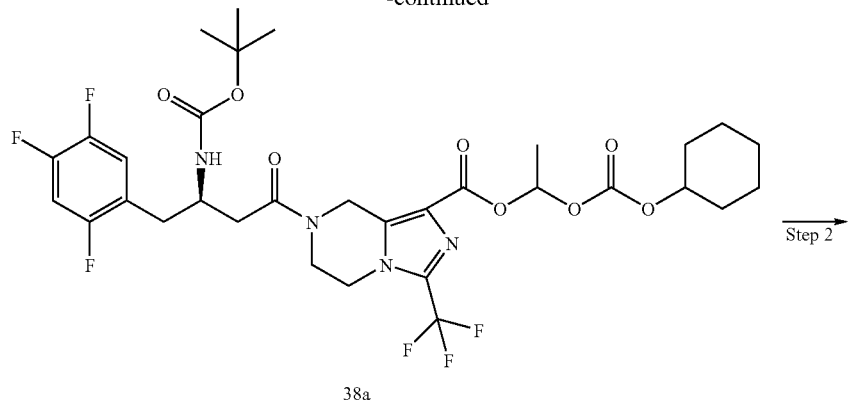

38a

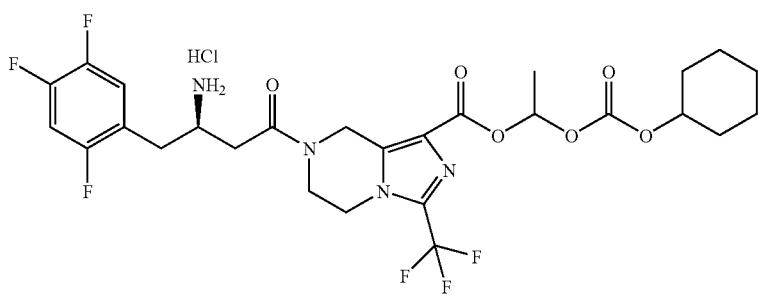

38

Step 1

(R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (1-cyclohexyloxycarbonyloxy)-ethyl ester (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid 2a (0.275 g, 0.5 mmol) and 4 mL of N,N-dimethylformamide were added to the reaction tube. After stirring until 2a was dissolved, 1-chloroethyl cyclohexyl carbonate (0.124 g, 0.6 mmol), potassium iodide (0.0415 g, 0.25 mmol) and potassium carbonate (0.083 g, 0.6 mmol) were then added to the solution successively. Upon completion of the addition, the reaction tube was sealed up. The reaction mixture was reacted at 65° C. in an oil bath for 2 hours and monitored by thin layer chromatography until the disappearance of the starting materials, and then the oil bath was removed. After cooling to room temperature, 40 mL of water was added to the reaction tube. The reaction mixture was extracted with ethyl acetate (30 mL×3). The combined organic phase was washed with 30 mL of water and 30 mL of saturated brine successively. The combined organic phase was dried over anhydrous magnesium sulfate, filtered and concentrated under reduced pressure. The resulting residue was purified by silica gel column chromatography to obtain the title compound (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid (1-cyclohexyloxycarbonyloxy)-ethyl ester 38a (0.25 g, yield 69.4%) as a white solid.

MS m/z (ESI): 721.0 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid (1-cyclohexyloxycarbonyloxy)-ethyl ester hydrochloride (R)-7-[3-tert-Butoxycarbonylamino-4-(2,4,5-trifluorophenyl)-butyryl]-3-trifluoromethyl-5,6,7,8-tetrahydro-imidazo[1,5-a]pyrazine-1-carboxylic acid (1-cyclohexyloxycarbonyloxy)-ethyl ester 38a (0.25 g, 0.347 mmol) and 5 mL of ethyl acetate were added into the reaction flask. A solution of 6.5 N hydrochloric acid in 3 mL of ethyl acetate was added to the flask under stirring. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluorophenyl)-butyryl]-3-trifluoromethyl-5,6,7,8-tetrahydro-imidazo[1,5-a]pyrazine-1-carboxylic acid (1-cyclohexyloxycarbonyloxy)-ethyl ester hydrochloride 38 (0.22 g, yield 96.1%) as a white solid.

MS m/z (ESI): 621.1 [M+1].

$^1$H NMR (400 MHz, CD$_3$OD): δ7.30 (m, 1H), 7.16 (m, 1H), 6.95 (m, 1H), 5.10 (m, 1H), 4.64 (m, 1H), 4.29 (d, 2H), 4.02 (d, 2H), 3.61 (s, 1H), 2.87 (d, 2H), 2.70 (s, 1H), 2.65 (m, 1H), 1.93 (s, 3H), 1.74 (s, 2H), 1.64 (m, 3H), 1.47 (m, 3H), 1.31 (m, 3H).

Example 39

(R)-7-[3-Amino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester hydrochloride

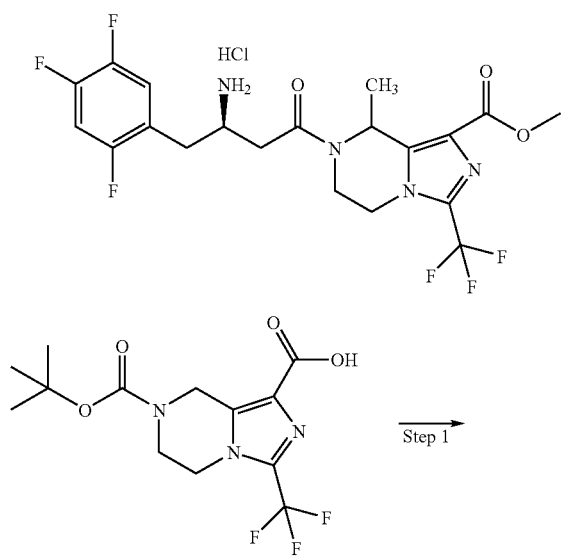

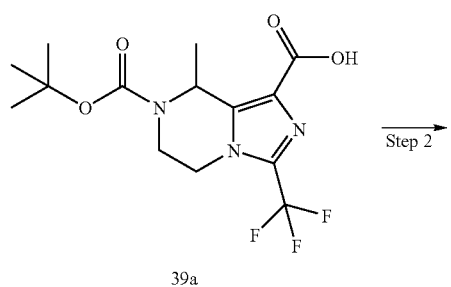

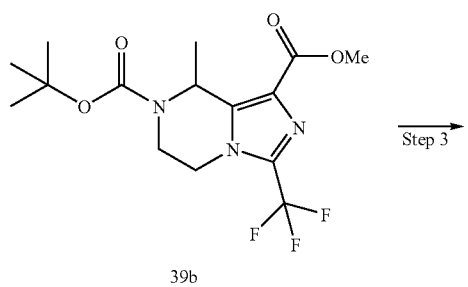

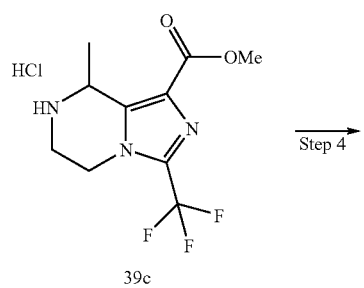

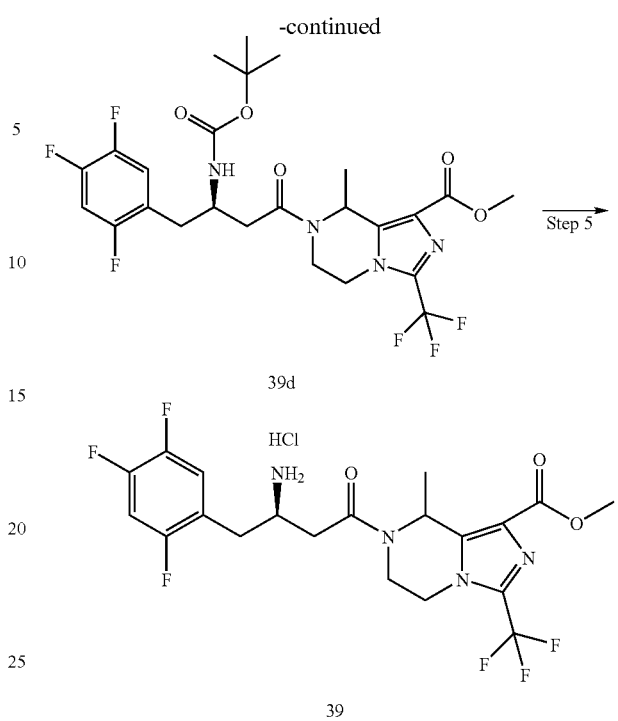

Step 1

8-Methyl-3-trifluoromethyl-5,6-dihydro-8H-imidazo[1,5-a]pyrazine-1,7-dicarboxylic acid 7-tert-butyl ester 3-Trifluoromethyl-5,6-dihydro-8H-imidazo[1,5-a]pyrazine-1,7-dicarboxylic acid 7-tert-butyl ester 27d (0.85 g, 2.54 mmol) was dissolved in a mixture of 25 mL of anhydrous toluene and 8 mL of anhydrous tetrahydrofuran. The reaction flask was placed in a dry ice-acetone bath and cooled to −78° C., and then tetramethyl-ethylenediamine (1.32 mL, 8087 mmol) was added to the flask. n-Butyllithium (5.55 mL, 8.87 mmol) was added dropwise in 5 minutes. After reacting at −78° C. for 15 minutes, iodomethane (0.4 mL, 6.34 mmol) was added dropwise. The reaction mixture was reacted at −78° C. for 10 minutes, then was allowed to warm up to room temperature and reacted for 2 hours until thin lay chromatography showed the starting material disappeared. 15 mL of saturated ammonium chloride and 20 mL of water were added to the reaction mixture successively. The mixture was adjusted to pH 3-4 with 2 N hydrochloric acid, and extracted with ethyl acetate (30 mL×3). The combined organic phase was dried over anhydrous sodium sulfate, filtered and concentrated under reduced pressure. The resulting residue was purified by silica gel column chromatography to obtain the title compound 8-methyl-3-trifluoromethyl-5,6-dihydro-8H-imidazo[1,5-a]pyrazine-1,7-dicarboxylic acid 7-tert-butyl ester 39a (0.215 g, yield 24.3%) as a white solid.

Step 2

8-Methyl-3-trifluoromethyl-5,6-dihydro-8H-imidazo[1,5-a]pyrazine-1,7-dicarboxylic acid 7-tert-butyl ester 1-methyl ester 8-Methyl-3-trifluoromethyl-5,6-dihydro-8H-imidazo[1,5-a]pyrazine-1,7-dicarboxylic acid 7-tert-butyl ester 39a (0.349 g, 1 mmol) was dissolved in 15 mL of N,N-dimethylformamide, and sodium bicarbonate (0.84 g, 10 mmol) was added to the solution under stirring. Iodomethane (0.43 g, 3 mmol) was added dropwise. The reaction mixture was stirred at room temperature for 40 hours and monitored by thin layer chromatography until the disappearance of the starting materials. The reaction mixture was concentrated under reduced pressure. The resulting residue was purified by silica gel column chromatography to obtain the title compound 8-methyl-3-trifluoromethyl-5,6-dihydro-8H-imidazo[1,5-a]pyrazine-1,7-dicarboxylic acid 7-tert-butyl ester 1-methyl ester 39b (0.5 g, yield 100%) as a yellow oil.

MS m/z (ESI): 364.0 [M+1].

$^1$H NMR (400 MHz, CDCl$_3$): δ 5.85 (t, 1H), 4.24 (t, 2H), 4.04 (t, 2H), 3.93 (s, 3H), 1.56 (d, 3H), 1.51 (s, 9H).

Step 3

8-Methyl-3-trifluoromethyl-5,6,7,8-tetrahydro-imidazo[1,5-a]pyrazine-1-carboxylic acid methyl ester hydrochloride 8-Methyl-3-trifluoromethyl-5,6-dihydro-8H-imidazo[1,5-a]pyrazine-1,7-dicarboxylic acid 7-tert-butyl ester 1-methyl ester 39b (0.35 g, 0.96 mmol) was added into the reaction flask. A solution of 2.3 N hydrochloric acid in 10 mL of ethyl acetate was then added to the flask. The reaction mixture was stirred at room temperature for 2 hours and monitored by thin layer chromatography until the disappearance of the starting materials. The reaction mixture was concentrated under reduced pressure to obtain the title compound 8-methyl-3-trifluoromethyl-5,6,7,8-tetrahydro-imidazo[1,5-a]pyrazine-1-carboxylic acid methyl ester hydrochloride 39c crude product (0.4 g) as a yellow oil.

$^1$H NMR (400 MHz, CDCl$_3$): δ 7.10 (m, 1H), 6.91 (m, 1H), 5.57 (m, 1H), 5.45 (m, 2H), 4.18 (m, 2H), 3.97 (s, 3H), 3.36 (t, 1H), 2.98 (m, 2H), 2.26 (m, 2H), 1.60 (d, 3H), 1.40 (s, 9H).

Step 4

(R)-7-[3-tert-Butoxycarbonylamino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester 8-Methyl-3-trifluoromethyl-5,6,7,8-tetrahydro-imidazo[1,5-a]pyrazine-1-carboxylic acid methyl ester hydrochloride 39c crude product (0.289 g, 0.96 mmol) and (R)-3-tert-butoxycarbonylamino-4-(2,4,5-trifluoro-phenyl)-butyric acid 1f (0.353 g, 1.06 mmol) were dissolved in 10 mL of dichloromethane, followed by addition of triethylamine (0.4 mL, 2.9 mmol) and bis(2-oxo-3-oxazolidinyl)phosphinic chloride (0.368 g, 1.45 mmol) under stirring. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-7-[3-tert-butoxycarbonylamino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester 39d (0.43 g, yield 77.2%) as a yellow oil.

MS m/z (ESI): 579.1 [M+1].

Step 5

(R)-7-[3-Amino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester hydrochloride (R)-7-[3-tert-Butoxycarbonylamino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester 39d (0.23 g, 0.4 mmol) was added into the reaction flask. A solution of 2.3 N hydrochloric acid in 5 mL of ethyl acetate was then added to the flask. The reaction mixture was stirred at room temperature for 2 hours and monitored by thin layer chromatography until the disappearance of the starting materials. The reaction mixture was concentrated under reduced pressure to obtain the title compound (R)-7-[3-amino-4-(2,4,5-trifluoro-phenyl)-butyryl]-8-methyl-3-trifluoromethyl-5,6,7,8-tetrahydro-imidazo[1,5-a]pyrazine-1-carboxylic acid methyl ester hydrochloride 39 (0.205 g, yield 100%) as a white solid.

MS m/z (ESI): 479.1 [M+1].

$^1$H NMR (400 MHz, CDCl$_3$): δ 7.33 (m, 1H), 6.93 (m, 1H), 5.58 (m, 1H), 5.02 (m, 1H), 4.33 (m, 2H), 3.86 (s, 3H), 3.43 (t, 2H), 3.06 (m, 2H), 2.49 (m, 2H), 1.57 (d, 3H).

Example 40, 41

(R)-7-[3-Amino-4-(2,4,5-trifluoro-phenyl)-butyryl]-(S)-8-methyl-3-trifluoromethyl-5,6,7,8-tetrahydro-imidazo[1,5-a]pyrazine-1-carboxylic acid methyl ester hydrochloride (R)-7-[3-Amino-4-(2,4,5-trifluoro-phenyl)-butyryl]-(R)-8-methyl-3-trifluoromethyl-5,6,7,8-tetrahydro-imidazo[1,5-a]pyrazine-1-carboxylic acid methyl ester hydrochloride

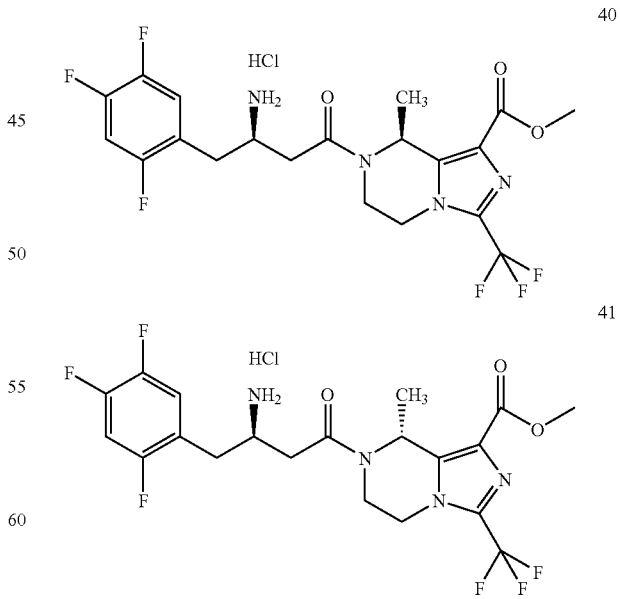

Chiral resolution of (R)-7-[3-amino-4-(2,4,5-trifluoro-phenyl)-butyryl]-8-methyl 3-trifluoromethyl-5,6,7,8-tetrahydro-imidazo[1,5-a]pyrazine-1-carboxylic acid methyl ester hydrochloride 39 (141 mg, 29.5 mmol) was performed by high performance liquid chromatography (HPLC). The enantiomers were separated by chiral column (separation condition: chiral column Chiralcel AD-H, mobile phase: n-hexane: isopropanol: diethylamine=70:30:0.1, flow rate: 1.0 mL/min). The corresponding compositions were collected, and the solvent was removed by rotary evaporator. The resulting residue was dried under vacuum at room temperature for 4 hours to obtain the title compound (R)-7-[3-amino-4-(2,4,5-trifluoro-phenyl)-butyryl]-(S)-8-methyl-3-trifluoromethyl-5,6,7,8-tetrahydro-imidazo[1,5-a]pyrazine-1-carboxylic acid methyl ester hydrochloride 40 (57 mg, 11.9 mmol) and (R)-7-[3-amino-4-(2,4,5-trifluoro-phenyl)-butyryl]-(R)-8-methyl-3-trifluoromethyl-5,6,7,8-tetrahydro-imidazo[1,5-a]pyrazine-1-carboxylic acid methyl ester hydrochloride 41 (50 mg, 10.5 mmol).

Example 42

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid ethylamide

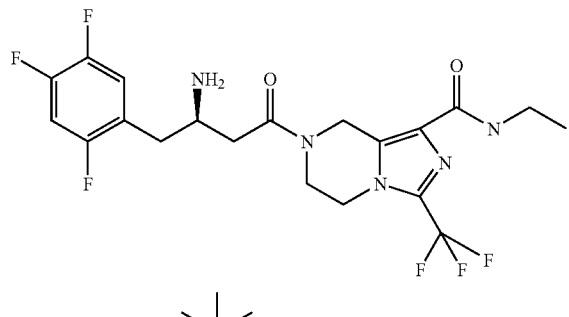

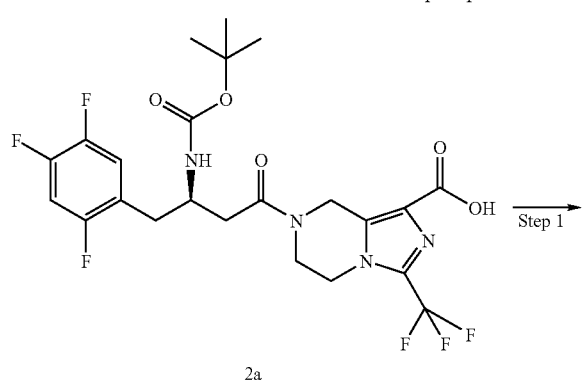
2a

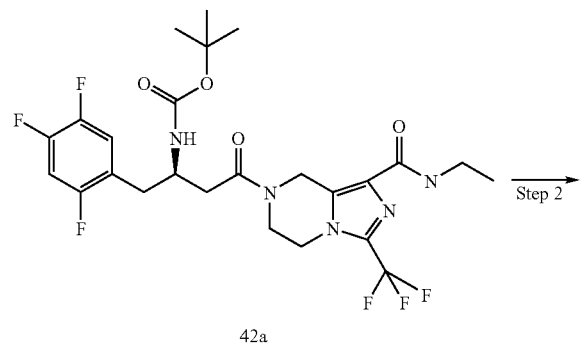
42a

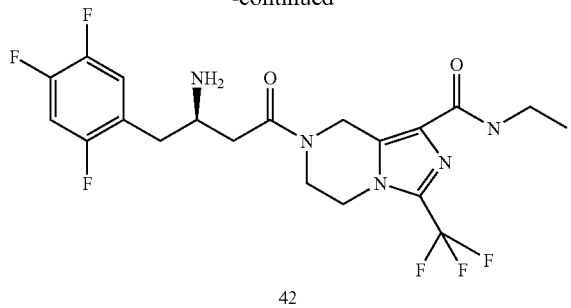
42

Step 1

(R)-[3-(1-Ethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (180 mg, 0.33 mmol) was dissolved in 10 mL of tetrahydrofuran, and ethylamine hydrochloride (269 mg, 3.3 mmol), bis(2-oxo-3-oxazolidinyl)phosphinic chloride (168 mg, 0.66 mmol) and triethylamine (367 mg, 3.63 mmol) were then added to the solution. The reaction mixture was stirred at room temperature for 4 hours until thin lay chromatography showed the starting material disappeared, and then filtered and concentrated under reduced pressure. The resulting residue was purified by silica gel column chromatography to obtain the title compound (R)-[3-(1-ethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 42a (190 mg, yield>100%) as a white solid.

MS m/z (ESI): 600.1 [M+23].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid ethylamide (R)-[3-(1-Ethylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 42a (190 mg, 0.33 mmol) was dissolved in 10 mL of dichloromethane, and trifluoroacetic acid (750 mg, 6.6 mmol) was added to the solution. The reaction mixture was stirred at room temperature for 2 hours and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid ethylamide 42 (120 mg, yield 76.4%) as a white solid.

MS m/z (ESI): 478.1 [M+1].

$^1$H NMR (400 MHz, CD$_3$OD): δ 1.68-1.24 (m, 3H), 2.79-3.01 (m, 2H), 3.10 (s, 2H), 3.33-3.41 (m, 2H), 4.24-4.30 (d, 2H), 5.03-5.18 (m, 2H), 7.14-7.23 (m, 1H), 7.36-7.37 (d, 1H).

Example 43

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid butylamide

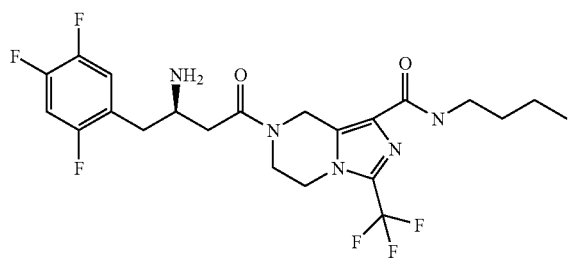

2a

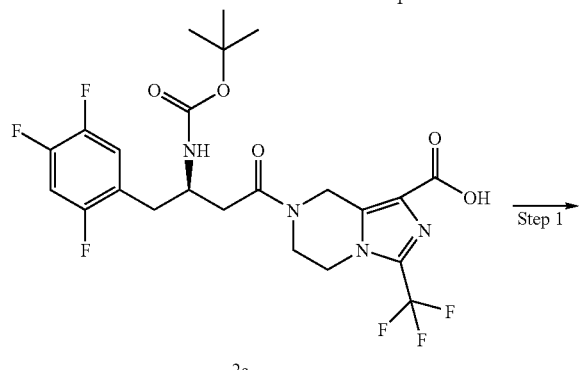

43a

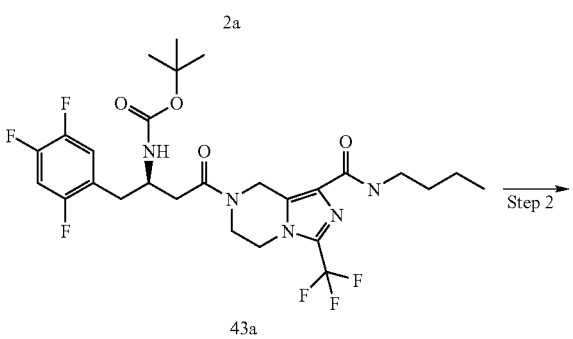

43

Step 1

(R)-[3-(1-Butylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (180 mg, 0.33 mmol) was dissolved in 10 mL of dichloromethane, followed by addition of butylamine hydrochloride (193 mg, 2.64 mmol), bis(2-oxo-3-oxazolidinyl)phosphinic chloride (167 mg, 0.66 mmol) and triethylamine (100 mg, 0.99 mmol). The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-[3-(1-butylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 43a (120 mg, yield 60%) as a white solid.

MS m/z (ESI): 606.0 [M+1].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid butylamide (R)-[3-(1-Butylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 43a (120 mg, 0.198 mmol) was dissolved in 10 mL of dichloromethane, and trifluoroacetic acid (452 mg, 3.97 mmol) was then added to the solution. The reaction mixture was stirred at room temperature for 2 hours and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid butylamide 43 (70 mg, yield 70%) as a white solid.

MS m/z (ESI): 506.1 [M+1].

$^1$H NMR (400 MHz, CD$_3$OD): δ 0.93-0.99 (m, 3H), 1.34-1.41 (m, 2H), 1.59-1.62 (m, 2H), 2.80-2.98 (m, 3H), 3.07-3.15 (m, 2H), 3.37 (m, 1H), 3.90-3.91 (d, 2H), 4.06-4.07 (m, 1H), 4.27-4.34 (m, 2H), 5.03-5.15 (m, 2H), 7.20-7.37 (m, 2H).

Example 44

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid propylamide

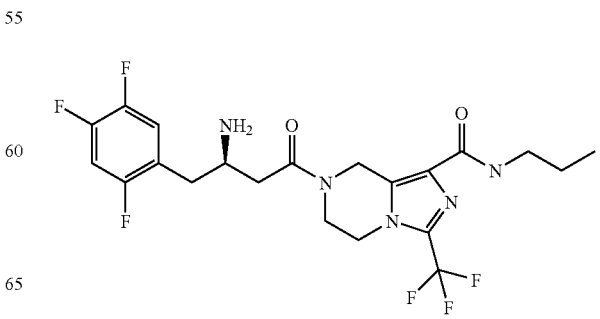

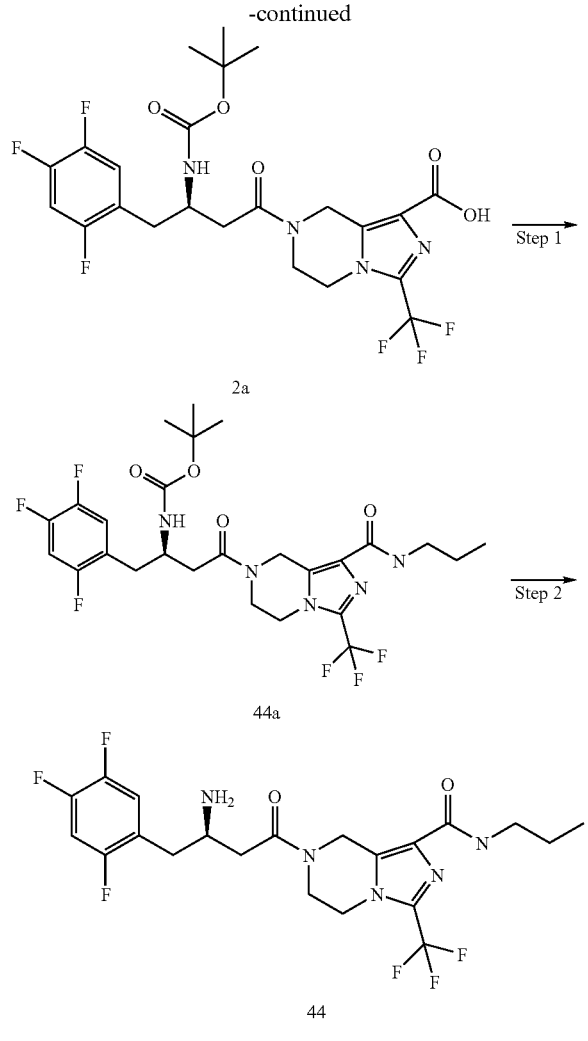

Step 1

(R)-[3-(1-Propylcarbamoyl-3-trifluoromethyl-5,6-dihydro-5H-imidazo[1,5-a]pyrazin-7-yl)-3-oxo-1-(2,4,5-trifluoro-benzyl)-propyl]carbamic acid tert-butyl ester (R)-7-[3-tert-Butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid 2a (190 mg, 0.345 mmol) was dissolved in 10 mL of dichloromethane, and propylamine (163 mg, 2.76 mmol), bis(2-oxo-3-oxazolidinyl) phosphinic chloride (176 mg, 0.69 mmol) and triethylamine (105 mg, 1.04 mmol) were then added to the solution. The reaction mixture was stirred at room temperature overnight and monitored by thin layer chromatography until the disappearance of the starting materials. The reaction mixture was concentrated under reduced pressure. The resulting residue was purified by silica gel column chromatography to obtain the title compound (R)-[3-(1-propyl-carbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 44a (70 mg, yield 34.3%) as a white solid.

MS m/z (ESI): 614.1 [M+23].

Step 2

(R)-7-[3-Amino-4-(2,4,5-trifluoro-phenyl)-butyryl]-3-trifluoromethyl-5,6,7,8-tetrahydro-imidazo[1,5-a]pyrazine-1-carboxylic acid propylamide (R)-[3-(1-Propylcarbamoyl-3-trifluoromethyl-5,6-dihydro-8H-imidazo[1,5-a]pyrazin-7-yl)-3-oxo-1-(2,4,5-trifluoro-benzyl)-propyl]-carbamic acid tert-butyl ester 44a (70 mg, 0.118 mmol) was dissolved in 10 mL of dichloromethane, and trifluoroacetic acid (270 mg, 2.37 mmol) was then added to the solution. The reaction mixture was stirred at room temperature for 1 hour and monitored by thin layer chromatography until the disappearance of the starting materials. The reaction mixture was concentrated under reduced pressure. The resulting residue was purified by silica gel column chromatography to obtain the title compound (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid propylamide 44 (25 mg, yield 43.1%) as a white solid.

MS m/z (ESI): 492.1 [M+1].

$^1$H NMR (400 MHz, CD$_3$OD): δ 0.90-1.00 (m, 3H), 1.60-1.66 (m, 2H), 2.75-2.84 (m, 1H), 2.93-2.99 (m, 1H), 3.09 (s, 2H), 3.94-3.95 (d, 2H), 4.07 (m, 1H), 4.24-4.29 (m, 2H), 5.03-5.13 (m, 2H), 7.19-7.23 (t, 1H), 7.36-7.38 (d, 1H).

TEST EXAMPLES

Pharmacological Assays

Assays for Determining DPP-IV Inhibitory Activity

The compounds of the present invention were tested to determine the DPP-IV inhibitory activity according to the following methods. Inhibitory rates or the half maximal inhibitory concentrations IC$_{50}$ (the concentration of the test compound showing 50% inhibition of the enzyme activity) of each compound were determined by incubating fixed amounts of enzyme mixed substrate with several different concentrations of the test compounds.

Assays for Determining DPP-IV Inhibitory Activity

Materials and Methods:

Materials:
a. 96-well white plate (BMG);
b. Tris buffer: in order to prepare 100 mL 2 mM Tris Buffer, 0.0242 g Tris was dissolved in about 90 mL of distilled H$_2$O firstly. Hydrochloric acid and sodium hydroxide were used to adjust the pH value to 8.00 and the solution was then diluted with dH$_2$O to 100 mL in total volume;
c. DPP-IV enzyme (CalBiochem Catalog No. 317630), dissolved in Tris buffer to 2 mM;
d. DPP-IV-Glo™ Substrate (Promega Catalog No. G8350), dissolved in dH$_2$O to 1 mM;
e. DPP-IV-Glo™ Buffer (Promega Catalog No. G8350);
f. Luciferin Detection Reagent (Promega Catalog No. G8350);
g. DMSO;
h. dH$_2$O Procedure:
The assay was carried out in the order of the following steps:
1. DPP-IV-Glo. was thawed and equilibrated to room temperature before it was used.
2. The freezing luciferin detection reagent was equilibrated to room temperature before it was used.

3. DPP-IV-Glo. was mixed with ultrapure water by mixing briefly to form 1 mM substrate.
4. The luciferin detection reagent was placed in a brown flask with addition of DPP-IV-Glo., wherein the luciferin detection reagent should be dissolved in less than one minute.
5. The test compounds were dissolved in DMSO to 50 fold of the final concentration.
6. 2 µL of the test compound with a 50 fold concentration was added to each tube, and 2 µL of DMSO was added to negative control and blank control.
7. 46 µL of Tris buffer was added to each tube and 48 µL of Tris buffer was added in blank control.
8. 2 µL of DPP-IV enzyme was added to each negative control tube and test tube.
9. The test tubes were shaked and centrifuged, and then the substances of the test tube were transferred to 96-well plates.
10. The substrate and DPP-IV-Glo. were mixed in a ratio of 1:49, and the mixture was shaked throughfully and incubated at room temperature for 30-60 minutes before it was used.
11. The 96-well plate was sealed by sealing film after 50 µL of the mixed solution of DPP-IV-Glo. and substrate were added to each well.
12. The substances of the 96 wells were mixing slowly by using a plate shaker at 300-500 rpm/30 s, and then the plate was incubated at room temperature from 30 minutes to 3 hours.
13. The luminescence value was measured.

[1−(S−B)/(N−B)]*100%    The definition of inhibitory rate

S: sample
B: blank control
N: negative control
$IC_{50}$ Value:

| Example No. | $IC_{50}$ (µM) |
|---|---|
| MK-0431 | 0.023 |
| 1 | 0.012 |
| 2 | 0.008 |
| 3 | 0.089 |
| 4 | 0.022 |
| 5 | 0.027 |
| 6 | 0.031 |
| 7 | 0.025 |
| 8 | 0.008 |
| 9 | 0.075 |
| 10 | 0.021 |
| 11 | 0.216 |
| 12 | 0.059 |
| 13 | 0.041 |
| 14 | 0.047 |
| 15 | 0.025 |
| 23 | 0.031 |
| 34 | 0.031 |
| 36 | 0.221 |
| 37 | 0.033 |
| 38 | 0.184 |
| 39 | 0.016 |
| 40 | 0.314 |
| 41 | 0.005 |
| 42 | 0.018 |
| 43 | 0.063 |
| 44 | 0.052 |

After testing, the half maximal inhibitory concentration $IC_{50}$ value of the compounds of the present invention against DPP-IV ranged from 0.005 µM to 0.216 µM. Compared with $IC_{50}$ value of MK-0431 (0.023 µM), a majority of compounds of the present invention exhibited excellent inhibitory activity against DPP-IV.

What is claimed is:
1. A compound of formula (II):

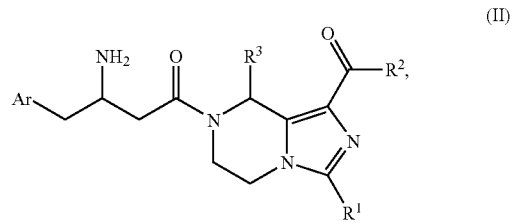

or a pharmaceutically acceptable salt thereof, wherein:
Ar is phenyl, either unsubstituted or substituted with 1 to 5 substituents independently selected from the group consisting of halogen, cyano, hydroxyl, alkyl or alkoxyl, wherein the alkyl or alkoxyl is each independently unsubstituted or substituted with one or more halogens;
$R^1$ is selected from the group consisting of hydrogen, alkyl, trifluoromethyl, cycloalkyl, aryl and heteroaryl, wherein the alkyl, cycloalkyl, aryl or heteroaryl is each independently either unsubstituted or substituted with one or more groups independently selected from the group consisting of halogen, cyano, aryl, hydroxyl and amino;
$R^2$ is selected from the group consisting of hydroxyl, amino, alkyl, alkoxyl, cycloalkyl, heterocyclic alkyl, aryl, heteroaryl and —$NR^4R^5$, wherein the alkyl, alkoxyl, cycloalkyl, heterocyclic alkyl, aryl or heteroaryl is each independently either unsubstituted or substituted with one or more groups independently selected from the group consisting of halogen, amino, cyano, hydroxyl, alkyl, cycloalkyl, alkoxyl, aryl, heteroaryl, —$NR^4R^5$, —$OC(O)OR^8$, carboxylic acid and carboxylic ester;
$R^3$ is selected from the group consisting of hydrogen and alkyl;
$R^4$ and $R^5$ are each independently selected from the group consisting of hydrogen, alkyl, cycloalkyl, heterocyclic alkyl, aryl and heteroaryl, wherein the alkyl, cycloalkyl, heterocyclic alkyl, aryl or heteroaryl is each independently either unsubstituted or substituted with one or more groups independently selected from the group consisting of halogen, hydroxyl, amino, alkoxyl, alkyl, cyano, aryl, cycloalkyl, heterocyclic alkyl, heterocyclic aryl, hydroxyalkyl, —$SO_2R^7$, —$NR^4R^5$, carboxylic acid and carboxylic ester; or
$R^4$ and $R^5$, together with the nitrogen to which they are attached, form a 4 to 8 membered heterocycle, wherein the 4 to 8 membered heterocycle contains one or more N, O, S atoms, and the 4 to 8 membered heterocycle is either unsubstituted or substituted with one or more groups independently selected from the group consisting of halogen, hydroxyl, amino, alkoxyl, alkyl, cyano, aryl, heterocyclic alkyl, heteroaryl, carbonyl, hydroxyalkyl, —$SO_2R^7$, —$NR^4R^5$, —$C(O)NR^4R^5$, —$C(O)R^7$, =O, carboxylic acid and carboxylic ester;
$R^7$ is alkyl; and
$R^8$ is selected from the group consisting of alkyl and cycloalkyl.
2. The compound, or a pharmaceutically acceptable salt thereof, of claim 1, which is of formula (I):

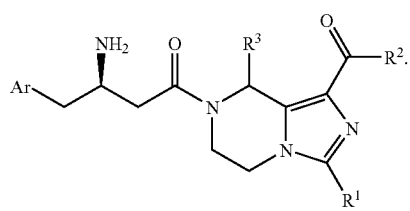

(I)

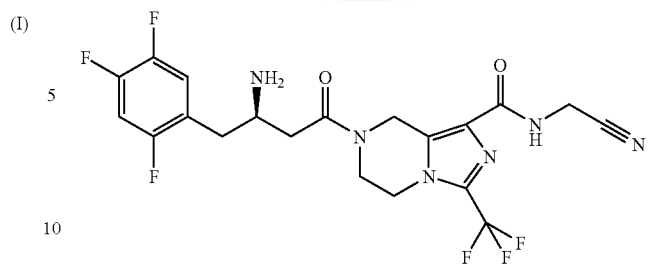

3. The compound, or a pharmaceutically acceptable salt thereof, of claim 1, wherein Ar is halogen-substituted phenyl.

4. The compound, or a pharmaceutically acceptable salt thereof, of claim 3, wherein Ar is trifluoro-phenyl.

5. The compound, or a pharmaceutically acceptable salt thereof, of claim 1, wherein $R^1$ is halogen-substituted alkyl.

6. The compound, or a pharmaceutically acceptable salt thereof, of claim 1, wherein $R^1$ is trifluoromethyl.

7. The compound, or a pharmaceutically acceptable salt thereof, of claim 1, wherein $R^2$ is selected from the group consisting of —OH, —OCH$_3$, —NHCH$_3$, —NHCH$_2$CH$_3$, —NHCH$_2$CN, and —NHCH$_2$CH$_2$SO$_2$CH$_3$.

8. The compound, or a pharmaceutically acceptable salt thereof, of claim 1, wherein $R^3$ is hydrogen or methyl.

9. The compound, or a pharmaceutically acceptable salt thereof, of claim 1, which is selected from the group consisting of:

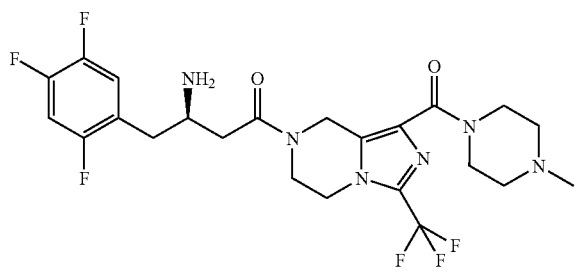

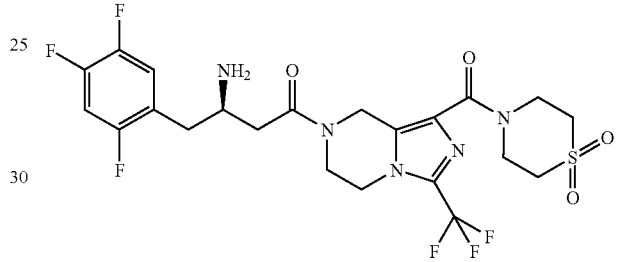

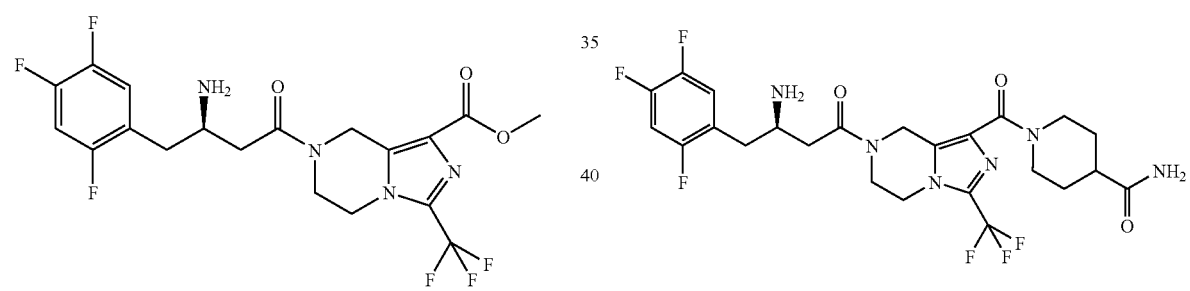

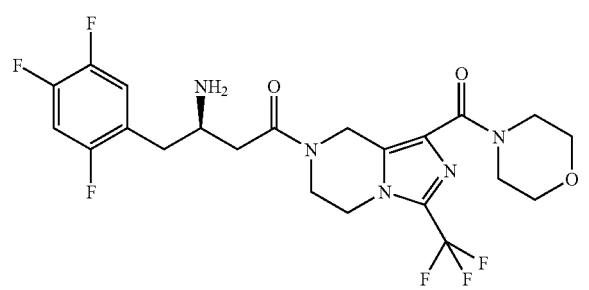

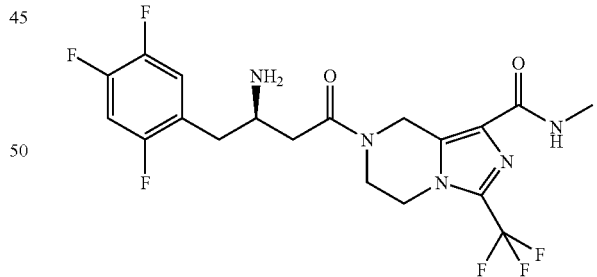

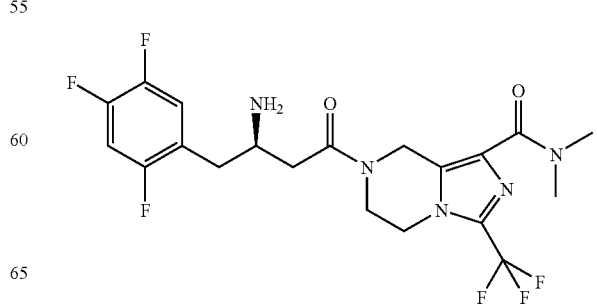

135
-continued
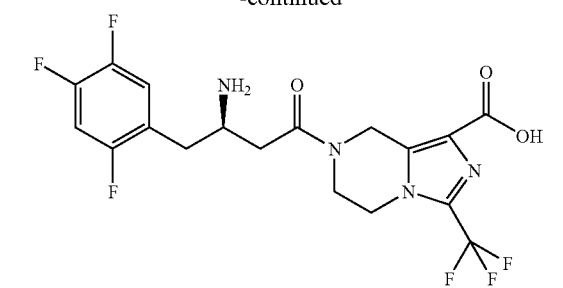
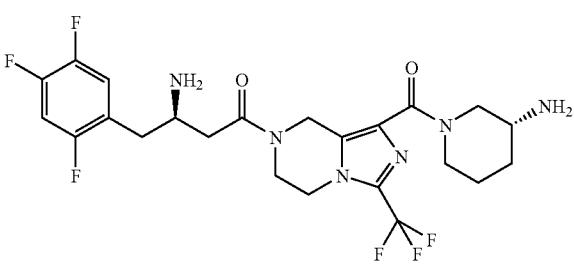
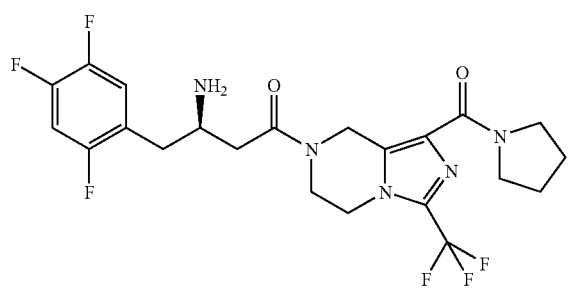
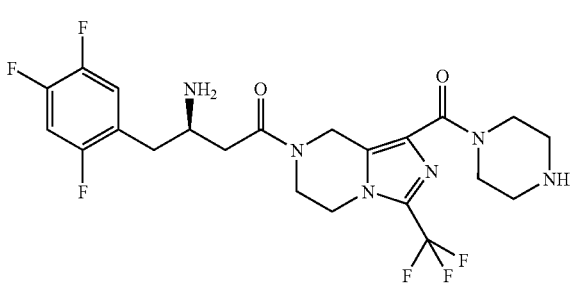
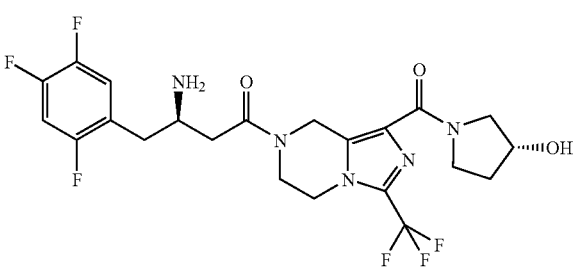
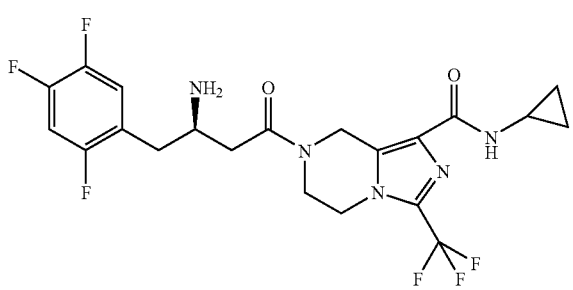
136
-continued
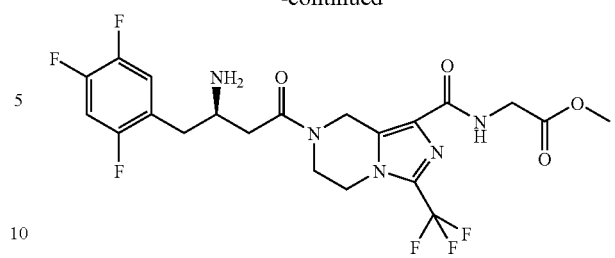
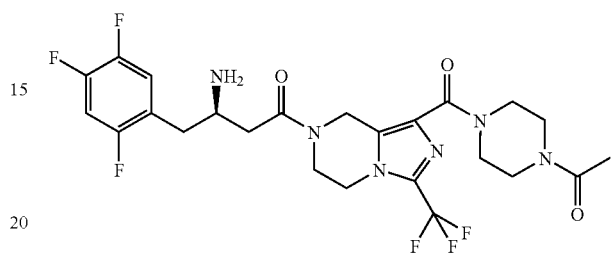
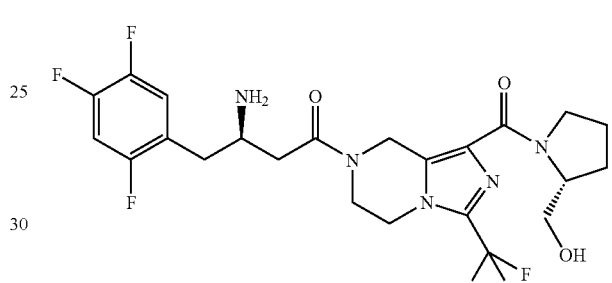
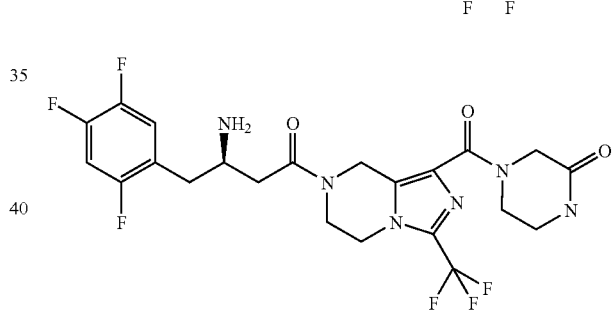
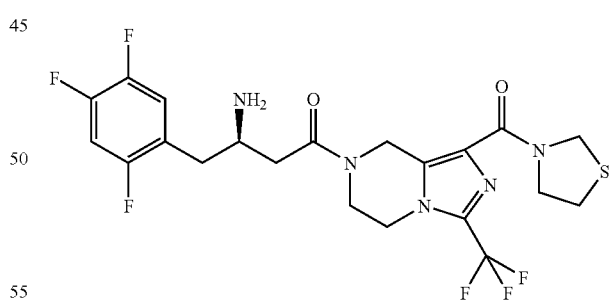
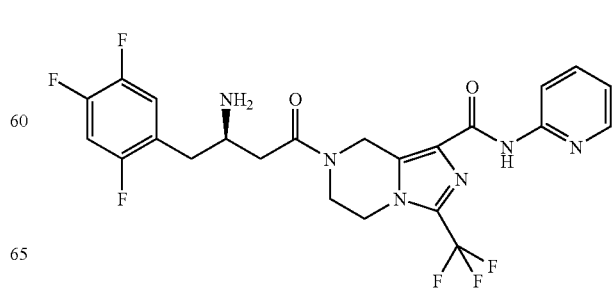

137
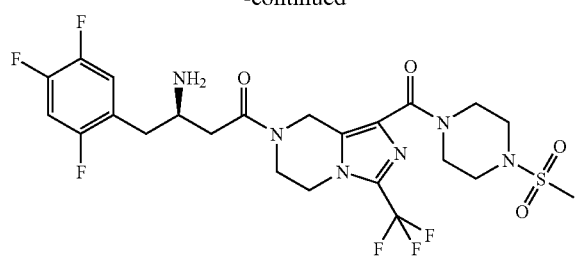
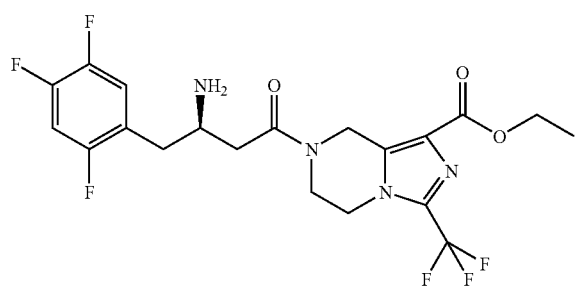
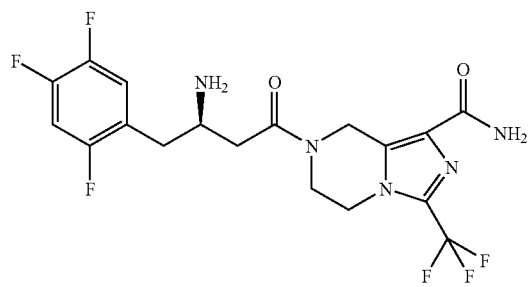
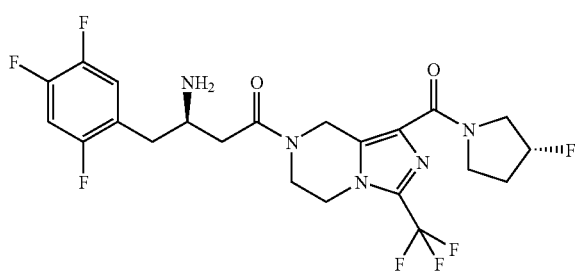
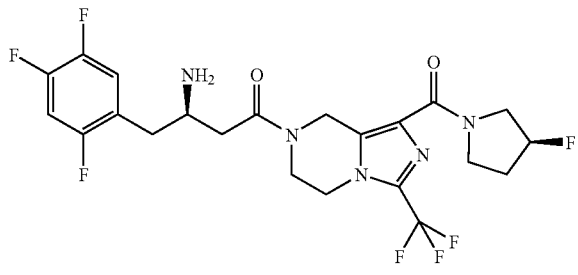
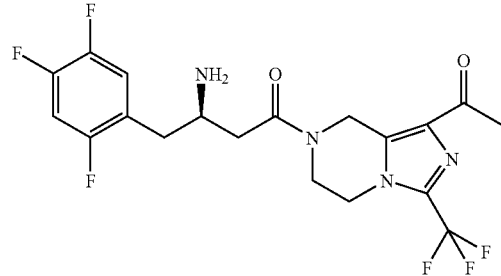
138
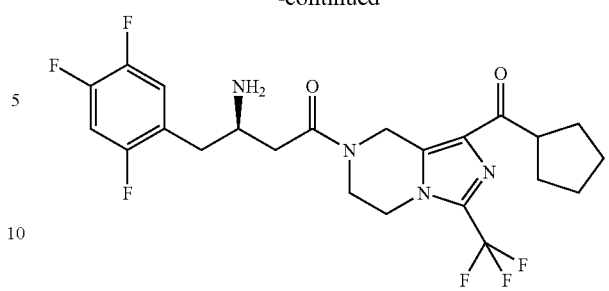
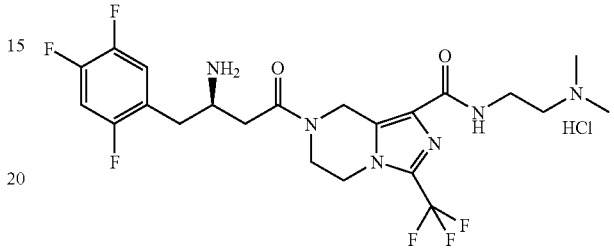
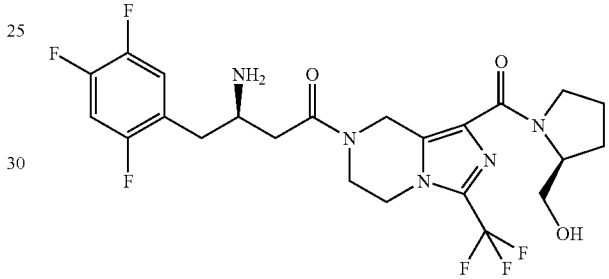
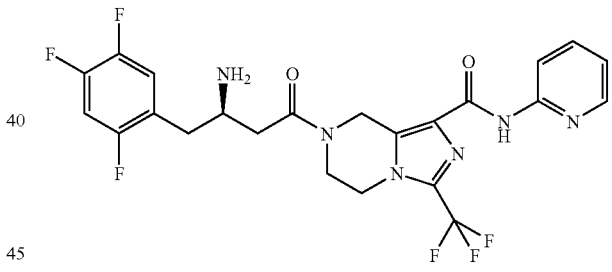
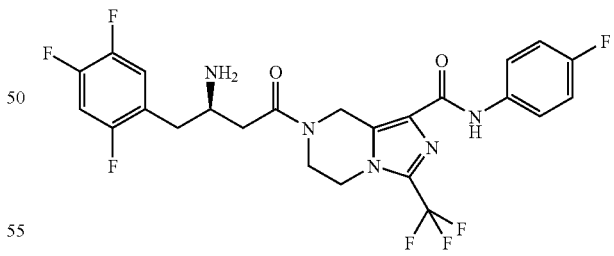
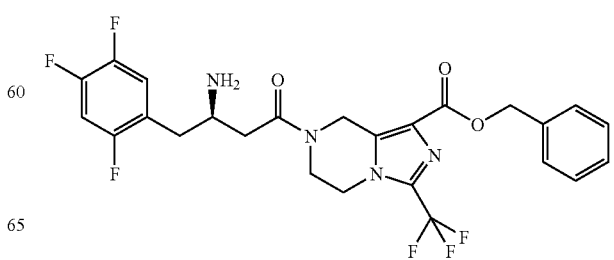

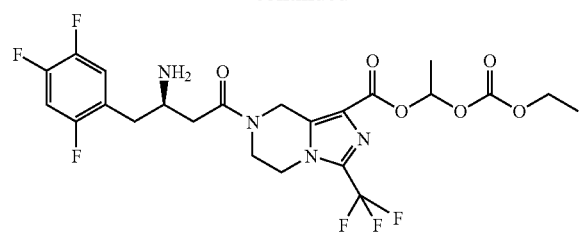
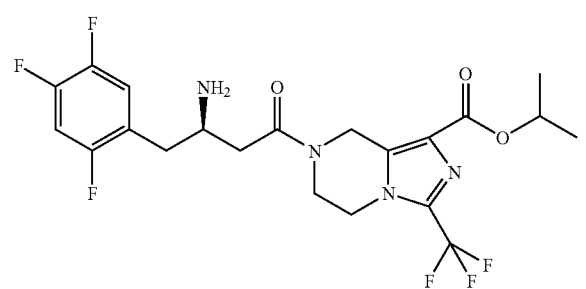
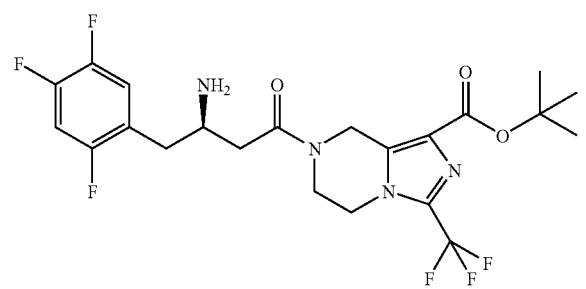
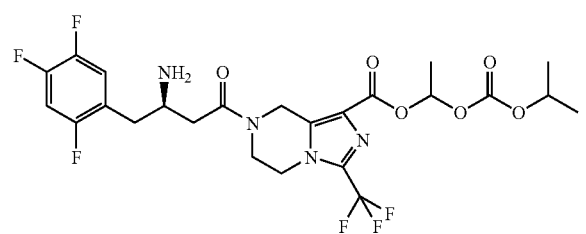
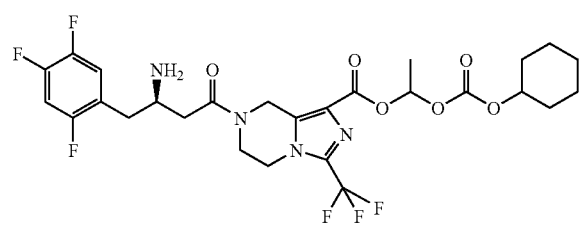
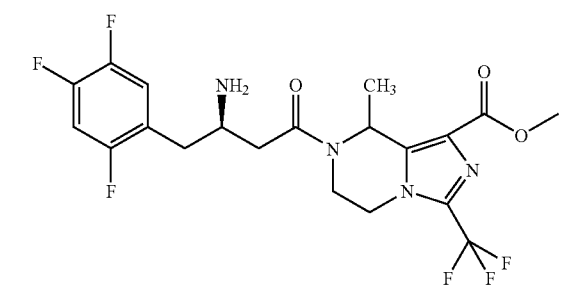
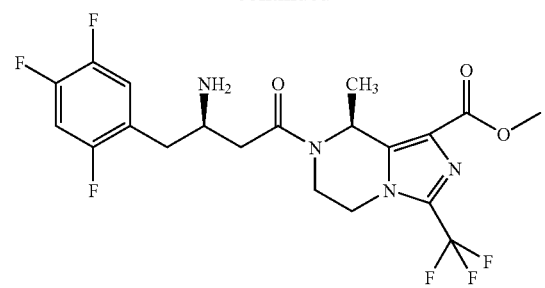
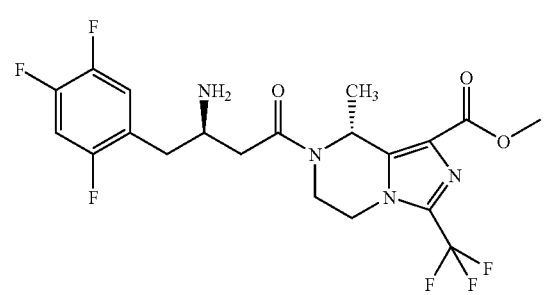
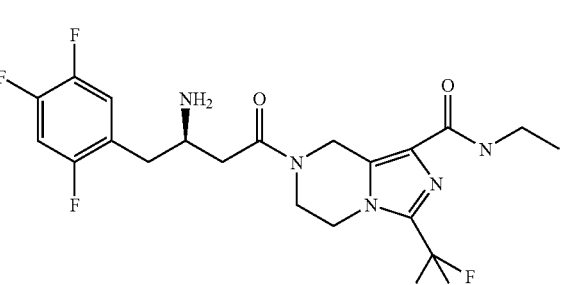
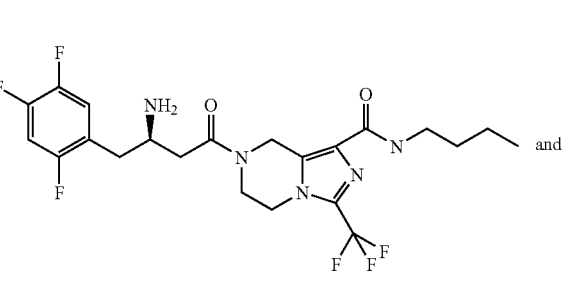
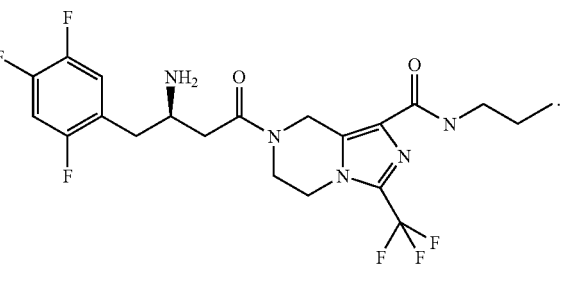
10. The compound, or a pharmaceutically acceptable salt thereof, of claim 1, which is selected from the group consisting of:

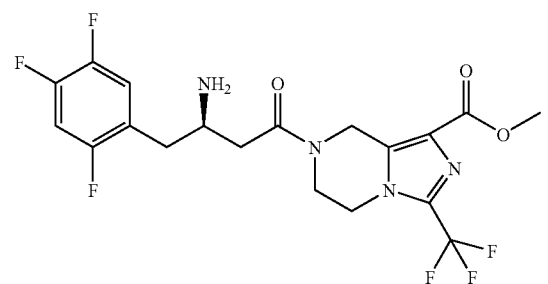

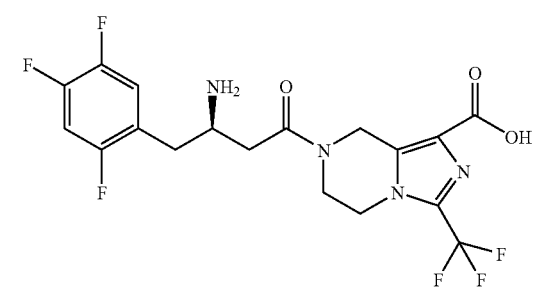

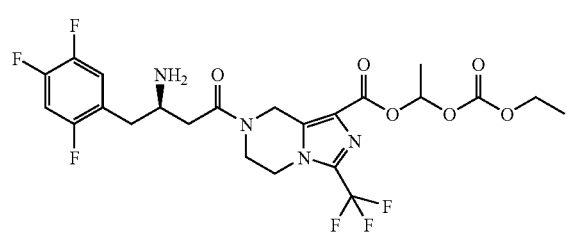

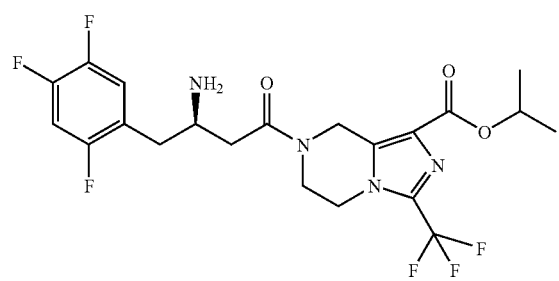

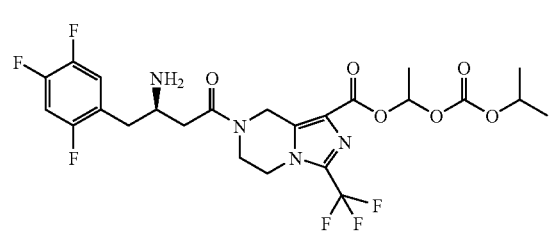

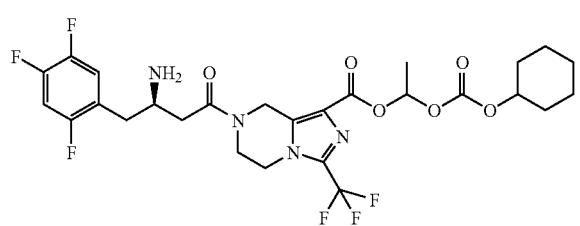

-continued

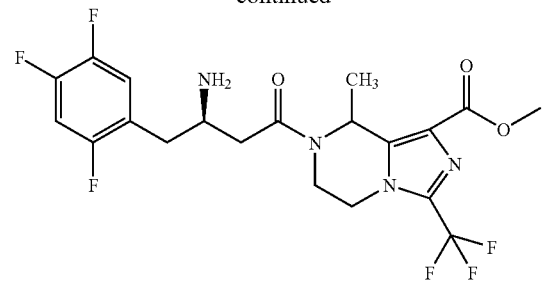

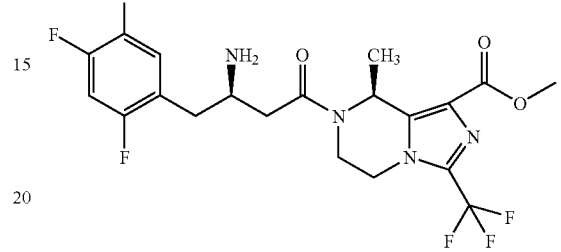

and

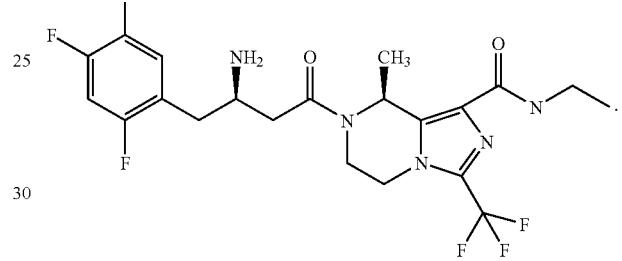

11. The compound, or a pharmaceutically acceptable salt thereof, of claim 1, which is

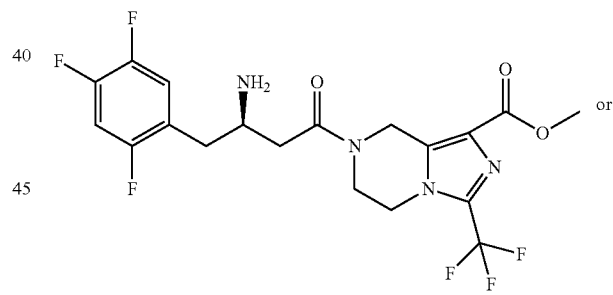 or

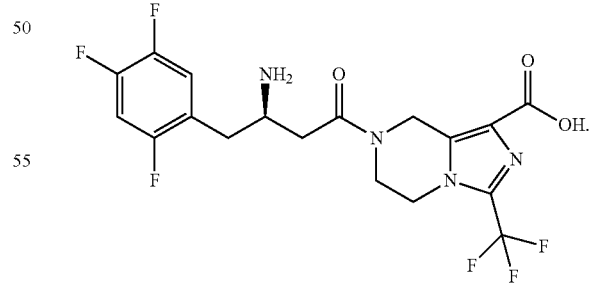

12. The compound, or a pharmaceutically acceptable salt thereof, of claim 1, wherein the pharmaceutically acceptable salt is an addition salt of an acid selected from the group consisting of malic acid, lactic acid, maleic acid, hydrochloric acid, methanesulfonic acid, sulfuric acid, phosphoric acid, citric acid, tartaric acid, acetic acid, and trifluoroacetic acid.

13. The compound, or a pharmaceutically acceptable salt thereof, of claim 12, wherein the acid is hydrochloric acid.

14. A compound of formula (IA):

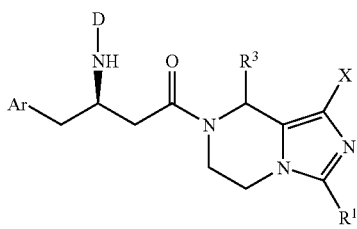

(IA)

wherein:

Ar is phenyl, either unsubstituted or substituted with 1 to 5 substituents independently selected from the group consisting of halogen, cyano, hydroxyl, alkyl or alkoxyl, wherein the alkyl or alkoxyl is each independently unsubstituted or substituted with one or more halogens;

$R^1$ is selected from the group consisting of hydrogen, alkyl, trifluoromethyl, cycloalkyl, aryl and heteroaryl, wherein the alkyl, cycloalkyl, aryl or heteroaryl is each independently either unsubstituted or substituted with one or more groups independently selected from the group consisting of halogen, cyano, aryl, hydroxyl and amino;

$R^3$ is selected from the group consisting of hydrogen and alkyl;

X is halogen; and

D is an amino protected group.

15. The compound of claim 14, wherein Ar is trifluorophenyl.

16. The compound of claim 14, wherein $R^1$ is trifluoromethyl.

17. A process comprising:

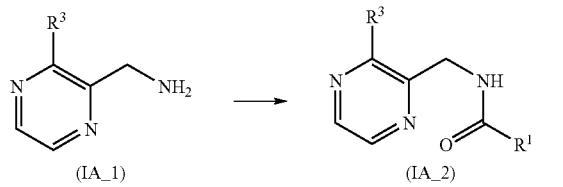

reacting an acid anhydride with pyrazine 2-methylamine (IA_1) to obtain an amide (IA_2), wherein R1 is selected from the group consisting of hydrogen, alkyl, trifluoromethyl, cycloalkyl, aryl and heteroaryl, wherein the alkyl, cycloalkyl, aryl or heteroaryl is each independently either unsubstituted or substituted with one or more groups independently selected from the group consisting of halogen, cyano, aryl, hydroxyl and amino; and R3 is selected from the group consisting of hydrogen and

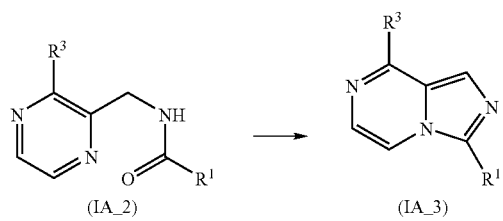

condensing the amide (IA2) to obtain the imidazole[1,5-α]pyrazine derivative (IA_3);

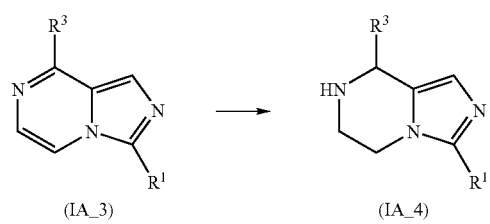

reducing the imidazole[1,5-a]pyrazine derivative (IA_3) to obtain the $R^1$ and $R^3$ substituted tetrahydro-imidazo[1,5-a]pyrazine derivative (IA_4);

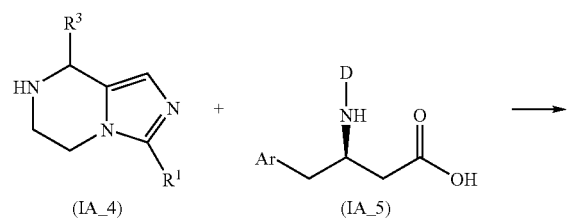

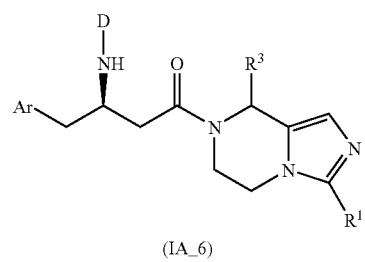

reacting the $R^1$ and $R^3$ substituted tetrahydro-imidazo[1,5-α]pyrazine derivative (IA_4) with a carboxylic acid (IA_5), in the presence of a condensation reagent, to obtain the condensation product (IA_6), wherein Ar is phenyl, either unsubstituted or substituted with 1 to 5 substituents independently selected from the group consisting of halogen, cyano, hydroxyl, alkyl or alkoxyl, wherein the alkyl or alkoxyl is each independently unsubstituted or substituted with one or more halogens; D is an amino protecting group;

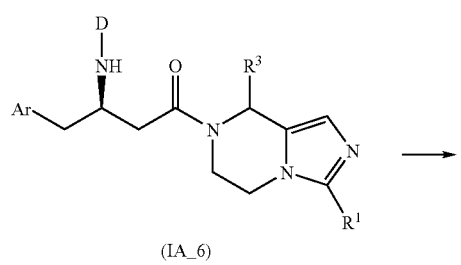

(IA_6)

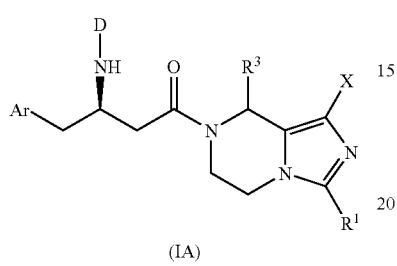

(IA)

halogenating the condensation product (IA__6) to obtain the compound of formula (IA), wherein X is halogen.

18. The process of claim 17, further comprising:

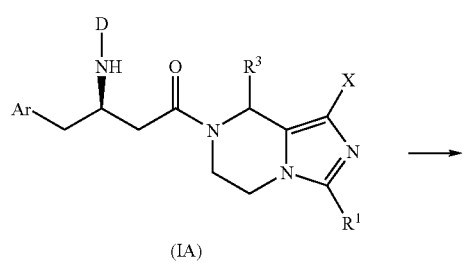

(IA)

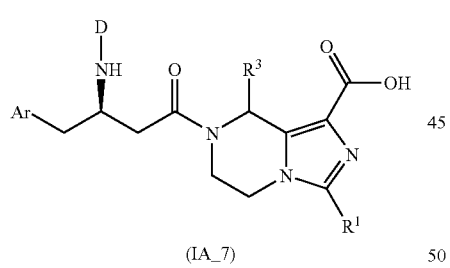

(IA_7)

converting the compound of formula (IA) to the corresponding carboxylic acid (IA__7);

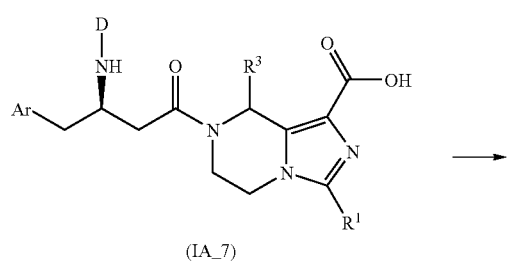

(IA_7)

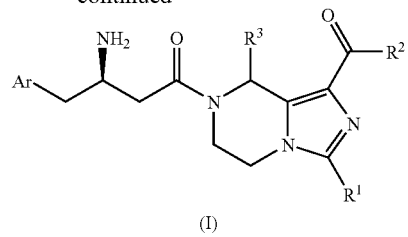

(I)

reacting the carboxylic acid (IA__7) with an amine or an alcohol in the presence of a condensation reagent, or with 1-halogenated carbonate, wherein $R^2$ is selected from the group consisting of hydroxyl, amino, alkyl, alkoxyl, cycloalkyl, heterocyclic alkyl, aryl, heteroaryl and —$NR^4R^5$, wherein the alkyl, alkoxyl, cycloalkyl, heterocyclic alkyl, aryl or heteroaryl is each independently either unsubstituted or substituted with one or more groups independently selected from the group consisting of halogen, amino, cyano, hydroxyl, alkyl, cycloalkyl, alkoxyl, aryl, heteroaryl, —$NR^4R^5$, —OC(O)$OR^8$, carboxylic acid and carboxylic ester; D is an amino protecting group and deprotecting the amino protecting group to obtain the compound of formula (I).

19. A process, comprising:

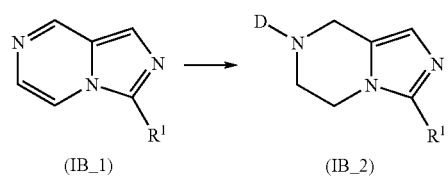

(IB_1)          (IB_2)

reducing the $R^1$ substituted imidazole[1,5-α]pyrazine derivative (IB_I) and protecting the amino group in the resulting reduced product to obtain the amino protected $R^1$ substituted imidazole[1,5-α]pyrazine derivative (IB__2), wherein $R^1$ is selected from the group consisting of hydrogen, alkyl, trifluoromethyl, cycloalkyl, aryl and heteroaryl, wherein the alkyl, cycloalkyl, aryl or heteroaryl is each independently either unsubstituted or substituted with one or more groups independently selected from the group consisting of halogen, cyano, aryl, hydroxyl and amino; D is an amino protecting group;

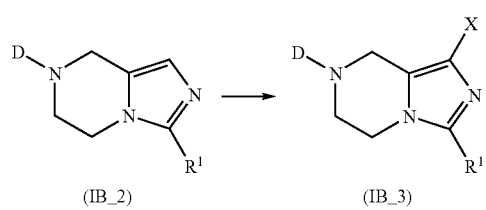

(IB_2)          (IB_3)

halogenating the amino protected $R^1$ substituted imidazole[1,5-α]pyrazine derivative (IB__2) to obtain the halogenated compound (IB__3), wherein X is halogen;

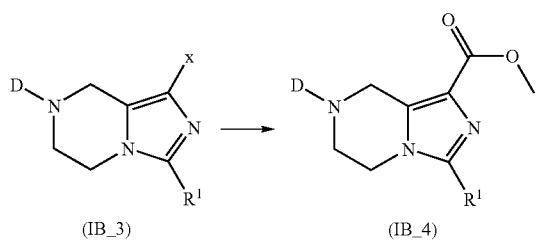

converting the halogenated compound (IB_3) to the ester substituted tetrahydro-imidazo[1,5-α]pyrazine derivative (IB_4);

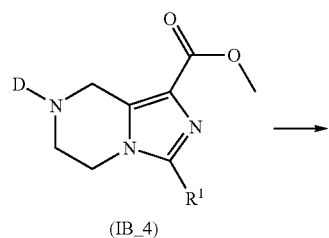

hydrolyzing the ester substituted tetrahydro-imidazo[1,5-a]pyrazine derivative (IB4) to obtain the carboxylic acid compound (IB_5);

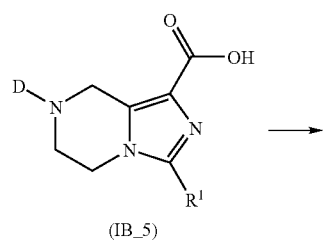

converting the carboxylic acid compound (IB_5) to obtain the compound (IB_6) when $R^3$ is alkyl, wherein $R^3$ is selected from the group consisting of hydrogen and alkyl;

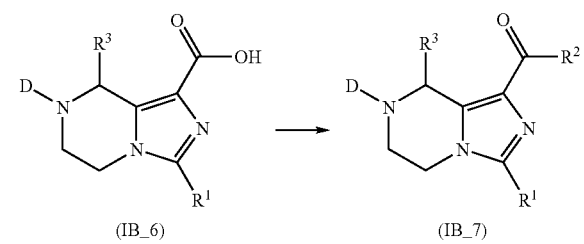

converting the compound (IB_6) to obtain the tetrahydro-imidazo[1,5-a]pyrazine derivative (IB_7), wherein $R^2$ is selected from the group consisting of hydroxyl, amino, alkyl, alkoxyl, cycloalkyl, heterocyclic alkyl, aryl, heteroaryl and —$NR^4R^5$, wherein the alkyl, alkoxyl, cycloalkyl, heterocyclic alkyl, aryl or heteroaryl is each independently either unsubstituted or substituted with one or more groups independently selected from the group consisting of halogen, amino, cyano, hydroxyl, alkyl, cycloalkyl, alkoxyl, aryl, heteroaryl, —$NR^4R^5$, —$OC(O)OR^8$, carboxylic acid and carboxylic ester;

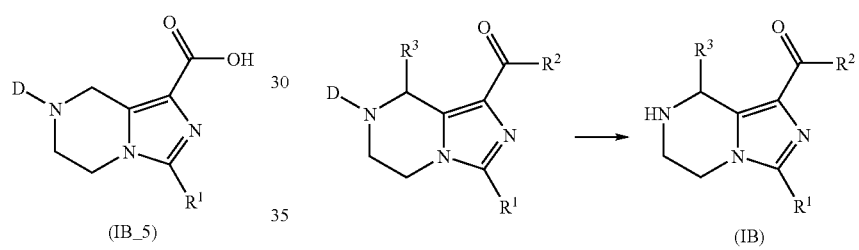

deprotecting the ketone substituted tetrahydro-imidazo[1,5-a']lpyrazine derivative (IB7) to obtain the compound of formula (IB); and

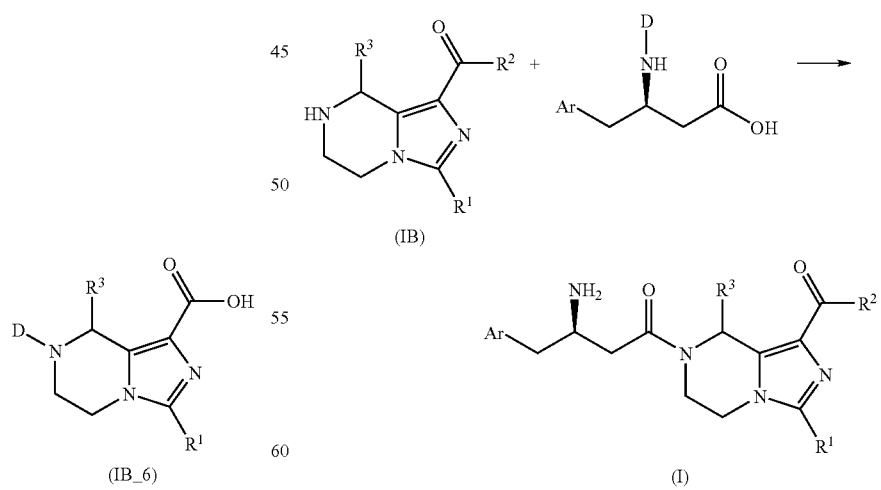

reacting the compound of formula (IB) with a carboxylic acid in the presence of a condensation reagent to obtain the condensation product; and deprotectinq the amino protecting group to obtain the compound of formula (I).

20. A pharmaceutical composition comprising the compound, or a pharmaceutically acceptable salt thereof, of claim 1, and a pharmaceutically acceptable carrier or excipient.

21. A method for treating type 2 diabetes, hyperglycemia, or insulin resistance, comprising administering the pharmaceutical composition of claim 20 to a patient in need of the treatment.

22. A method for treating type 2 diabetes, hyperglycemia, or insulin resistance, comprising administering a therapeutically effective amount of the compound, or a pharmaceutically acceptable salt thereof, of claim 1, to a patient in need of the treatment.

23. A method for inhibiting the catalytic activity of dipeptidyl peptidase IV, comprising contacting dipeptidyl peptidase IV with the compound, or a pharmaceutically acceptable salt thereof, of claim 1.

* * * * *